United States Patent
Roy et al.

(10) Patent No.: US 10,865,181 B2
(45) Date of Patent: Dec. 15, 2020

(54) SMALL MOLECULE INHIBITORS OF THE MITOCHONDRIAL PERMEABILITY TRANSITION PORE (MTPTP)

(71) Applicants: UNIVERSITY OF KANSAS, Lawrence, KS (US); Oregon Health & Science University, Portland, OR (US)

(72) Inventors: Sudeshna Roy, Lawrence, KS (US); Paolo Bernardi, Padua (IT); Michael Forte, Portland, OR (US); Frank Schoenen, Lawrence, KS (US); Justina Sileikyte, Padua (IT)

(73) Assignees: UNIVERSITY OF KANSAS, Lawrence, KS (US); Oregon Health & Science University, Portland, OR (US)

( * ) Notice: Subject to any disclaimer, the term of this patent is extended or adjusted under 35 U.S.C. 154(b) by 0 days.

(21) Appl. No.: 15/524,595

(22) PCT Filed: Nov. 4, 2015

(86) PCT No.: PCT/US2015/059078
§ 371 (c)(1),
(2) Date: May 4, 2017

(87) PCT Pub. No.: WO2016/073633
PCT Pub. Date: May 12, 2016

(65) Prior Publication Data
US 2018/0282264 A1     Oct. 4, 2018

Related U.S. Application Data

(60) Provisional application No. 62/075,643, filed on Nov. 5, 2014.

(51) Int. Cl.
| | |
|---|---|
| *A61K 31/415* | (2006.01) |
| *A61K 31/42* | (2006.01) |
| *A61P 21/00* | (2006.01) |
| *A61P 25/00* | (2006.01) |
| *C07C 235/38* | (2006.01) |
| *C07C 235/42* | (2006.01) |
| *C07C 235/56* | (2006.01) |
| *C07C 203/04* | (2006.01) |
| *C07D 211/14* | (2006.01) |
| *C07D 231/14* | (2006.01) |
| *C07D 261/18* | (2006.01) |
| *C07D 295/135* | (2006.01) |
| *C07D 295/185* | (2006.01) |
| *C07D 413/12* | (2006.01) |
| *C07D 203/04* | (2006.01) |

(52) U.S. Cl.
CPC .......... *C07C 235/42* (2013.01); *A61K 31/415* (2013.01); *A61K 31/42* (2013.01); *A61P 21/00* (2018.01); *A61P 25/00* (2018.01); *C07C 235/38* (2013.01); *C07C 235/56* (2013.01); *C07D 203/04* (2013.01); *C07D 211/14* (2013.01); *C07D 231/14* (2013.01); *C07D 261/18* (2013.01); *C07D 295/135* (2013.01); *C07D 295/185* (2013.01); *C07D 413/12* (2013.01)

(58) Field of Classification Search
CPC combination set(s) only.
See application file for complete search history.

(56) References Cited

U.S. PATENT DOCUMENTS

| 3,752,819 | A | 8/1973 | Philippe |
|---|---|---|---|
| 6,946,462 | B2 | 9/2005 | Haag et al. |
| 8,211,927 | B2 | 7/2012 | Roughton et al. |
| 8,563,580 | B2 | 10/2013 | Padmanabhan et al. |
| 2004/0110802 | A1 | 6/2004 | Thorarensen et al. |
| 2006/0035944 | A1 | 2/2006 | Muto et al. |
| 2009/0069288 | A1* | 3/2009 | Breinlinger .......... C07D 231/14 514/210.18 |
| 2009/0099233 | A1 | 4/2009 | Joshi et al. |
| 2012/0071481 | A1 | 3/2012 | Palin et al. |

FOREIGN PATENT DOCUMENTS

| EP | 0 618 82 A1 | 10/1982 |
|---|---|---|
| WO | WO-2008/022286 A2 | 2/2008 |

OTHER PUBLICATIONS

Chemical Abstract Service STN Registry Database [online] Registry No. 912761-39-8 [Entered STN: Nov. 9, 2006]. (Year: 2006).*
Chemical Abstract Service STN Registry Database [online] Registry No. 912787-79-2 [Entered STN: Nov. 9, 2006]. (Year: 2006).*
PubChem Database [online] CID 3244882 [created Aug. 16, 2005]. (Year: 2005).*
Pubchem Database [online] BioAssay AID 504832 [deposit date: Jun. 22, 2011]. (Year: 2011).*
Chemical Abstract Service STN Database, Registry No. 19925-74-7 [Entered STN: Nov. 16, 1984]. (Year: 1984).*
PubChem CID 3242624 [Create Date: Aug. 16, 2005][Retrieved online from < https://pubchem.ncbi.nlm.nih.gov/compound/3242624>]. (Year: 2005).*
PubChem BioAssay AID 565 [Deposit: Dec. 20, 2006][Retrieved online from < https://pubchem.ncbi.nlm.nih.gov/bioassay/565>]. (Year: 2006).*
International Search Report and Written Opinion in PCT/US15/59078, dated Mar. 2, 2016 (10 pages).
Roy S et al.; Discovery, Synthesis, and Optimization of Diarylisoxazele-3-carboxamides as Potent Inhibitors of the Mitochondrial Permeability Transition Pore; ChemMedChem 10(10),pp. 1-18 (pp. 1655-1671); Oct. 2015.
Extended European search report in EP 15857472.3 dated May 15, 2018.

(Continued)

Primary Examiner — Amanda L. Aguirre
(74) Attorney, Agent, or Firm — Foley & Lardner LLP

(57) ABSTRACT

The present technology relates to compounds of any one of Formula I, II, IIa, III, IV, and/or V as described herein and their tautomers and/or pharmaceutically acceptable salts, compositions, and methods of uses thereof.

13 Claims, 3 Drawing Sheets

(56) References Cited

OTHER PUBLICATIONS

Fancelli et al., Cinnamic Anilides as New Mitochondrial Permeability Transition Pore Inhibitors Endowed with Ischemia-Reperfusion Injury Protective Effect in Vivo, J Med Chem, 2014, 57, 5333-5347 (Abstract Only).

Goel et al., Structure-activity study of antiepileptic N-Arylisoxazolecarboxamides/N-isoxazolylbenzamide analogs using Wiener's topological index, Structural Chemistry, vol. 8, Issue 2, 1997, pp. 155-159 (Abstract Only).

Lepage et al., New N-aryl isoxazolecarboxamides and N-isoxazolylbenzamides as anticonvulsant agents, Eur J Med Chem (1992), 27, pp. 581-593 (Abstract Only).

Li et al., Preparation of novel antibacterial agents. Replacement of the central aromatic ring with heterocycles, Bioorganic & Medicinal Chemistry Letters, vol. 17, Issue 8, 2007, pp. 2347-2350 (Abstract Only).

Schurer et al., Ligand-Binding Pocket Shape Differences between Sphingosine 1-Phosphate (S1P) Receptors S1P1 and S1P3 Determine Efficiency of Chemical Probe Identification by Ultrahigh-Throughput Screening, ACS Chemical Biology, vol. 3, No. 8, 2008, pp. 486-498.

Shimzu et al., Synthesis of Isoxazoline-3-carboxamides and Isoxazole-3-carboxanilides by Thermolysis of a-Methoxycarbonyl-a-nitroacetanilides in the Presence of Dipolarophiles, Synthesis, 1986, Issue 6, pp. 488-490—(Abstract Only).

Tourteau et al., 3-Carboxamido-5-aryl-isoxazoles as new CB2 agonists for the treatment of colitis, Bioorganic & Medicinal Chemistry 21 (2013) 5383-5394.

Veeraswamy et al., "Synthesis of novel 5-substituted isoxazole-3-carboxamide derivatives and cytotoxicity studies on lung cancer cell line," Indian Journal of Chemistry, vol. 51B, Sep. 2012, pp. 1369-1375 (7 pages).

Yarovenko et al., Synthesis of carbamoylformhydroxymoyl chlorides and study of their reactivities, Russian Chemical Bulletin, International Edition, vol. 51, No. 8, pp. 1504-1509, Aug. 2002.

Zhao et al., Design and synthesis of phenylisoxazole derivatives as novel human acrosin inhibitors, Bioorganic & Medicinal Chemistry Letters 24 (2014) 2802-2806 (Abstract Only).

"Homology (chemistry)"; Wikipedia; (https://en.wikipedia.org/wiki/Homology_(chemistry); accessed Dec. 20, 2019); 2 pages.

* cited by examiner

SMALL MOLECULE INHIBITORS OF THE MITOCHONDRIAL PERMEABILITY TRANSITION PORE (MTPTP)

CROSS-REFERENCE TO RELATED PATENT APPLICATIONS

This application is a U.S. National Phase Application under 35 U.S.C. § 371 of International Application No. PCT/US2015/059078, filed on Nov. 4, 2015, which claims priority to U.S. Provisional Patent Application No. 62/075,643, filed Nov. 5, 2014, the entire disclosures of which are hereby incorporated by reference in their entireties for any and all purposes.

GOVERNMENT LICENSE RIGHTS

This invention was made with government support under DA033978 and HG005031 awarded by the National Institutes of Health. The government has certain rights in the invention.

FIELD

The present technology relates to compounds useful as mitochondrial permeability transition pore (mtPTP) inhibitors. In some embodiments, the present technology provides treatments of various diseases involving mtPTP, such as the treatment of multiple sclerosis, amyotropic lateral sclerosis, Alzheimer's disease, Huntington's disease, Parkinson's disease, insulin-induced hypoglycemia, cerebral ischemia, brain damage from epilepsy or experimental trauma, Bethlem myopathy, pancreatitis, hepatitis, diabetic retinopathy, muscular dystrophy, heart infarction, and stroke. The present technology is also generally applicable toward the treatment of disorders governed at least in part by an over-accumulation of reactive oxygen species and/or [$Ca^{2+}$] dysregulation.

BACKGROUND

Mitochondrial permeability transition pore (mtPTP) channel plays a significant role in a variety of human diseases states where common pathology is based upon mitochondrial dysfunction. Mitochondrial permeability transition pore (mtPTP) is a high-conductance channel of the inner mitochondrial membrane (IMM) mediating $Ca^{2+}$ release and affected by voltage, pH and, cyclosporin A (CsA), and activated by an accumulation of mitochondrial $Ca^{2+}$ and oxidative stress.

Although robust assays for the activity of the mtPTP have been established, the identification of small molecule inhibitors has been unexpectedly slow.

There remains a need for compounds which are effective inhibitors of the mtPTP. Compounds that prevent mtPTP opening are useful in treating and preventing cellular damage, [$Ca^{2+}$] dysregulation, and/or the reactive oxygen species associated with oxidative stress-related disorders.

SUMMARY

Herein are disclosed small molecule inhibitors of mtPTP activation. These compounds are "fit-for-purpose" and are useful for therapeutically challenging human diseases, such as, multiple sclerosis, amyotropic lateral sclerosis, Alzheimer's disease, muscular dystrophies, pancreatitis, type II diabetes, heart infarction, and stroke.

The mitochondrial permeability transition pore (mtPTP) is a voltage-dependent, high-conductance channel of the inner mitochondrial membrane activated by mitochondrial accumulation of $Ca^{2+}$. Normal activity of the mtPTP is defined by transient opening of the channel while persistent opening caused by sustained overloads in both mitochondrial and cellular $Ca^{2+}$ ultimately resulting in cell death and numerous conditions of disease. Effectively generating successful therapies for mtPTP-based pathologies has been fairly limited. Early pharmacological agents targeting the mtPTP have been restricted to agents which affect the regulatory component, cyclophilin D.

The inventors diligent studies have found results consistent with the formation of $Ca^{2+}$-dependent conformational changes of dimers of F-ATP synthase as the basis for mtPTP opening. These dimers are highly entropically favored through formation of disulfide bonds. Further, the inventors found that F-ATP synthase switches from a $Mg^{2+}$-dependent system sythesizing ATP into a $Ca^{2+}$ dependent pore (the mtPTP) which decreases the inner mitochondrial membrane (IMM) transmembrane potential. Decrease in IMM potential has been observed to stimulate the opening of the mtPTP. Accordingly, without being bound by theory, the inventors contemplate inhibitors of the $Ca^{2+}$-dependent F-ATP synthase "mtPTP" dimer induce an inhibition of pore opening. Thus, the compounds disclosed herein also treat cellular damage precipitated by [$Ca^{2+}$] dysregulation and/or the reactive oxygen species associated with oxidative stress-related disorders.

In an aspect, the present technology provides compounds of Formula I:

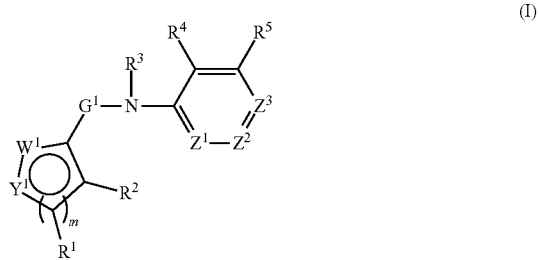

or a pharmaceutically acceptable salt thereof, where:
$Y^1$ and $W^1$ are each independently are O, N, NH, $NR^6$, S, CH, or $CR^7$, or $Y^1$ and $W^1$ are each independently $CR^8$ or $NR^8$ where $R^8$ joins $Y^1$ and $W^1$ to form an aryl, heteroaryl, or heterocylyl ring; $Z^1$, $Z^2$, and $Z^3$ are each independently CH, C—$R^9$, or N; m is 1 or 2; $G^1$ is C=O, C=S, SO, or $SO_2$; $R^1$, $R^2$, $R^4$, $R^5$, $R^6$, $R^7$, and $R^9$ are independently at each occurrence hydrogen, halogen, hydroxyl, alkyl, cycloalkyl, alkenyl, alkoxy, alkynyl, amino, aminosulfinyl, aminosulfonyl, sulfinyl, sulfonyl, sulfonyloxy, aminosulfonyloxy, aminosulfinyloxy, aminosulfonylamino, acylamino, aminocarbonyloxy, aminocarbonylamino, aminothiocarbonylamino, aminocarbonyl, acyloxy, aryl, heteroaryl, cyano, nitro, carboxyl, carboxyl ester, (carboxyl ester)amino, (carboxyl ester)oxy, acyl, or formyl; or two adjacent $R^1$, $R^2$, $R^4$, $R^5$, $R^6$, $R^7$, and $R^9$ together form an aryl, heteroaryl, or heterocyclyl ring; and $R^3$ is hydrogen, alkyl, cycloalkyl, alkenyl, or alkynyl.

In an aspect, the present technology provides compounds of Formula IV:

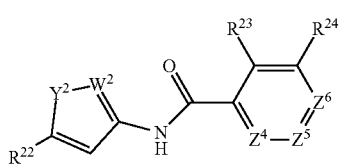

(IV)

or a pharmaceutically acceptable salt thereof, where:
$Y^2$ is O, NH, $NR^{25}$, or S;
$W^2$ is N, CH, or $CR^{26}$; where when $Y^2$ is $NR^{25}$ and $W^2$ is $CR^{26}$ then $R^{25}$ and $R^{26}$ may optionally join $Y^2$ and $W^2$ to form an aryl, heteroaryl, or heterocylyl ring; $Z^4$, $Z^5$, and $Z^6$ are each independently CH, C—$R^{27}$, or N; and
$R^{22}$, $R^{23}$, $R^{24}$, $R^{25}$, $R^{26}$, and $R^{27}$ are independently at each occurrence hydrogen, halogen, hydroxyl, alkyl, cycloalkyl, alkenyl, alkoxy, alkynyl, amino, aminosulfinyl, aminosulfonyl, sulfinyl, sulfonyl, sulfonyloxy, aminosulfonyloxy, aminosulfinyloxy, aminosulfonylamino, acylamino, aminocarbonyloxy, aminocarbonylamino, aminothiocarbonylamino, aminocarbonyl, acyloxy, aryl, heteroaryl, cyano, nitro, carboxyl, carboxyl ester, (carboxyl ester)amino, (carboxyl ester)oxy, acyl, or formyl; or two $R^{22}$, $R^{23}$, $R^{24}$, $R^{25}$, $R^{26}$, and $R^{27}$ together form an aryl, heteroaryl, or heterocyclyl ring.

In an aspect, the compound of the present technology is a compound of Formula V:

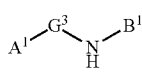

(V)

or a pharmaceutically acceptable salt thereof, where $G^3$ is C=O, C=S, or $SO_2$; and $A^1$ and $B^1$ are each independently alkyl, cycloalkyl, aryl, or heteroaryl.

In a related aspect, pharmaceutical compositions are provided that include one or more compounds of Formula I, II, IIa, III, IV, and/or V described herein and a pharmaceutically acceptable excipient. The pharmaceutical composition may include one or more mitochondrial targeting molecules, including but not limited to any one or more of the mitochondrial targeting molecules described in Wipf et. al. "Targeting Mitochondria" *Acc. Chem. Res.* 2008, 41, 87-97 and references cited therein, each of which is incorporated by reference in their entireties for any and all purposes.

In an aspect, a method is provided for treating a disease mediated at least in part by [$Ca^{2+}$] dysregulation and/or an accumulation of by a reactive oxygen species, where the method involves administering to a patient an effective amount of one or more compounds of Formula I, II, IIa, III, IV, and/or V, or a pharmaceutical composition comprising a pharmaceutically acceptable excipient and an effective amount of one or more compounds of Formula I, II, IIa, III, IV, and/or V described herein.

Diseases mediated at least in part by [$Ca^{2+}$] dysregulation and/or the accumulation of by a reactive oxygen species include those selected from the group consisting of Huntington's disease and other polyglutamine disorders, ischemic reperfusion injury, multiple sclerosis, amyotropic lateral sclerosis, Alzheimer's disease, Huntington's disease, Parkinson's disease, insulin-induced hypoglycaemia, cerebral ischemia, brain damage from epilepsy or experimental trauma, Bethlem myopathy, pancreatitis, hepatitis, diabetic retinopathy, muscular dystrophy, traumatic brain injury, type II diabetes, heart infarction, stroke, general central nervous system (CNS) infections such as viral, bacterial or parasites, for example, poliomyelitis, Lyme disease (*Borrelia burgdorferi* infection) and malaria, cancers with cerebral localization, Tourette's syndrome, hepatic encephalopathy, systemic lupus, analgesia and opiate withdrawal symptoms, feeding behaviour, schizophrenia, chronic anxiety, depressive disorders, disorders of the developing or aged brain, diseases of addiction, diabetes, and complications thereof.

In an aspect, an article of manufacture is provided for use in inhibiting mtPTP and treating a disease mediated at least in part by [$Ca^{2+}$] dysregulation and/or a reactive oxygen species, where the article includes a composition that includes a compound of Formula I, II, IIa, III, IV, and/or V as provided herein. The article of manufacture may further include a label with instructions for using the composition to treat the disease.

These and other embodiments are described in further detail herein.

DETAILED DESCRIPTION

Figure 1:
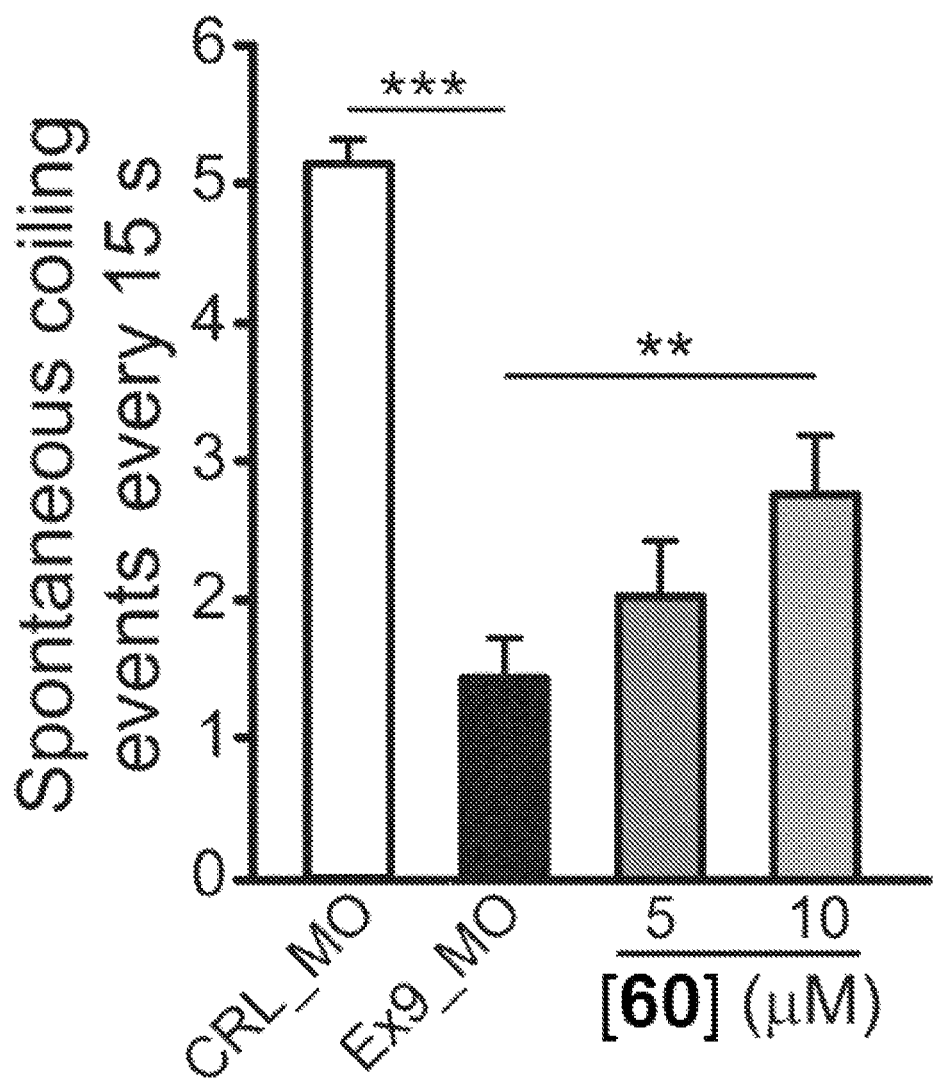
FIG. 1 presents coiling events in control (CRL_MO) zebrafish embryos and exon 9 col6a1 morphant (Ex9_MO) zebrafish embryos, where exon 9 col6a1 morphant (Ex9_MO) zebrafish embryos were further tested with the indicated concentrations of a compound of the present technology.

Throughout this application, the text refers to various embodiments of the present compounds, compositions, and methods. The various embodiments described are meant to provide a variety of illustrative examples and should not be construed as descriptions of alternative species. Specific embodiments are not intended as an exhaustive description or as a limitation to the broader aspects discussed herein. One aspect described in conjunction with a particular embodiment is not necessarily limited to that embodiment and can be practiced with any other embodiment(s).

1. Definitions

As used herein, the following definitions shall apply unless otherwise indicated. Further, if any term or symbol used herein is not defined as set forth below, it shall have its ordinary meaning in the art.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element, such as hydrogen or H, is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an alkyl, cycloalkyl, alkenyl, alkynyl, heterocyclyl, aryl, heteroaryl, or ether group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkyl, aryl, hetercyclyl, heteroaryl, alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

As used herein, $C_m$-$C_n$, such as $C_1$-$C_{12}$, $C_1$-$C_8$, or $C_1$-$C_6$ when used before a group refers to that group containing m to n carbon atoms.

"Alkyl" refers to monovalent saturated aliphatic hydrocarbyl groups having from 1 to 10 carbon atoms and preferably 1 to 6 carbon atoms. Alkyl groups may be unsubstituted or unsubstituted as well as linear or branched. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—). Preferred substituted alkyl groups include halogenated alkyl groups and particularly halogenated methyl groups such as trifluoromethyl, difluromethyl, fluoromethyl and the like.

"Alkenyl" refers to straight or branched hydrocarbyl groups having from 2 to 6 carbon atoms and preferably 2 to 4 carbon atoms and having at least 1 and preferably from 1 to 2 sites of unsaturation. Alkenyl groups may be unsubstituted or substituted. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—CH$_2$C≡CH). Alkynyl groups may be unsubstituted or substituted.

"Alkoxy" refers to the group —O-alkyl wherein alkyl is defined herein. Alkoxy groups may be unsubstituted or substituted. Alkoxy includes, by way of example, methoxy, ethoxy, n-propoxy, isopropoxy, n-butoxy, t-butoxy, sec-butoxy, and n-pentoxy. Preferred substituted alkoxy groups (—O-(substituted alkyl)) include halogenated alkyl groups and particularly halogenated methyl groups such as trifluoromethyl, difluromethyl, fluoromethyl, and the like.

"Acyl" refers to the groups H—C(O)—, alkyl-C(O)—, alkenyl-C(O)—, alkynyl-C(O)—, cycloalkyl-C(O)—, aryl-C(O)—, heteroaryl-C(O)—, and heterocyclyl-C(O)—.

"Acylamino" refers to the groups —NR$^{130}$C(O)alkyl, —NR$^{130}$C(O)cycloalkyl, —NR$^{130}$C(O)alkenyl, —NR$^{130}$C(O)alkynyl, —NR$^{130}$C(O)aryl, —NR$^{130}$C(O)heteroaryl, and —NR$^{30}$C(O)heterocyclyl, wherein R$^{130}$ is independently at each occurrence hydrogen or alkyl.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—.

"Amino" refers to —NR$^{131}$R$^{132}$ where R$^{131}$ and R$^{132}$ are each independently hydrogen, alkyl, alkenyl, alkoxy, alkynyl, aryl, cycloalkyl, heteroaryl, heterocyclyl, or sulfonyl. When R$^{131}$ is hydrogen and R$^{132}$ is alkyl, the substituted amino group is sometimes referred to herein as alkylamino. When R$^{131}$ and R$^{132}$ are alkyl, the substituted amino group is sometimes referred to herein as dialkylamino. When referring to a monosubstituted amino, it is meant that either R$^{131}$ or R$^{132}$ is hydrogen but not both. When referring to a disubstituted amino, it is meant that neither R$^{131}$ nor R$^{132}$ are hydrogen.

"Aminocarbonyl" refers to the group —C(O)NR$^{133}$R$^{134}$ where R$^{133}$ and R$^{134}$ are each independently hydrogen, alkyl, alkenyl, alkoxy, alkynyl, aryl, cycloalkyl, heteroaryl, or heterocyclyl, where R$^{133}$ and R$^{134}$ are optionally joined together with the nitrogen bound thereto to form a heterocyclic group.

"Aminothiocarbonyl" refers to the group —C(S)NR$^{135}$R$^{136}$ where R$^{135}$ and R$^{136}$ are independently selected from the group consisting of hydrogen, alkyl, alkenyl, alkoxy, alkynyl, aryl, cycloalkyl, heteroaryl, and heterocyclyl, where $R^{135}$ and $R^{136}$ are optionally joined together with the nitrogen bound thereto to form a heterocyclic or substituted heterocyclic group.

"Aminocarbonylamino" refers to the group —$NR^{137}C(O)NR^{138}R^{139}$ where $R^{137}$ is hydrogen or alkyl and $R^{138}$ and $R^{139}$ are independently selected from the group consisting of hydrogen, alkyl, alkenyl, alkoxy, alkynyl, aryl, cycloalkyl, heteroaryl, and heterocyclyl, where $R^{138}$ and $R^{139}$ are optionally joined together with the nitrogen bound thereto to form a heterocyclic group.

"Aminothiocarbonylamino" refers to the group —$NR^{140}C(S)NR^{141}R^{142}$ where $R^{140}$ is hydrogen or alkyl and $R^{141}$ and $R^{142}$ are independently selected from the group consisting of hydrogen, alkyl, alkenyl, alkoxy, alkynyl, aryl, cycloalkyl, heteroaryl, and heterocyclyl, where $R^{141}$ and $R^{142}$ are optionally joined together with the nitrogen bound thereto to form a heterocyclic group.

"Aminocarbonyloxy" refers to the group —O—C(O)$NR^{143}R^{144}$ where $R^{143}$ and $R^{144}$ are independently selected from the group consisting of hydrogen, alkyl, alkenyl, alkoxy, alkynyl, aryl, cycloalkyl, heteroaryl, and heterocyclyl, where $R^{143}$ and $R^{144}$ are optionally joined together with the nitrogen bound thereto to form a heterocyclic group.

"Aminosulfonyl" refers to the group —$SO_2NR^{145}R^{146}$ where $R^{145}$ and $R^{146}$ are independently selected from the group consisting of hydrogen, alkyl, alkenyl, alkoxy, alkynyl, aryl, cycloalkyl, heteroaryl, and heterocyclyl, where $R^{145}$ and $R^{146}$ are optionally joined together with the nitrogen bound thereto to form a heterocyclic group.

"Aminosulfonyloxy" refers to the group —O—$SO_2NR^{147}R^{148}$ where $R^{147}$ and $R^{148}$ are each independently selected from the group consisting of hydrogen, alkyl, alkenyl, alkoxy, alkynyl, aryl, cycloalkyl, heteroaryl, and heterocyclyl, where $R^{147}$ and $R^{148}$ are optionally joined together with the nitrogen bound thereto to form a heterocyclic group.

"Aminosulfonylamino" refers to the group —$NR^{149}$—$SO_2NR^{150}R^{151}$ where $R^{149}$ is hydrogen or alkyl and $R^{150}$ and $R^{151}$ are independently selected from the group consisting of hydrogen, alkyl, alkenyl, alkoxy, alkynyl, aryl, cycloalkyl, heteroaryl, and heterocyclyl, where $R^{150}$ and $R^{151}$ are optionally joined together with the nitrogen bound thereto to form a heterocyclic group.

"Amidino" refers to the group —C(=$NR^{152}$)$NR^{153}R^{154}$ where $R^{152}$, $R^{153}$, and $R^{154}$ are independently selected from the group consisting of hydrogen, alkyl, alkenyl, alkoxy, alkynyl, aryl, cycloalkyl, heteroaryl, and heterocyclyl, where $R^{153}$ and $R^{154}$ are optionally joined together with the nitrogen bound thereto to form a heterocyclic group.

"Aryl" or "Ar" refers to a monovalent aromatic carbocyclic group of from 6 to 14 carbon atoms having a single ring (e.g., phenyl (Ph)) or multiple condensed rings (e.g., naphthyl or anthryl) which condensed rings may or may not be aromatic (e.g., 2-benzoxazolinone, 2H-1,4-benzoxazin-3 (4H)-one-7-yl, and the like) provided that the point of attachment is at an aromatic carbon atom. Aryl groups may be unsubstituted or substituted. Preferred aryl groups include phenyl and naphthyl. Substituted aryl includes aryl groups which are substituted with 1 to 5, preferably 1 to 3, or more preferably 1 to 2 substituents.

"Aryloxy" refers to the group —O-aryl, where aryl is as defined herein, that includes, by way of example, phenoxy and naphthoxy.

"Arylthio" refers to the group —S-aryl, where aryl is as defined herein.

"Carbonyl" refers to the divalent group —C(O)— which is equivalent to —C(=O)—.

"Carboxy" or "carboxyl" refers to —COOH or salts thereof.

"Carboxy ester" or "carboxy ester" refers to the groups —C(O)O-alkyl, —C(O)O-alkenyl, —C(O)O-alkynyl, —C(O)O-aryl, —C(O)O-cycloalkyl, —C(O)O-heteroaryl, and —C(O)O-heterocyclyl.

"(Carboxyl ester)amino" refers to the groups —$NR^{155}$—C(O)O-alkyl, —$NR^{155}$—C(O)O-alkenyl, —$NR^{155}$—C(O)O-alkynyl, —$NR^{155}$—C(O)O-aryl, —$NR^{155}$—C(O)O-cycloalkyl, —$NR^{155}$—C(O)O-heteroaryl, and —$NR^{155}$—C(O)O-heterocyclyl, wherein $R^{155}$ is independently at each occurrence alkyl or hydrogen.

"(Carboxyl ester)oxy" refers to the groups —O—C(O)O-alkyl, —O—C(O)O-alkenyl, —O—C(O)O-alkynyl, —O—C(O)O-aryl, —O—C(O)O-cycloalkyl, —O—C(O)O-heteroaryl, and —O—C(O)O-heterocyclyl.

"Cyano" refers to the group —C≡N.

"Cycloalkyl" refers to a saturated or unsaturated but nonaromatic cyclic alkyl groups of from 3 to 10 ring carbon atoms having single or multiple cyclic rings including fused, bridged, and Spiro ring systems. Cycloalkyl groups may be unsubstituted or substituted. "$C_x$ cycloalkyl" refers to a cycloalkyl group having x number of ring carbon atoms. Examples of suitable cycloalkyl groups include, for instance, adamantyl, cyclopropyl, cyclobutyl, cyclopentyl, and cyclooctyl.

"Cycloalkyloxy" refers to —O-cycloalkyl.

"Cycloalkylthio" refers to —S-cycloalkyl.

"Guanidino" refers to —$NR^{156}$C(=$NR^{157}$)N($R^{158}$)$_2$ where $R^{156}$ and $R^{157}$ are each independently hydrogen, alkyl, aryl, heteroaryl, and heterocyclyl, and $R^{158}$ is independently at each occurrence hydrogen, alkyl, aryl, heteroaryl, and heterocyclyl and two $R^{158}$ groups are optionally joined together with the nitrogen bound thereto to form a heterocyclyl group.

"Halo" or "halogen" refers to fluoro, chloro, bromo and iodo and preferably is fluoro or chloro.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. Heteroaryl groups may be unsubstituted or substituted. The nitrogen and/or the sulfur ring atom(s) of the heteroaryl group may optionally be oxidized to provide for the N-oxide (N→O), sulfinyl, or sulfonyl moieties. Preferred heteroaryls include 5 or 6 membered heteroaryls such as pyridinyl, pyrrolyl, indolyl, thiophenyl, and furanyl.

"Heteroaryloxy" refers to —O-heteroaryl.

"Heteroarylthio" refers to the group —S-heteroaryl.

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocyclyl groups may be unsubstituted or substituted. "$C_x$ heterocyclyl" refers to a heterocycloalkyl group having x number of ring atoms including the ring heteroatoms. Heterocycle encompasses single ring or multiple condensed rings, including fused bridged and Spiro ring systems. In fused ring systems, one or more of the rings can be cycloalkyl, aryl or heteroaryl provided that the point of attachment is through the non-aromatic ring. The nitrogen and/or sulfur atom(s) of the heterocyclic group may optionally be oxidized to provide for the N-oxide, sulfinyl, sulfonyl moieties.

"Heterocyclyloxy" refers to the group —O-heterocycyl.

"Heterocyclylthio" refers to the group —S-heterocycyl.

Examples of heterocyclyl and heteroaryl include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —$NO_2$.

"Oxo" refers to (=O) or (O$^-$).

"Spiro ring systems" refers to bicyclic ring systems that have a single ring carbon atom common to both rings.

"Sulfinyl" refers to the divalent group —SO—.

"Sulfonyl" refers to the divalent group —$S(O)_2$— where a "substituted sulfonyl" is —$SO_2$-alkyl, —$SO_2$—OH, —$SO_2$-alkenyl, —$SO_2$-cycloalkyl, —$SO_2$-aryl, —$SO_2$-heteroaryl, and —$SO_2$-heterocyclyl. Sulfonyl groups may be unsubstituted or substituted. Substituted sulfonyl includes groups such as methyl-$SO_2$—, phenyl-$SO_2$—, and 4-methylphenyl-$SO_2$—. Preferred substituted alkyl groups on the substituted alkyl-$SO_2$— include halogenated alkyl groups and particularly halogenated methyl groups such as trifluoromethyl, difluromethyl, fluoromethyl and the like.

"Sulfonyloxy" refers to —$OSO_2$-alkyl, —$OSO_2$—OH, —$OSO_2$-alkenyl, —$OSO_2$-cycloalkyl, —$OSO_2$-aryl, —$OSO_2$-heteroaryl, and —$OSO_2$-heterocyclyl.

"Thioacyl" refers to H—C(S)—, alkyl-C(S)—, alkenyl-C(S)—, alkynyl-C(S)—, cycloalkyl-C(S)—, aryl-C(S)—, heteroaryl-C(S)—, and heterocyclyl-C(S)—.

"Mercapto" or "thiol" refers to the group —SH.

"Formyl" refers to the group —C(O)H.

"Thiocarbonyl" refers to the divalent group —C(S)— which is equivalent to —C(=S)—.

"Thione" refers to the atom (=S).

"Alkylthio" refers to the group —S-alkyl.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

"Tautomers" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

Unless indicated otherwise, the nomenclature of substituents that are not explicitly defined herein are arrived at by naming the terminal portion of the functionality followed by the adjacent functionality toward the point of attachment. For example, the substituent "alkoxycarbonylalkyl" refers to the group (alkoxy)-C(O)-(alkyl)-.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

It is understood that the above definitions are not intended to include impermissible substitution patterns (e.g., methyl substituted with 5 fluoro groups). Such impermissible substitution patterns are well known to the skilled artisan.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g. $Na^+$, $Li^+$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

2. Compounds of the Present Technology

The present technology is directed to compounds, compositions, and methods of using said compounds as inhibiting the mtPTP. The compounds of the present technology are useful in treating a variety of disorders, such as those mediated at least in part by [Ca$^{2+}$] dysregulation and/or the accumulation of by a reactive oxygen species.

In an aspect, the present technology provides compounds of Formula I:

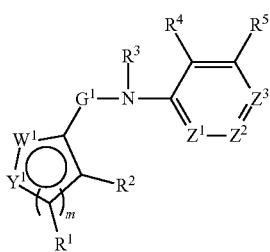

or a pharmaceutically acceptable salt thereof, where:
Y$^1$ and W$^1$ are each independently are O, N, NH, NR$^6$, S, CH, or CR$^7$, or Y$^1$ and W$^1$ are each independently CR$^8$ or NR$^8$ where R$^8$ joins Y$^1$ and W$^1$ to form an aryl, heteroaryl, or heterocylyl ring; Z$^1$, Z$^2$, and Z$^3$ are each independently CH, C—R$^9$, or N; m is 1 or 2; G$^1$ is C=O, C=S, SO, or SO$_2$; R$^1$, R$^2$, R$^4$, R$^5$, R$^6$, R$^7$, and R$^9$ are independently at each occurrence hydrogen, halogen, hydroxyl, alkyl, cycloalkyl, alkenyl, alkoxy, alkynyl, amino, aminosulfinyl, aminosulfonyl, sulfinyl, sulfonyl, sulfonyloxy, aminosulfonyloxy, aminosulfinyloxy, aminosulfonylamino, acylamino, aminocarbonyloxy, aminocarbonylamino, aminothiocarbonylamino, aminocarbonyl, acyloxy, aryl, heterocyclyl, heteroaryl, cyano, nitro, carboxyl, carboxyl ester, (carboxyl ester)amino, (carboxyl ester)oxy, acyl, or formyl; or two adjacent R$^1$, R$^2$, R$^4$, R$^5$, R$^6$, R$^7$, and R$^9$ together form an aryl, heteroaryl, or heterocyclyl ring; and R$^3$ is hydrogen, alkyl, cycloalkyl, alkenyl, or alkynyl.

The compound of Formula I may be a compound of Formula II or III:

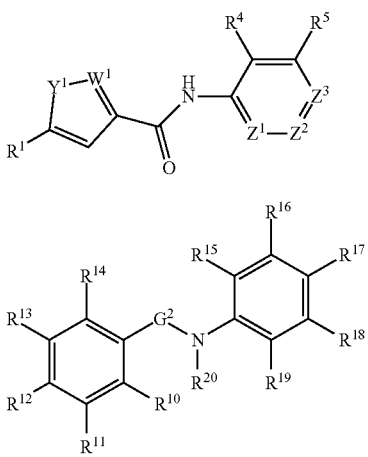

or a pharmaceutically acceptable salt thereof, where:
Y$^1$ is O, NH, NR$^6$, or S;
W$^1$ is N, CH, or CR$^7$;
Z$^1$, Z$^2$, Z$^3$, R$^4$ and R$^5$ are as defined above;
G$^2$ is C=O, C=S, SO, or SO$_2$;
R$^{10}$, R$^{11}$, R$^{12}$, R$^{13}$, R$^{14}$, R$^{15}$, R$^{16}$, R$^{17}$, R$^{18}$, and R$^{19}$ are independently at each occurrence hydrogen, halogen, hydroxyl, alkyl, cycloalkyl, alkenyl, alkoxy, alkynyl, amino, aminosulfinyl, aminosulfonyl, sulfinyl, sulfonyl, sulfonyloxy, aminosulfonyloxy, aminosulfinyloxy, aminosulfonylamino, acylamino, aminocarbonyloxy, aminocarbonylamino, aminothiocarbonylamino, aminocarbonyl, acyloxy, aryl, heterocyclyl, heteroaryl, cyano, nitro, carboxyl, carboxyl ester, (carboxyl ester)amino, (carboxyl ester)oxy, acyl, or formyl; or two adjacent R$^{10}$, R$^{11}$, R$^{12}$, R$^{13}$, R$^{14}$, R$^{15}$, R$^{16}$, R$^{17}$, R$^{18}$, and R$^{19}$ together form an aryl, heteroaryl, or heterocyclyl ring; and
R$^{20}$ is hydrogen, alkyl, cycloalkyl, alkenyl, or alkynyl.

In any embodiment herein, R$^1$, R$^2$, R$^4$, R$^5$, R$^6$, R$^7$, R$^9$, R$^{10}$, R$^{11}$, R$^{12}$, R$^{13}$, R$^{14}$, R$^{15}$, R$^{16}$, R$^{17}$, R$^{18}$, and/or R$^{19}$ may independently at each occurrence be hydrogen, C$_1$-C$_8$ alkyl, C$_3$-C$_8$ cycloalkyl, C$_1$-C$_8$ alkenyl, C$_2$-C$_8$ alkynyl, aryl, cyano, carboxyl, carboxyl ester, acyl, formyl, C$_3$-C$_7$ heteroaryl, or C$_3$-C$_7$ heterocyclyl, or two adjacent R$^1$, R$^2$, R$^4$, R$^5$, R$^6$, R$^7$, R$^9$, R$^{10}$, R$^{11}$, R$^{12}$, R$^{13}$, R$^{14}$, R$^{15}$, R$^{16}$, R$^{17}$, R$^{18}$, and/or R$^{19}$ together form an aryl, heteroaryl, or heterocyclyl ring.

The compound of Formula II may be a compound of formula IIa:

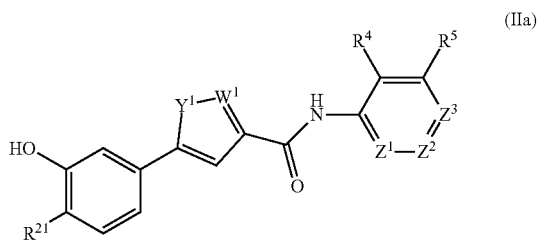

where R$^{21}$ is H, F, Cl, or alkoxy. In any embodiment herein, R$^{21}$ may be H, F, Cl, or methoxy. In any embodiment herein, Z$^1$ may be CH. In any embodiment herein, it may be that Y$^1$ is O and W$^1$ is N or Y$^1$ is NH and W$^1$ is N.

In an aspect, the present technology provides compounds of Formula IV:

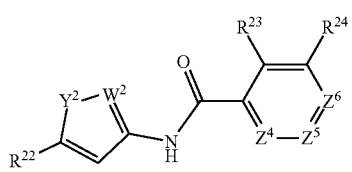

or a pharmaceutically acceptable salt thereof, where:
Y$^2$ is O, NH, NR$^{25}$, or S;
W$^2$ is N, CH, or CR$^{26}$; where when Y$^2$ is NR$^{25}$ and W$^2$ is CR$^{26}$ then R$^{25}$ and R$^{26}$ may optionally join Y$^2$ and W$^2$ to form an aryl, heteroaryl, or heterocylyl ring;
Z$^4$, Z$^5$, and Z$^6$ are each independently CH, C—R$^{27}$, or N; and
R$^{22}$, R$^{23}$, R$^{24}$, R$^{25}$, R$^{26}$, and R$^{27}$ are independently at each occurrence hydrogen, halogen, hydroxyl, alkyl, cycloalkyl, alkenyl, alkoxy, alkynyl, amino, aminosulfinyl, aminosulfonyl, sulfinyl, sulfonyl, sulfonyloxy, aminosulfonyloxy, aminosulfinyloxy, aminosulfonylamino, acylamino, aminocarbonyloxy, aminocarbonylamino, aminothiocarbonylamino, aminocarbonyl, acyloxy, aryl, heteroaryl, cyano, nitro, carboxyl, carboxyl ester, (carboxyl ester)amino, (carboxyl ester)oxy, acyl, or formyl; or two R$^{22}$, R$^{23}$, R$^{24}$, R$^{25}$, R$^{26}$, and R$^{27}$ together form an aryl, heteroaryl, or heterocyclyl ring.

In an aspect, the compound of the present technology is a compound of Formula V:

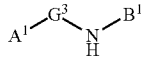
(V)

or a pharmaceutically acceptable salt thereof, where $G^3$ is C=O, C=S, or $SO_2$; and $A^1$ and $B^1$ are each independently alkyl, cycloalkyl, aryl, or heteroaryl.

For example, a compound according for Formula V includes compounds of Formulas VI and VII:

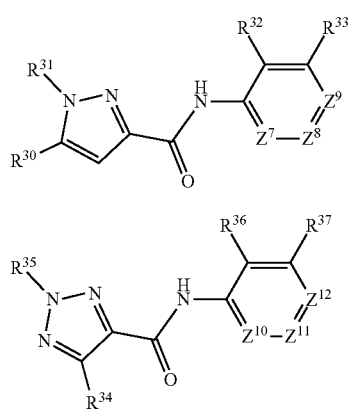

or a pharmaceutically acceptable salt thereof, where:
$Z^7$, $Z^8$, $Z^9$, $Z^{10}$, $Z^{11}$, and $Z^{12}$ are each independently CH, C—$R^{38}$, or N; and
$R^{30}$, $R^{32}$, $R^{33}$, $R^{34}$, $R^{36}$, and $R^{37}$ are independently at each occurrence hydrogen, halogen, hydroxyl, alkyl, cycloalkyl, alkenyl, alkoxy, alkynyl, amino, aminosulfinyl, aminosulfonyl, sulfonyl, sulfonyl, sulfonyloxy, aminosulfonyloxy, aminosulfinyloxy, aminosulfonylamino, acylamino, aminocarbonyloxy, aminocarbonylamino, aminothiocarbonylamino, aminocarbonyl, acyloxy, aryl, heteroaryl, cyano, nitro, carboxyl, carboxyl ester, (carboxyl ester)amino, (carboxyl ester)oxy, acyl, or formyl; or two adjacent $R^{32}$, $R^{33}$, $R^{36}$, and $R^{37}$ together form an aryl, heteroaryl, or heterocyclyl ring; and
$R^{31}$ and $R^{35}$ are each independently hydrogen, alkyl, cycloalkyl, alkenyl, alkynyl, aryl, or heteroaryl.

The compound of Formula I, II, IIa, III, IV, and/or V may be any one of the compounds shown below and in Tables 1 & 2 herein, as well as pharmaceutically acceptable salts thereof.

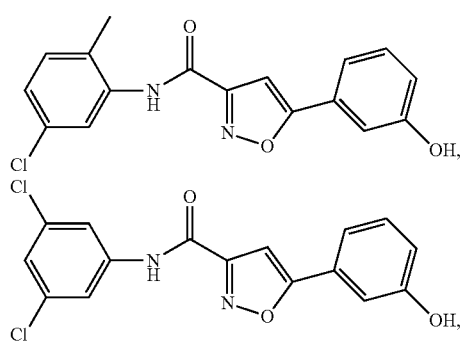

-continued

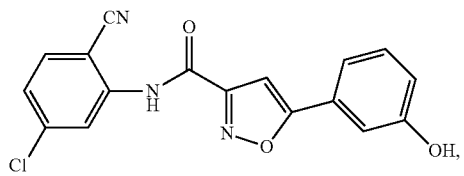
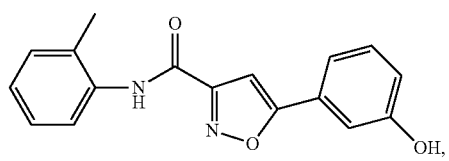
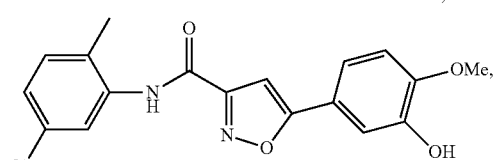
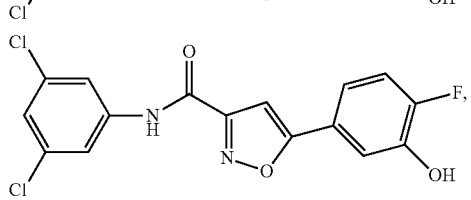
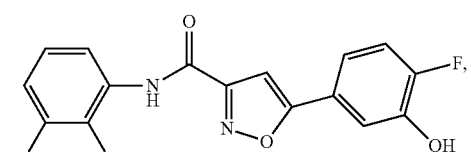
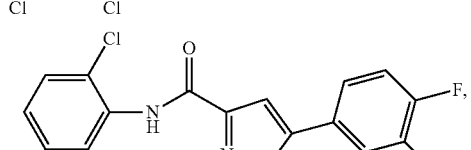
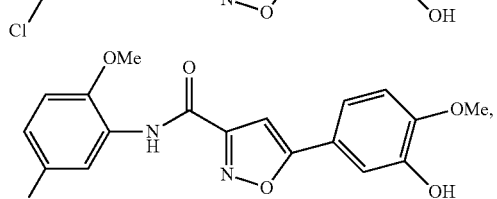
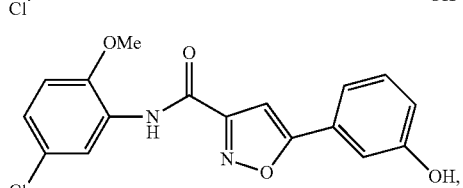
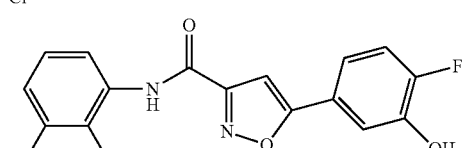
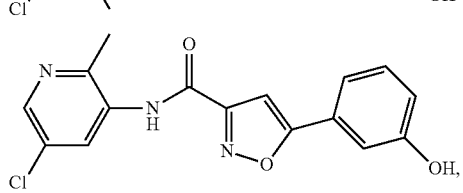

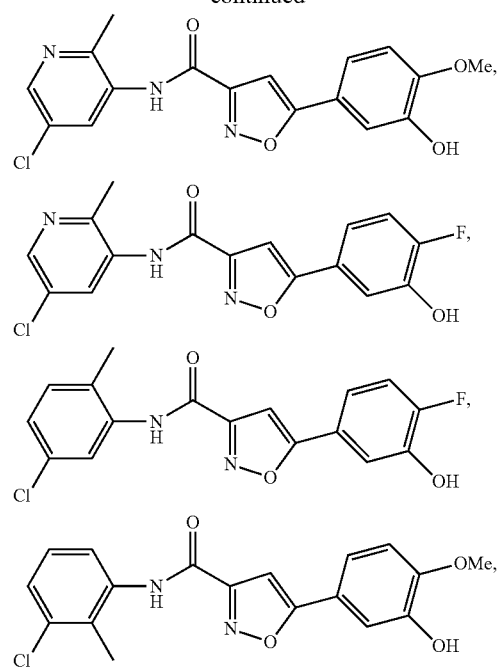
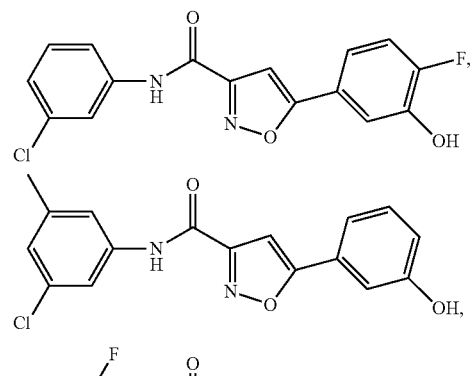
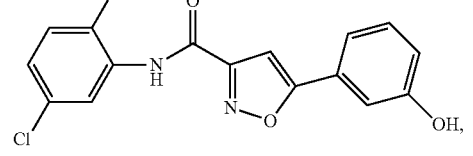
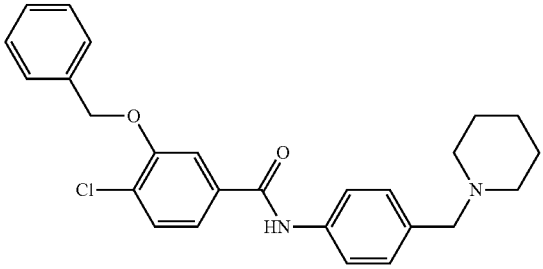
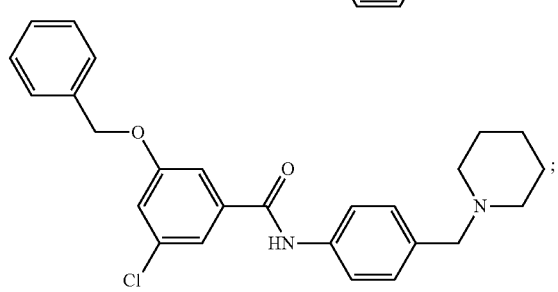
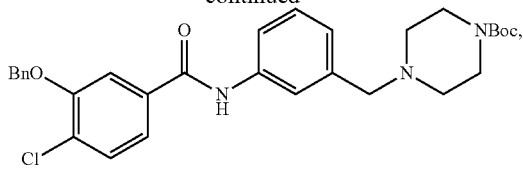
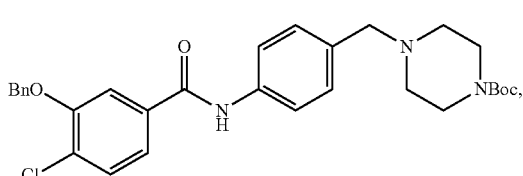
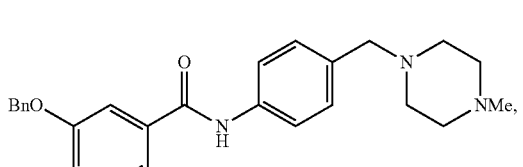
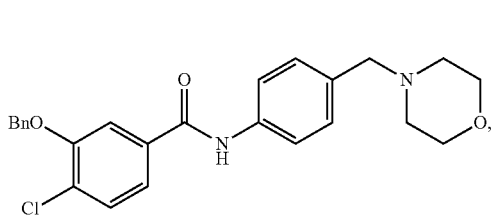
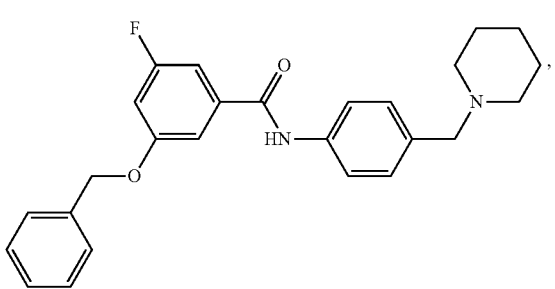
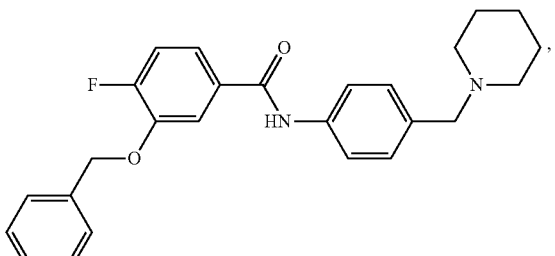
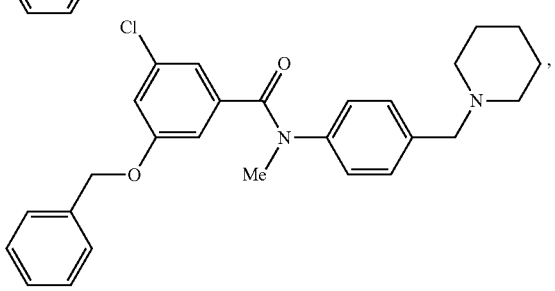

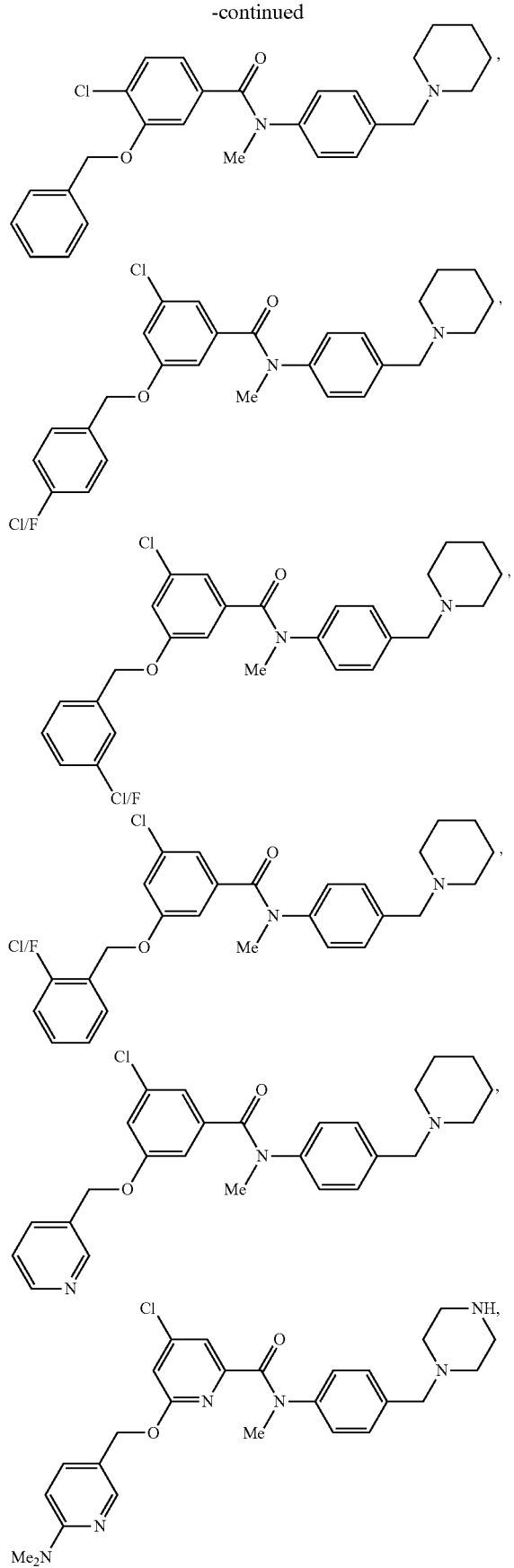
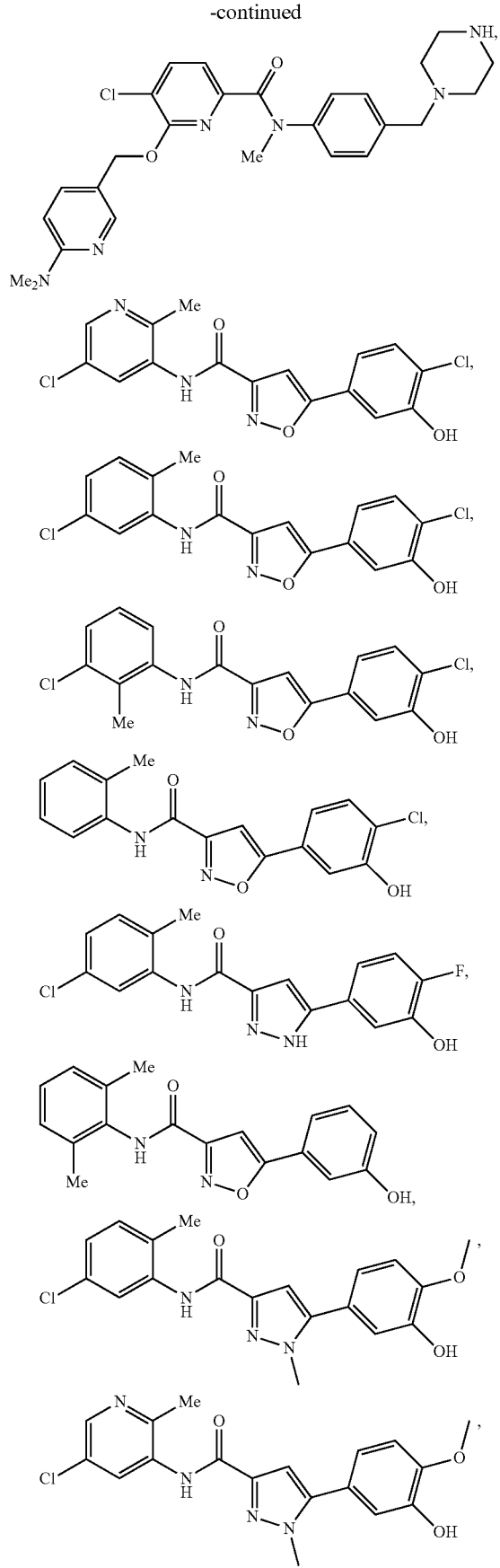

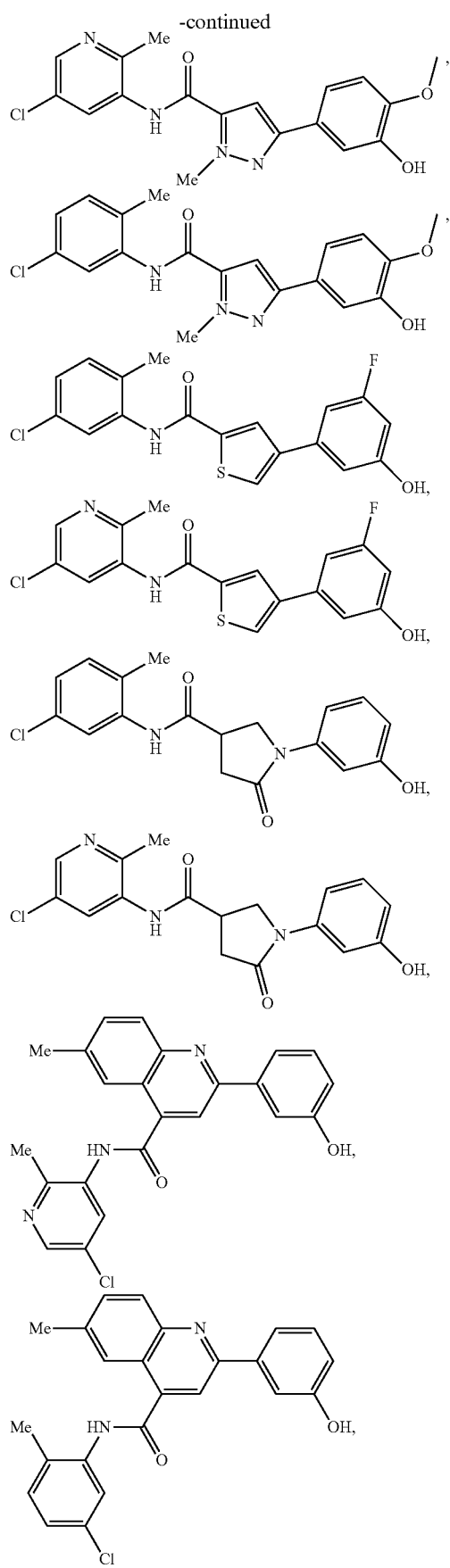
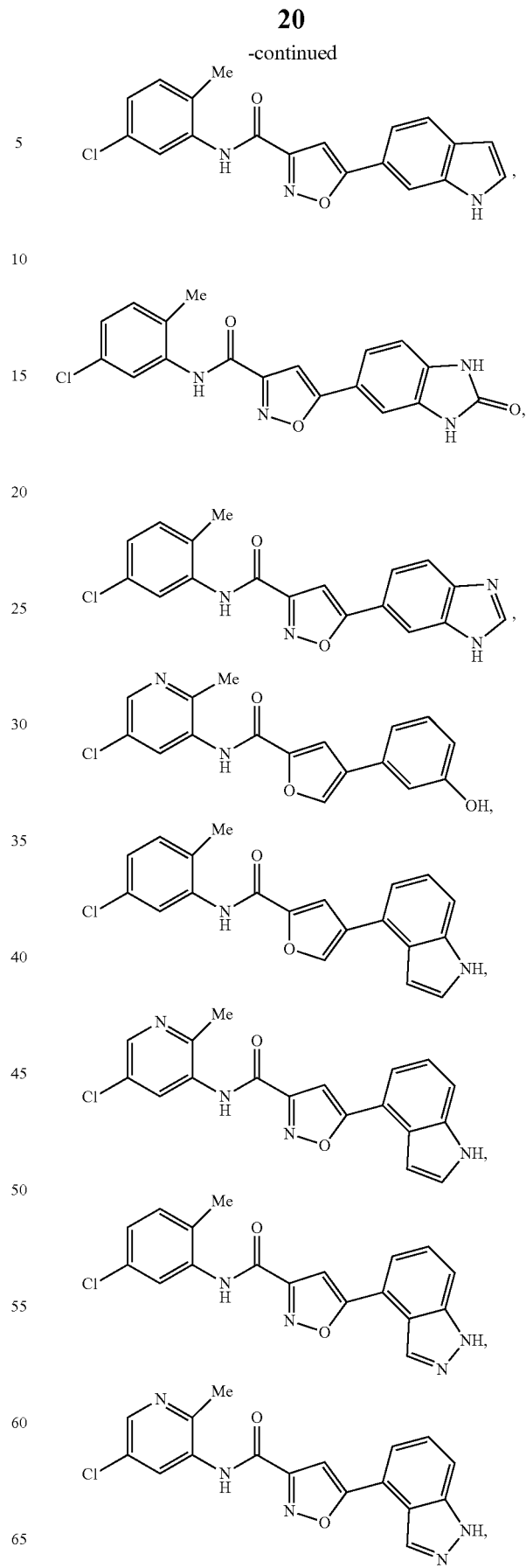

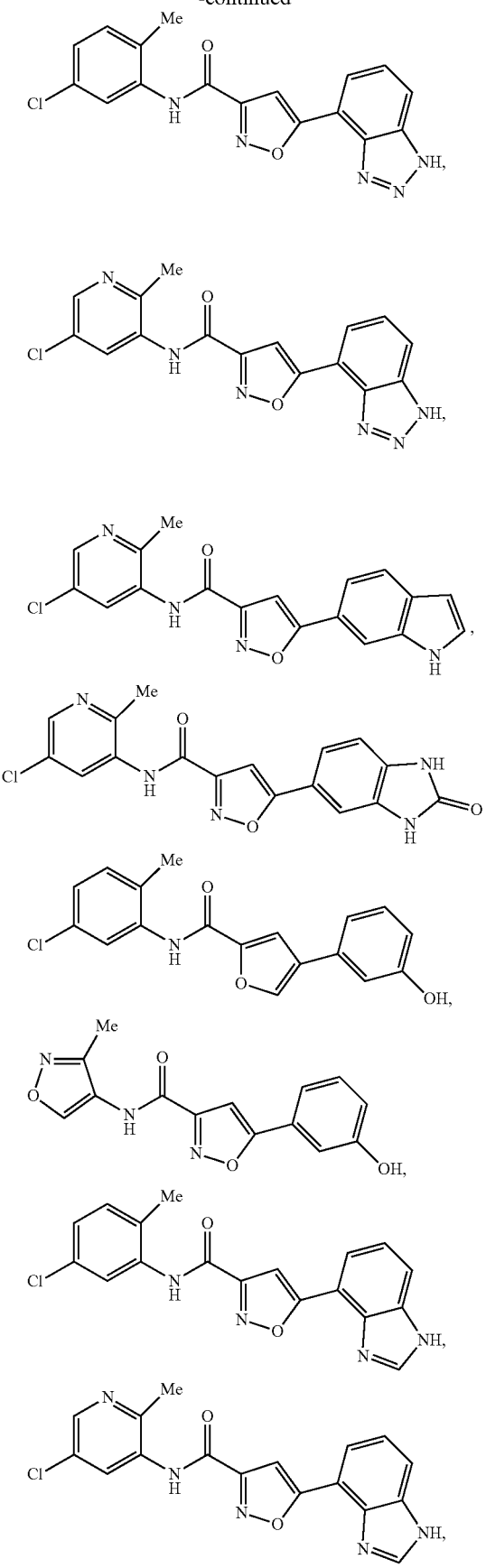
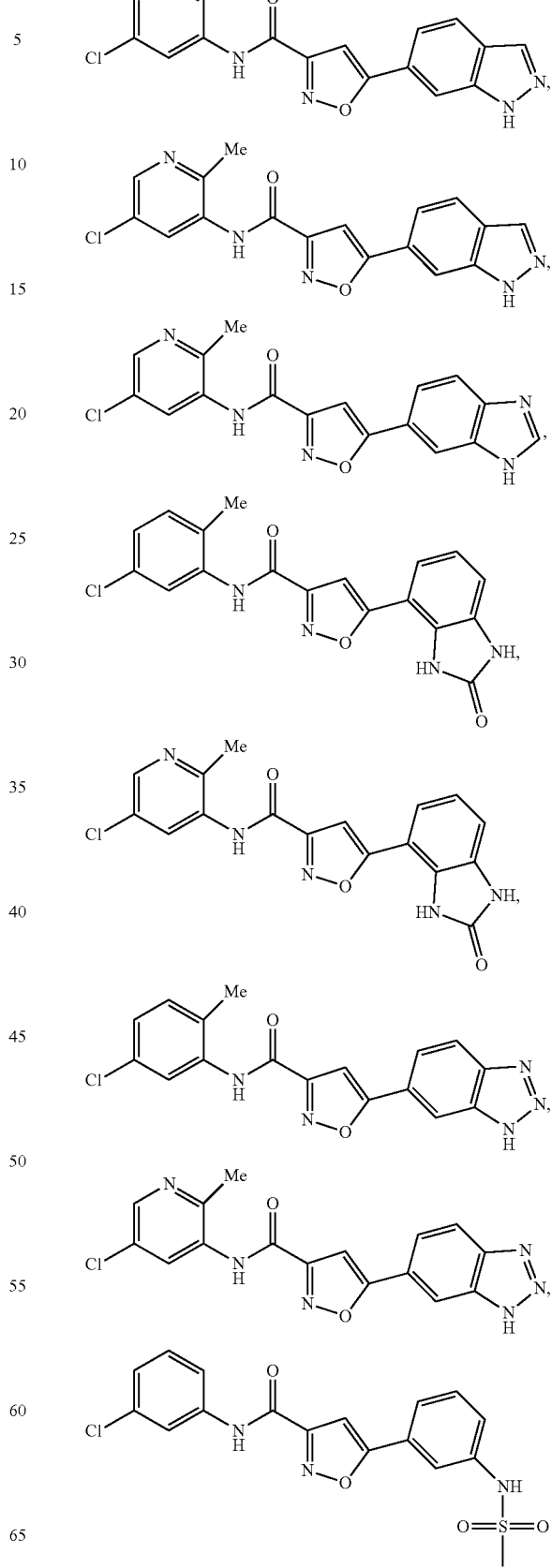

-continued
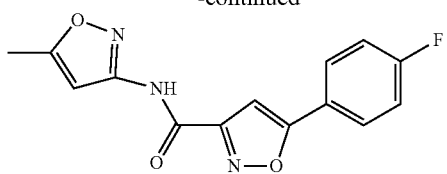
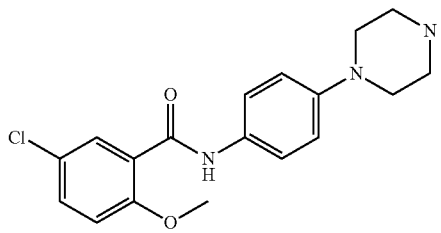
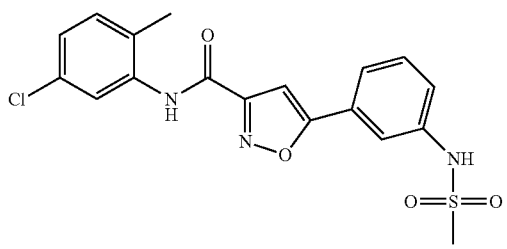
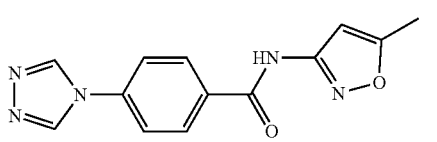
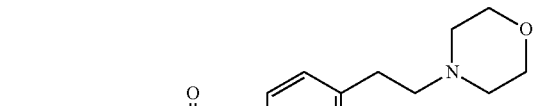
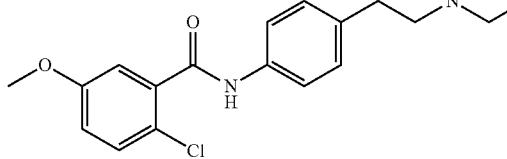
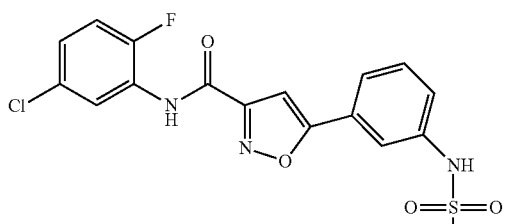
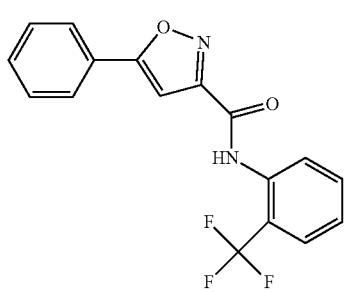
-continued
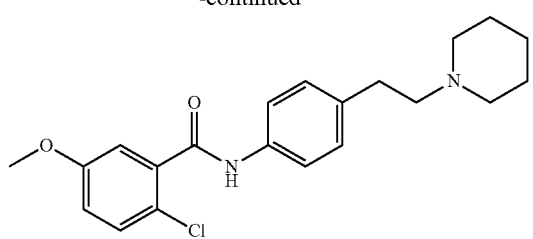
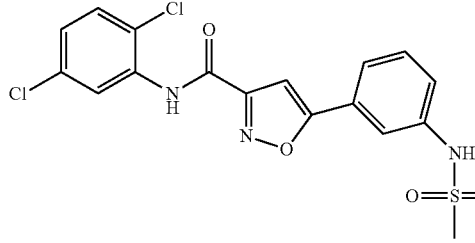
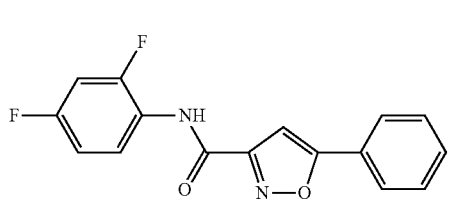
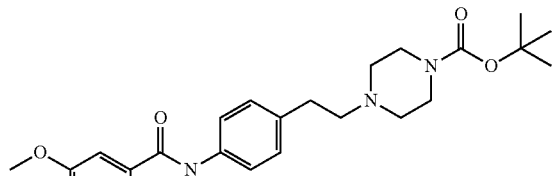
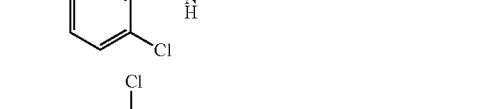
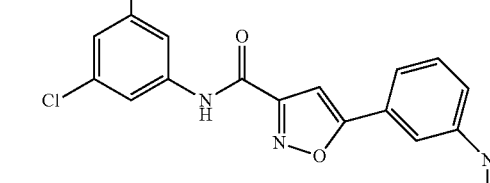
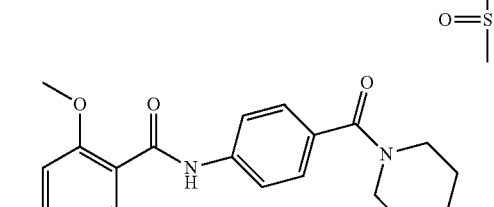
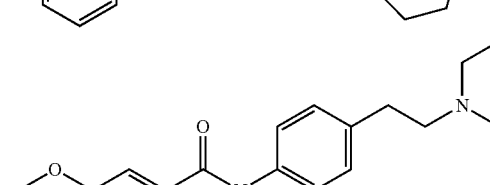
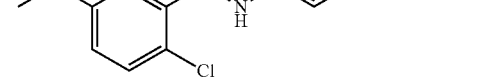

25
-continued
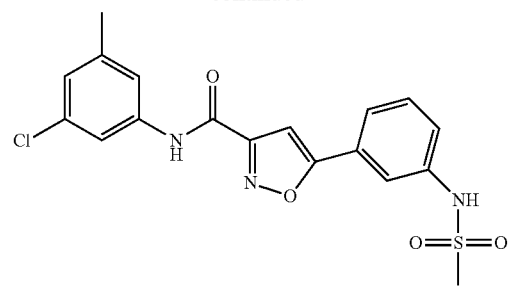
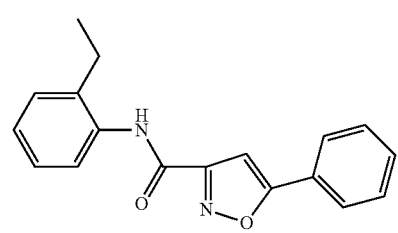
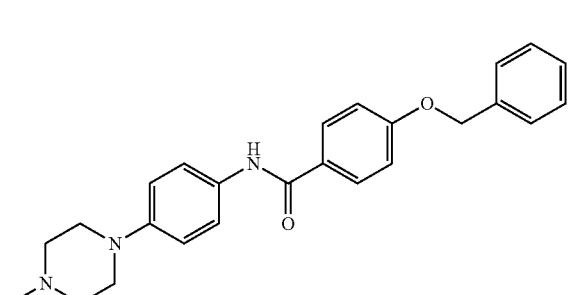
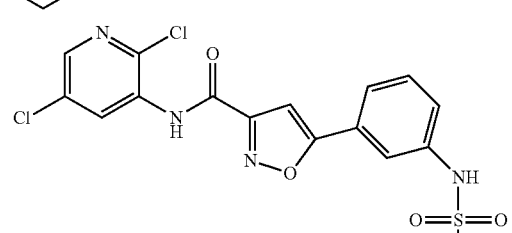
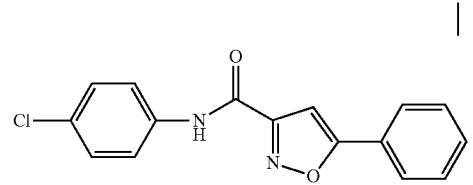
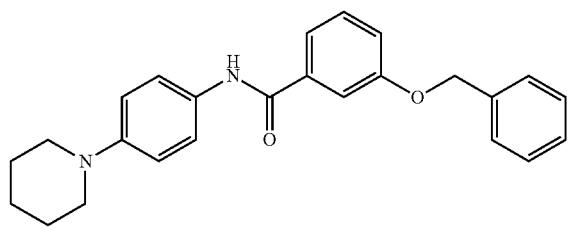
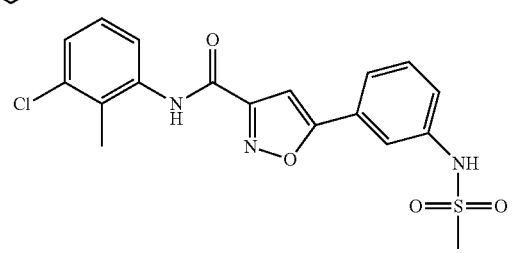
26
-continued
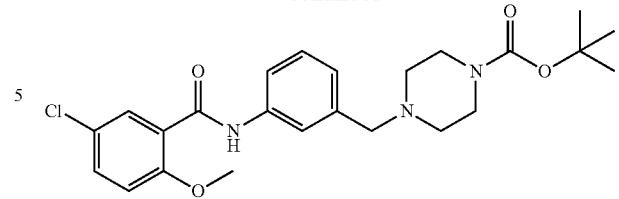
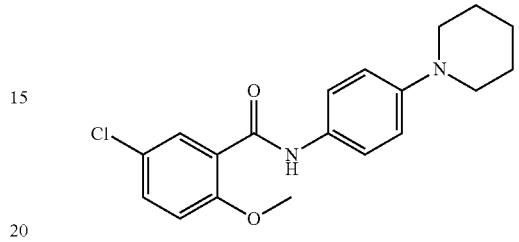
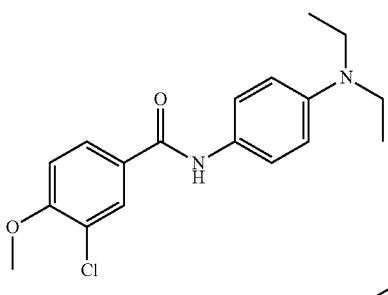
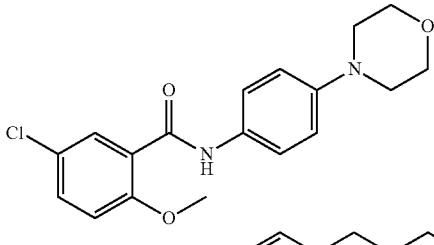
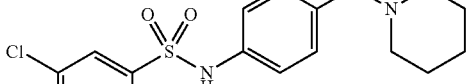
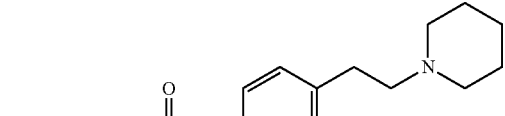
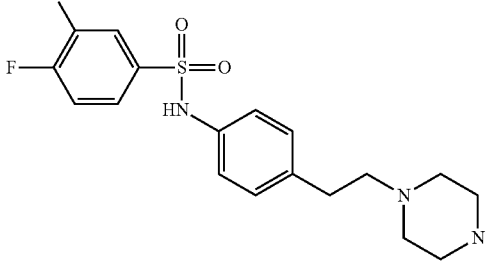

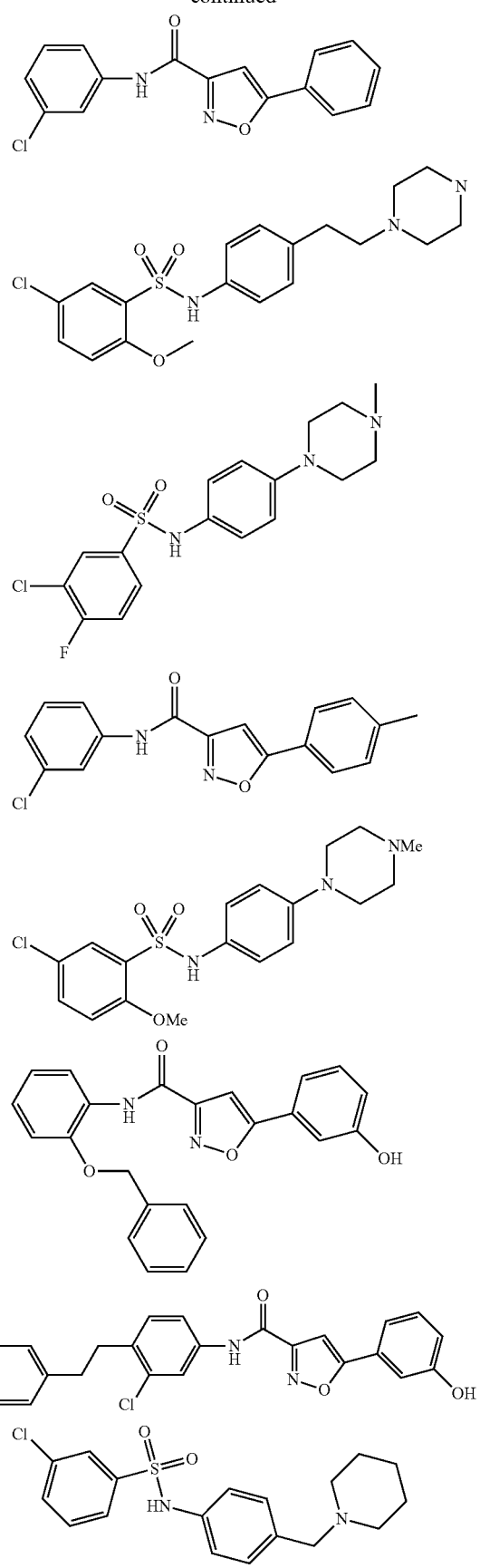
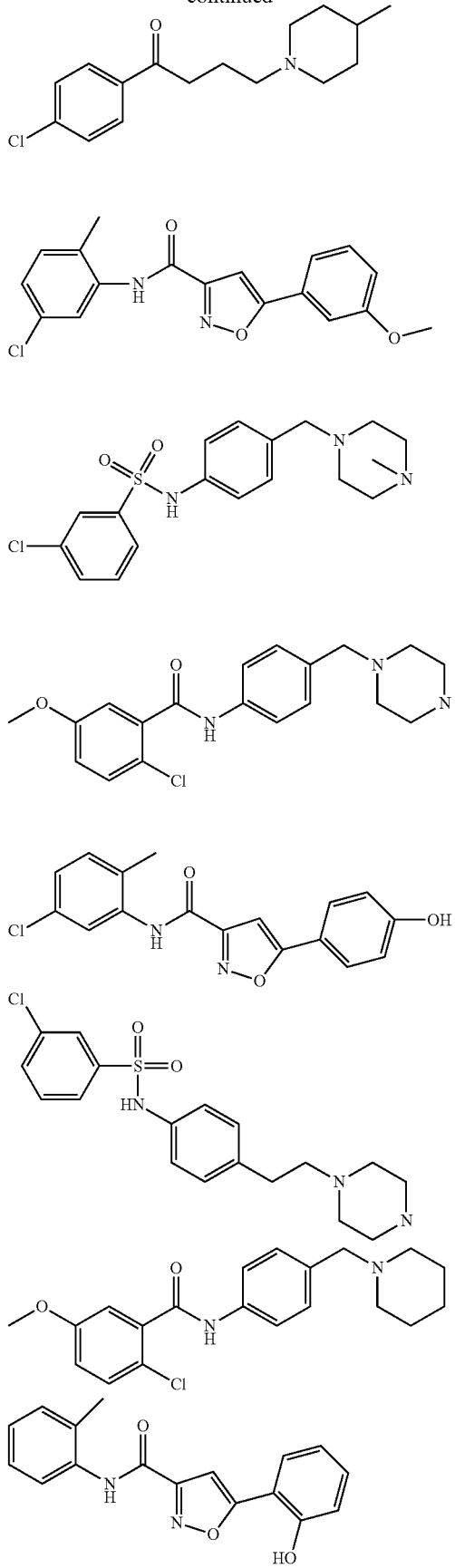

-continued
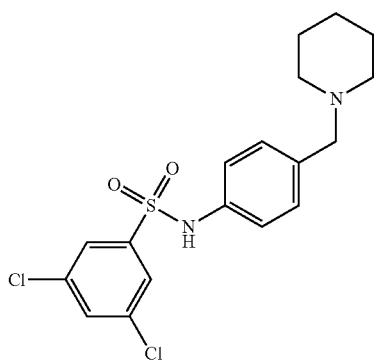
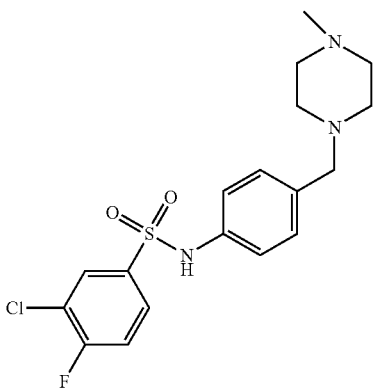
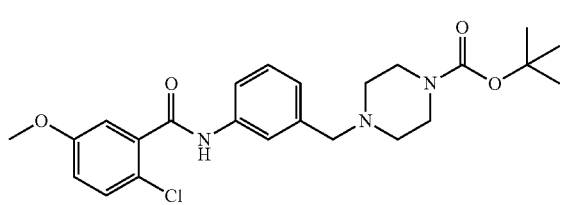
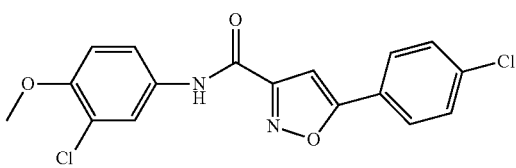
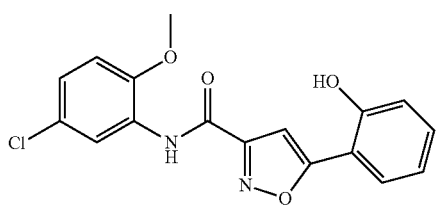
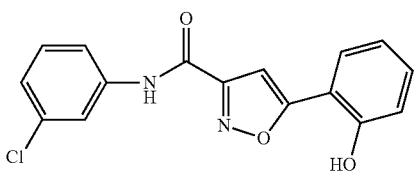
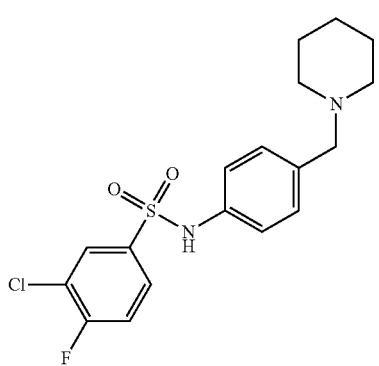
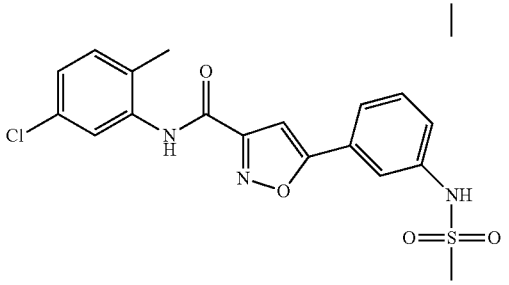
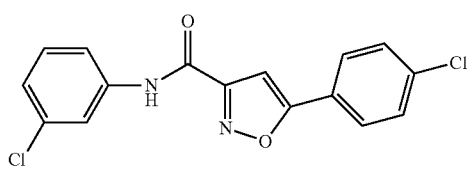
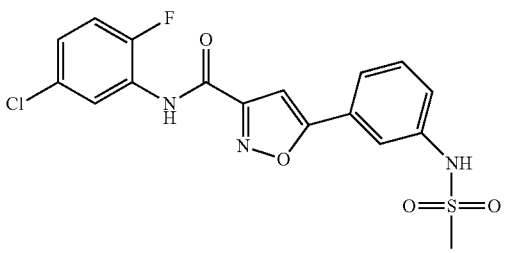
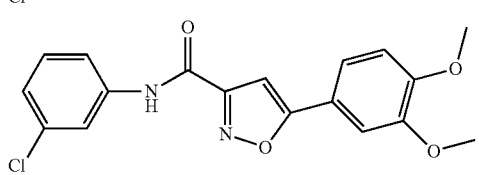
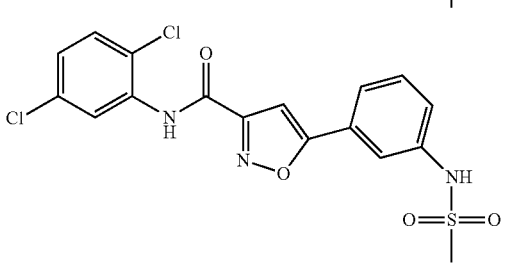

-continued

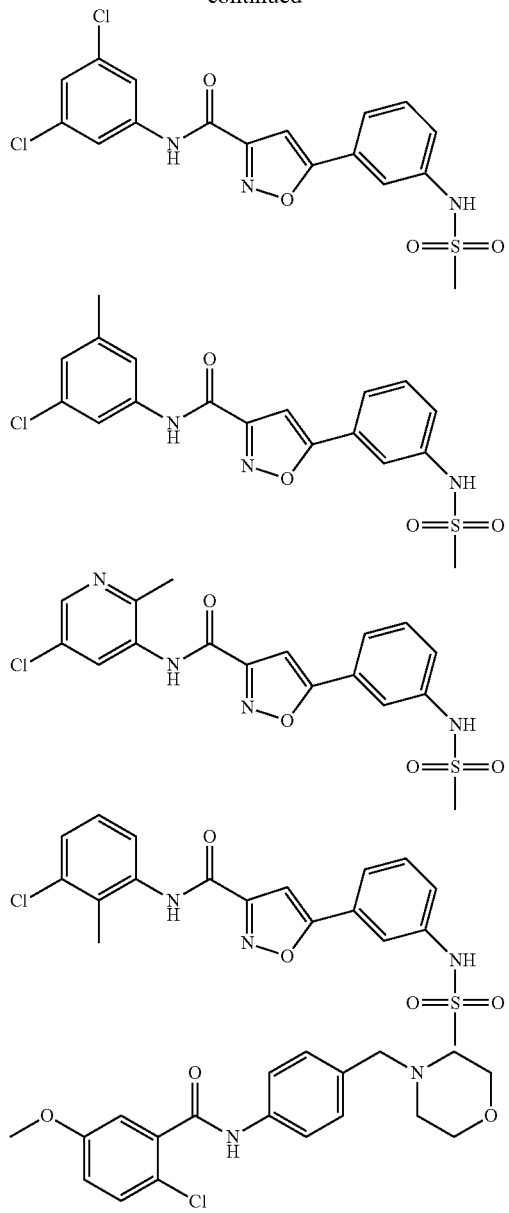

In some embodiments, the present technology is a pharmaceutical composition comprising one or more compounds disclosed herein and a pharmaceutically acceptable excipient. The pharmaceutical compositions of any embodiment herein may be formulated for oral, parenteral, nasal, or topical administration. In any embodiment herein, the pharmaceutical composition may include an effective amount of a compound of any embodiment of the present technology. The compound of the present technology may be present in an amount effective for the treatment of multiple sclerosis, amyotropic lateral sclerosis, ischemic reperfusion injury, Alzheimer's disease, Huntington's disease, Parkinson's disease, insulin-induced hypoglycemia, cerebral ischemia, brain damage from epilepsy or experimental trauma, Bethlem myopathy, pancreatitis, hepatitis (type A, and/or B, and/or C), type II diabetes, diabetic retinopathy, muscular dystrophy, traumatic brain injury, heart infarction, and/or stroke.

"Treating" within the context of the instant technology, means alleviation, in whole or in part, of symptoms associated with a disorder or disease, or slowing, inhibition or halting of further progression or worsening of those symptoms, or prevention or prophylaxis of the disease or disorder in a subject at risk for developing the disease or disorder.

As used herein, an "effective amount" of a compound of the present technology refers to an amount of the compound that alleviates, in whole or in part, symptoms associated with a disorder or disease, or slows or halts of further progression or worsening of those symptoms, or prevents or provides prophylaxis for the disease or disorder in a subject at risk for developing the disease or disorder. Those skilled in the art are readily able to determine an effective amount. For example, one way of assessing an effective amount for a particular disease state is by simply administering a compound of the present technology to a patient in increasing amounts until progression of the disease state is decreased or stopped.

The instant compositions can be formulated for various routes of administration, for example, by oral, parenteral, topical, injection, rectal, nasal, or via implanted reservoir. Parenteral or systemic administration includes, but is not limited to, subcutaneous, intravenous, intraperitoneally, intramuscular, intrathecal, intracranial, and intracerebroventricular injections. The following dosage forms are given by way of example and should not be construed as limiting the instant technology.

For oral, buccal, and sublingual administration, powders, suspensions, granules, tablets, pills, capsules, gelcaps, and caplets are acceptable as solid dosage forms. These can be prepared, for example, by mixing one or more compounds disclosed herein, or pharmaceutically acceptable salts or stereoisomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions, which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is nonvolatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Dosage units for rectal administration may be prepared in the form of suppositories which may contain the composition of matter in a mixture with a neutral fat base, or they may be prepared in the form of gelatin-rectal capsules which contain the active substance in a mixture with a vegetable oil or paraffin oil.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. Formulations for inhalation administration contain as excipients, for example, lactose, polyoxyethylene-9-lauryl ether, glycocholate and deoxycholate. Aqueous and nonaqueous aerosols are typically used for delivery of inventive compounds by inhalation.

Ordinarily, an aqueous aerosol is made by formulating an aqueous solution or suspension of the compound together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins such as serum albumin, sorbitan esters, oleic acid, lecithin, amino acids such as glycine, buffers, salts, sugars or sugar alcohols. Aerosols generally are prepared from isotonic solutions. A nonaqueous suspension (e.g., in a fluorocarbon propellant) can also be used to deliver compounds of the present technology.

Aerosols containing compounds for use according to the present technology are conveniently delivered using an inhaler, atomizer, pressurized pack or a nebulizer and a suitable propellant, e.g., without limitation, pressurized dichlorodifluoromethane, trichlorofluoromethane, dichlorotetrafluoroethane, nitrogen, air, or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch. Delivery of aerosols of the present technology using sonic nebulizers is advantageous because nebulizers minimize exposure of the agent to shear, which can result in degradation of the compound.

For nasal administration, the pharmaceutical formulations and medicaments may be a spray, nasal drops or aerosol containing an appropriate solvent(s) and optionally other compounds such as, but not limited to, stabilizers, antimicrobial agents, antioxidants, pH modifiers, surfactants, bioavailability modifiers and combinations of these. For administration in the form of nasal drops, the compounds may be formulated in oily solutions or as a gel. For administration of nasal aerosol, any suitable propellant may be used including compressed air, nitrogen, carbon dioxide, or a hydrocarbon based low boiling solvent.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant technology.

A therapeutically effective amount of a compound of the present technology may vary depending upon the route of administration and dosage form. Effective amounts of such compounds typically fall in the range of about 0.01 up to about 100 mg/kg/day, or about 0.05 to about 50 mg/kg/day, and more typically in the range of about 0.1 up to 5 mg/kg/day. Typically, the compound or compounds of the instant technology are selected to provide a formulation that exhibits a high therapeutic index. The therapeutic index is the dose ratio between toxic and therapeutic effects and can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

In an aspect, method for inhibiting mtPTP opening is provided where the method includes contacting cells with an effective amount of one or more compounds disclosed herein.

In some embodiments, the present technology is a method for treating a condition mediated at least in part by $[Ca^{2+}]$ dysregulation and/or a reactive oxygen species which method comprises administering to a patient an effective amount of one or more compounds disclosed herein.

In some embodiments, the present technology is a method for treating a condition selected from the group consisting of ischemic reperfusion injury, multiple sclerosis, amyotropic lateral sclerosis, Alzheimer's disease, Huntington's disease, Parkinson's disease, insulin-induced hypoglycemia, cerebral ischemia, brain damage from epilepsy or experimental trauma, Bethlem myopathy, pancreatitis, hepatitis (type A, and/or B, and/or C), diabetic retinopathy, muscular dystrophy, traumatic brain injury, type II diabetes, heart infarction, and stroke, wherein which method comprises administering to a patient an effective amount of one or more compounds disclosed herein.

In any of the above embodiments, it may be the compound of the present technology is not one of the following:

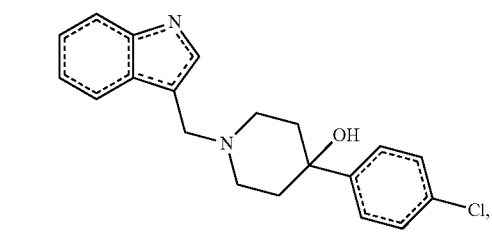

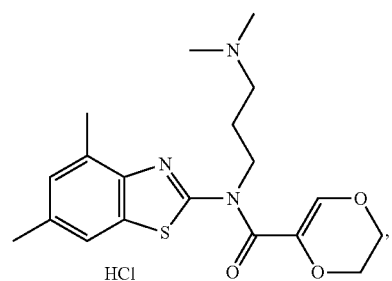

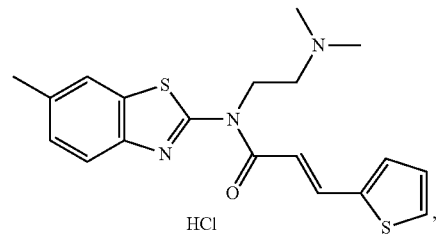

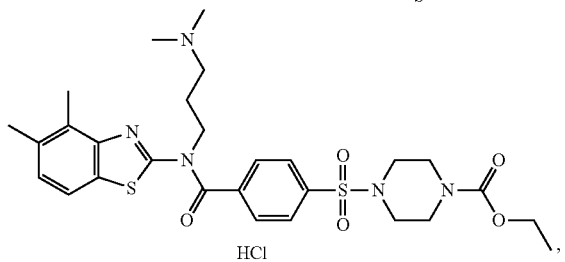

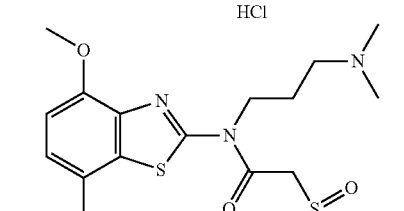

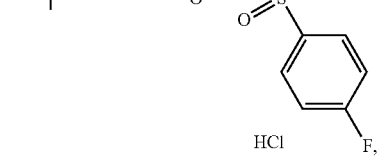

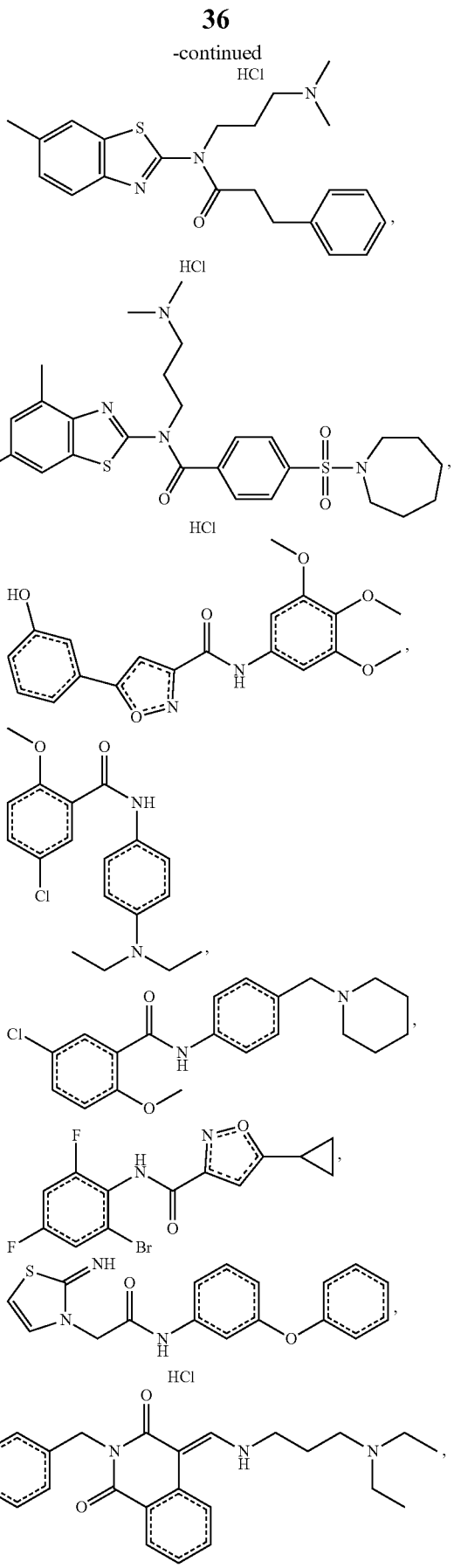

-continued

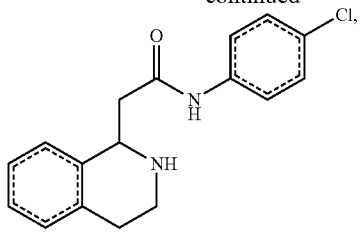

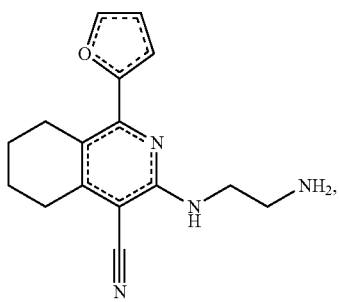

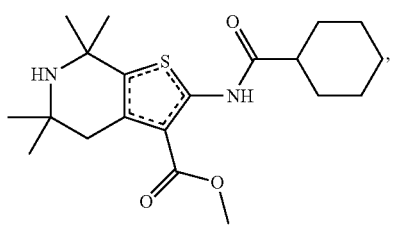

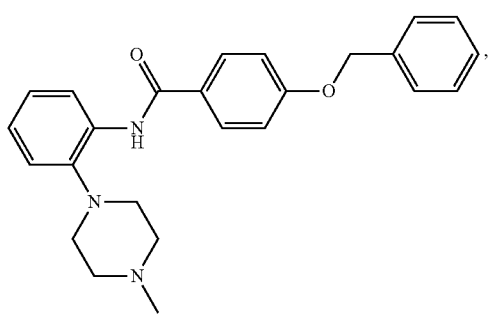

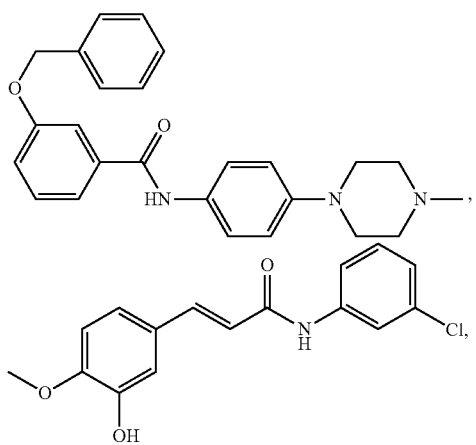

-continued

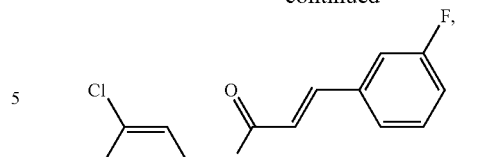

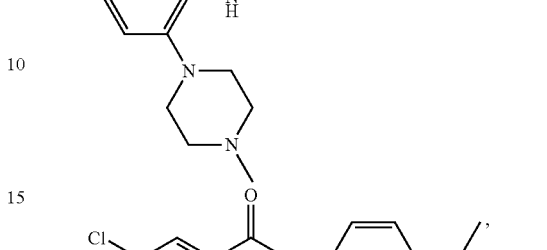

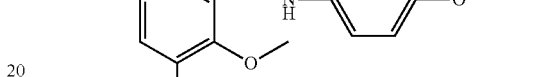

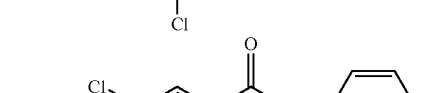

, or

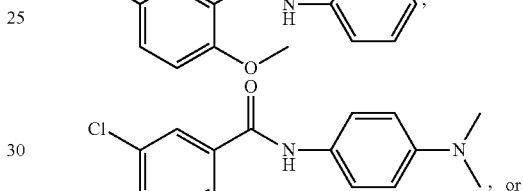

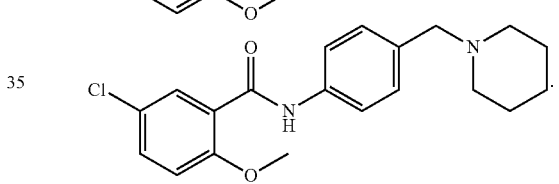

3. Compositions and Methods of the Present Technology

The compounds represented by Formula I, II, IIa, III, IV, and/or V or their tautomers and/or pharmaceutically acceptable salts thereof may effectively inhibit mtPTP and treat conditions mediated at least in part by [Ca$^{2+}$] dysregulation and/or a reactive oxygen species. In one aspect, the present technology provides pharmaceutical compositions comprising one or more compounds of Formula I, II, IIa, III, IV, and/or V and a pharmaceutically acceptable excipient. In another aspect of the present technology, the present technology provides a method for inhibiting mtPTP and/or a method for treating a disease mediated at least in part by accumulating by [Ca$^{2+}$] dysregulation and/or a reactive oxygen species with an effective amount of one or more compound of Formula I, II, IIa, III, IV, and/or V as provided herein. The compounds of the present technology are useful in inhibiting mtPTP and treating disorders related to [Ca$^{2+}$] dysregulation and/or oxidative stress.

In one of its method aspects, the present technology is directed to a method for inhibiting mtPTP which method comprises contacting cells (including neurons/microglia/invading macrophages) with an effective amount of one or more compound of Formula I, II, IIa, III, IV, and/or V as described herein.

In another of its method aspects, the present technology is directed to a method for treating a disease mediated at least in part by [$Ca^{2+}$] dysregulation and/or a reactive oxygen species, which method comprises administering to a patient an effective amount of one or more compounds of Formula I, II, IIa, III, IV, and/or V or a pharmaceutical composition comprising a pharmaceutically acceptable excipient and one or more compound of Formula I, II, IIa, III, IV, and/or V as described herein.

Diseases mediated at least in part by [$Ca^{2+}$] dysregulation and/or a reactive oxygen species include those selected from the group consisting of Huntington's disease and other polyglutamine disorders, Alzheimer's disease, Huntington's disease, Parkinson's disease, insulin-induced hypoglycemia, cerebral ischemia, brain damage from epilepsy or experimental trauma, Bethlem myopathy, pancreatitis, hepatitis, diabetic retinopathy, ischemic reperfusion injury, multiple sclerosis, amyotropic lateral sclerosis, muscular dystrophy, traumatic brain injury, type II diabetes, heart infarction, stroke, epilepsy, consequences of stroke, cerebral ischemia, hypoxia, multi-infarct dementia, consequences of cerebral trauma or damage, damage to the spinal cord, AIDS-dementia complex, viral or bacterial meningitis, general central nervous system (CNS) infections such as viral, bacterial or parasites, for example, poliomyelitis, Lyme disease (*Borrelia burgdorferi* infection) and malaria, cancers with cerebral localization, Tourette's syndrome, hepatic encephalopathy, systemic lupus, analgesia and opiate withdrawal symptoms, feeding behavior, schizophrenia, chronic anxiety, depressive disorders, disorders of the developing or aged brain, diseases of addiction, diabetes, and complications thereof.

The compounds of the present technology are useful in the diagnosis and treatment of a variety of human diseases including neurodegenerative and neurological disorders, consequences of stroke and/or cerebral ischemia, hypoxia, multi-infarct dementia, consequences of trauma and damages to the cerebrum or spinal cord, autoimmune disease, and psychiatric illness. For example, the compounds of the present technology are particularly useful in treating neurodegenerative disorders such as Huntington's disease and other polyglutamine disorders, ischemic reperfusion injury, multiple sclerosis, amyotropic lateral sclerosis, Alzheimer's disease, Huntington's disease, Parkinson's disease, insulin-induced hypoglycemia, cerebral ischemia, brain damage from epilepsy or experimental trauma, Bethlem myopathy, pancreatitis, hepatitis, diabetic retinopathy, muscular dystrophy, traumatic brain injury, type II diabetes, heart infarction, stroke, high-pressure neurological syndrome, dystonia, olivopontocerebellar atrophy, frontotemporal dementia, amyotrophic lateral sclerosis, multiple sclerosis, epilepsy, consequences of stroke, cerebral ischemia, hypoxia, multi-infarct dementia, consequences of cerebral trauma or damage, damage to the spinal cord, AIDS-dementia complex, viral or bacterial meningitis, general central nervous system (CNS) infections such as viral, bacterial or parasites, for example, poliomyelitis, Lyme disease (*Borrelia burgdorferi* infection) and malaria, cancers with cerebral localization, Tourette's syndrome, hepatic encephalopathy, systemic lupus, analgesia and opiate withdrawal symptoms, feeding behavior, schizophrenia, chronic anxiety, depressive disorders, disorders of the developing or aged brain, diseases of addiction, all peripheral indications such as diabetes, and complications thereof.

Compounds of the present technology are shown or contemplated to have improved safety and potency, such as the potency of inhibiting mtPTP at low nanomolar concentrations. In some embodiments, the compounds have little or no neuroleptic activity.

The amount of active compound administered will vary depending upon the disease treated, the mammalian species, and the particular mode of administration, etc. Suitable doses for the compounds of the present technology can be, for example, between 0.1 mg to about 1000 mg, between 1 mg to about 500 mg, between 1 mg to about 300 mg, or between 1 mg to about 100 mg per day. Such doses can be administered once a day or more than once a day, for example 2, 3, 4, 5 or 6 times a day, but preferably 1 or 2 times per day. In some embodiments, the total dosage for a 70 kg adult is in the range of 0.001 to about 15 mg per kg weight of subject per administration or 0.01 to about 1.5 mg per kg weight of subject per administration, and such therapy can extend for a number of days, a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

4. General Synthetic Methods

The compounds of the present technology may be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, *Protecting Groups in Organic Synthesis*, Third Edition, Wiley, New York, 1999, and references cited therein.

If the compounds of the present technology contain one or more chiral centers, such compounds can be prepared or isolated as pure stereoisomers, i.e., as individual enantiomers or diastereomers, or as stereoisomer-enriched mixtures. All such stereoisomers (and enriched mixtures) are included within the scope of the present technology, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka- Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

Synthesis of Representative Compounds of the Present Technology

In one general embodiment, the method involves reacting an appropriate aniline starting material with an electrophilic partner such as a carboxylic acid or the corresponding acyl halide in order to make a benzamide or benzene sulfonamide. It is appreciated that the nucleophilic component of the aniline preferentially adds to the carbonyl of the electrophilic component. Additionally, isoxazoline compounds are made by cyclization after condensing an appropriate diketo-compound with hydroxyl amine. The isolated adduct can then be further functionalized.

In another general embodiment, the method involves reacting an appropriately functionalized aniline or diketo-compound, as synthesized from above, with a partner. It is further appreciated that the partner selectively reacts at one functional group of the aniline or diketo-compound. Thus, the partner should not be added under any reaction conditions that might react with any other functionality.

For example, the compounds of general Formula I, II, IIa, III, IV, and/or V can be prepared according to representative Scheme 1:

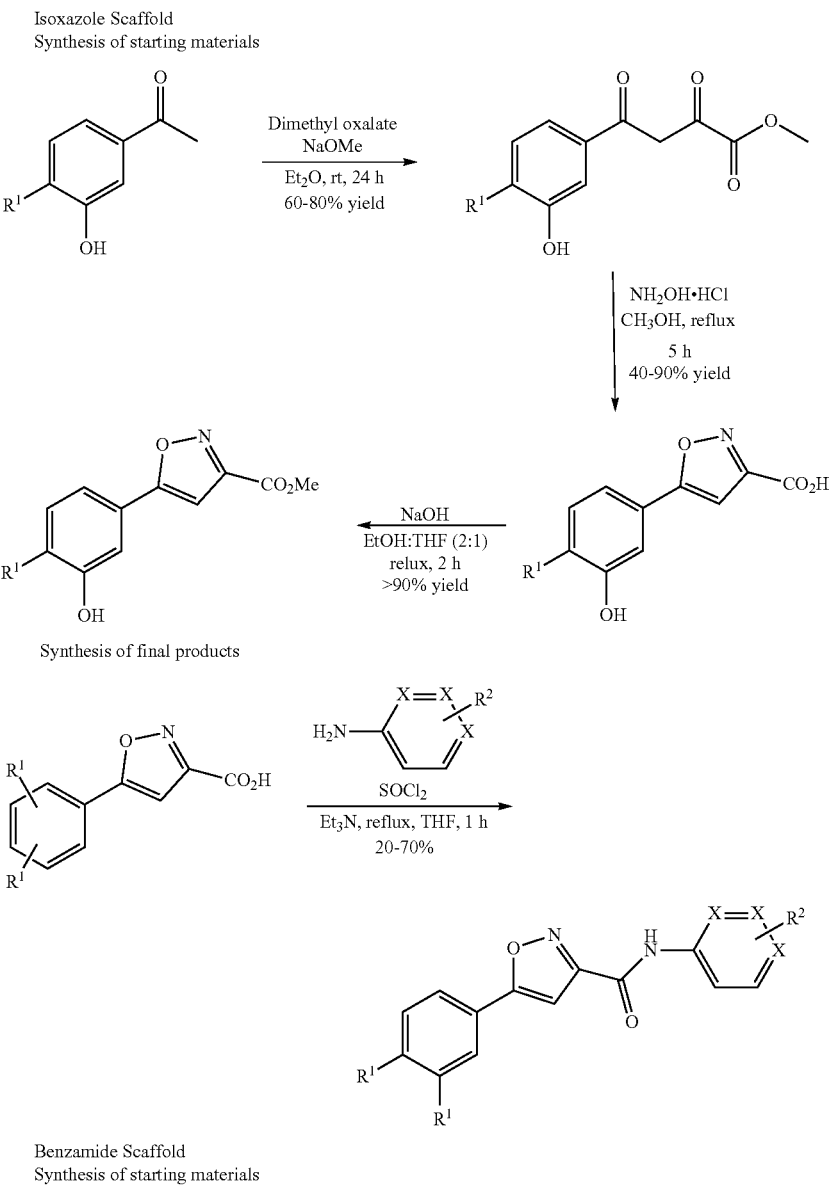

-continued

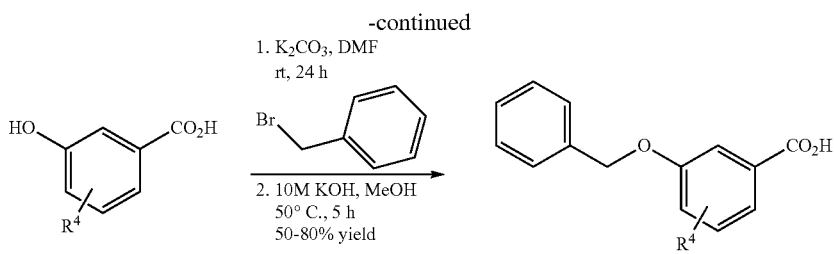

Synthesis of final products (amide)

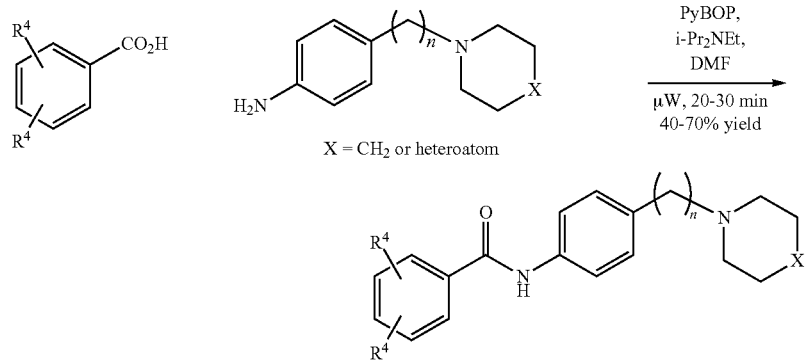

Synthesis of final products (sulfonamide)

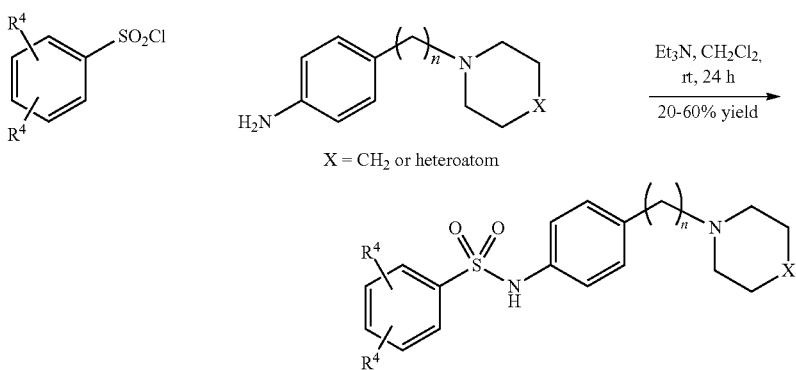

Amino, keto, thio, hydroxyl, and any other necessary protecting groups and their methods of deprotection are known in the art, such as those described in T. W. Greene and P. G. M. Wuts, *Protecting Groups in Organic Synthesis*, Third Edition, Wiley, New York, 1999. When Prt is hydrogen, the deprotection step can be omitted.

5. Administration and Pharmaceutical Composition

The present technology provides compounds possessing mtPTP inhibitory activity and, accordingly, are useful in treating disorders mediated by (or at least in part by) [$Ca^{2+}$] dysregulation and/or the accumulation of by a reactive oxygen species. Such diseases include, for example, Huntington's disease and other polyglutamine disorders, ischemic reperfusion injury, multiple sclerosis, amyotropic lateral sclerosis, Alzheimer's disease, Huntington's disease, Parkinson's disease, insulin-induced hypoglycaemia, cerebral ischemia, brain damage from epilepsy or experimental trauma, Bethlem myopathy, pancreatitis, hepatitis, diabetic retinopathy, muscular dystrophy, traumatic brain injury, type II diabetes, heart infarction, stroke, high-pressure neurological syndrome, dystonia, olivopontocerebellar atrophy, frontotemporal dementia, amyotrophic lateral sclerosis, multiple sclerosis, epilepsy, consequences of stroke, cerebral ischemia, hypoxia, multi-infarct dementia, consequences of cerebral trauma or damage, damage to the spinal cord, AIDS-dementia complex, viral or bacterial meningitis, general central nervous system (CNS) infections such as viral, bacterial or parasites, for example, poliomyelitis, Lyme disease (*Borrelia burgdorferi* infection) and malaria, cancers with cerebral localization, Tourette's syndrome, hepatic encephalopathy, systemic lupus, analgesia and opiate withdrawal symptoms, feeding behaviour, schizophrenia, chronic anxiety, depressive disorders, disorders of the developing or aged brain, diabetes, and complications thereof.

In general, the compounds of the present technology will be administered in a therapeutically effective amount by any of the accepted modes of administration for agents that serve similar utilities. The actual amount of the compound of the present technology, i.e., the active ingredient, will depend upon numerous factors such as the severity of the disease to be treated, the age and relative health of the subject, the potency of the compound used, the route and form of administration, and other factors well known to the skilled artisan. The drug can be administered at least once a day, preferably once or twice a day.

An effective amount of such agents can readily be determined by routine experimentation, as can the most effective and convenient route of administration, and the most appropriate formulation. Various formulations and drug delivery systems are available in the art. See, e.g., Gennaro, A. R., ed. (1995) Remington's Pharmaceutical Sciences, 18th ed., Mack Publishing Co.

A therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

An effective amount or a therapeutically effective amount or dose of an agent, e.g., a compound of the present technology, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is therapeutic index, which can be expressed as the ratio LD50/ED50. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages particularly fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of agent or composition administered may be dependent on a variety of factors, including the sex, age, and weight of the subject being treated, the severity of the affliction, the manner of administration, and the judgment of the prescribing physician.

The present technology is not limited to any particular composition or pharmaceutical carrier, as such may vary. In general, compounds of the present technology will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of the present technology is inhalation.

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI), and dry powder inhalers (DPI). Nebulizer devices produce a stream of high velocity air that causes therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, therapeutic agent is formulated with an excipient such as lactose. A measured amount of therapeutic agent is stored in a capsule form and is dispensed with each actuation.

Pharmaceutical dosage forms of a compound of the present technology may be manufactured by any of the methods well-known in the art, such as, for example, by conventional mixing, sieving, dissolving, melting, granulating, dragée-making, tableting, suspending, extruding, spray-drying, levigating, emulsifying, (nano/micro-) encapsulating, entrapping, or lyophilization processes. As noted above, the compositions of the present technology can include one or more physiologically acceptable inactive ingredients that facilitate processing of active molecules into preparations for pharmaceutical use.

Pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, a compound of the present technology in combination with at least one pharmaceutically acceptable excipient. Acceptable excipients are non-toxic, aid administration, and do not adversely affect therapeutic benefit of the claimed compounds. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of the present technology in aerosol form. Gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The present compositions may, if desired, be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compositions comprising a compound of the present technology formulated in a compatible pharmaceutical carrier may also be prepared, placed in an appropriate container, and labeled for treatment of an indicated condition.

The amount of the compound in a formulation can vary within the full range employed by those skilled in the art. Typically, the formulation will contain, on a weight percent (wt %) basis, from about 0.01-99.99 wt % of a compound of the present technology based on the total formulation, with the balance being one or more suitable pharmaceutical excipients. Preferably, the compound is present at a level of about 1-80 wt %. Representative pharmaceutical formulations are described below.

FORMULATION EXAMPLES

The following are representative pharmaceutical formulations including a compound of Formula I, II, IIa, III, IV, and/or V.

Formulation Example 1—Tablet Formulation

The following ingredients are mixed intimately and pressed into single scored tablets.

| Ingredient | Quantity per tablet, mg |
| --- | --- |
| compound of the present technology | 400 |
| cornstarch | 50 |
| croscarmellose sodium | 25 |
| lactose | 120 |
| magnesium stearate | 5 |

Formulation Example 2—Capsule Formulation

The following ingredients are mixed intimately and loaded into a hard-shell gelatin capsule.

| Ingredient | Quantity per capsule, mg |
| --- | --- |
| compound of the present technology | 200 |
| lactose, spray-dried | 148 |
| magnesium stearate | 2 |

Formulation Example 3—Suspension Formulation

The following ingredients are mixed to form a suspension for oral administration.

| Ingredient | Amount |
| --- | --- |
| compound of the present technology | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |
| colorings | 0.5 mg |
| distilled water | q.s. to 100 mL |

Formulation Example 4—Injectable Formulation

The following ingredients are mixed to form an injectable formulation.

| Ingredient | Amount |
| --- | --- |
| compound of the present technology | 0.2 mg-20 mg |
| sodium acetate buffer solution, 0.4M | 2.0 mL |
| HCl (1N) or NaOH (1N) | q.s. to suitable pH |
| water (distilled, sterile) | q.s. to 20 mL |

Formulation Example 5—Suppository Formulation

A suppository of total weight 2.5 g is prepared by mixing the compound of the present technology with Witepsol® H-15 (triglycerides of saturated vegetable fatty acid; Riches-Nelson, Inc., New York), and has the following composition:

| Ingredient | Amount |
| --- | --- |
| Compound of the present technology | 500 mg |
| Witepsol ® H-15 | balance |

The following synthetic and biological examples are offered to illustrate the present technology and are not to be construed in any way as limiting the scope of the present technology. Unless otherwise stated, all temperatures are in degree Celsius.

EXAMPLES

The present technology is further understood by reference to the following examples, which are intended to be purely exemplary of the present technology. The present technology is not limited in scope by the exemplified embodiments, which are intended as illustrations of single aspects of the present technology only. Any methods that are functionally equivalent are within the scope of the present technology. Various modifications of the present technology in addition to those described herein will become apparent to those skilled in the art from the foregoing description and accompanying figures. Such modifications fall within the scope of the appended claims.

In the examples below, the following abbreviations have the following meanings. If an abbreviation is not defined, it has its generally accepted meaning.

aq.=aqueous
CaCl$_2$=calcium chloride
LC-MS=liquid chromatography-mass spectrometry
MS=mass spectrometry
THF=tetrahydrofuran
NaHCO$_3$=sodium bicarbonate
DIPEA=diisopropylethylamine
MS=mass spectrometry
NaH=sodium hydride
o/n=overnight
HATU=1-[Bis(dimethylamino)methylene]-1H-1,2,3-triazolo[4,5-b]pyridinium 3-oxid hexafluorophosphate
r.t.=room temperature
LAH=lithium aluminum hydride
DCM=dichloromethane
DMF=dimethylformamide
DMSO=dimethyl sulfoxide
equiv.=equivalent
EtOAc=ethyl acetate
EtOH=ethanol
g=gram
h=hours
HCl=hydrochloric acid
HCHO=formaldehyde
HPLC=high-performance liquid chromatography
HOAc=acetic acid
M=molar
m-CPBA=m-chloroperoxybenzoic acid
MeOH=methanol
mg=milligrams
mL=milliliters
mmol=millimols
mp=melting point
m/z=mass to charge ratio
NaCl=sodium chloride
Na$_2$CO$_3$=sodium carbonate
NMR=nuclear magnetic resonance
NaOH=sodium hydroxide
Na$_2$SO$_4$=sodium sulfate
TLC=thin layer chromatography
UV=ultraviolet
wt %=weight percent
μM=micromolar

GENERAL EXPERIMENTAL DETAILS

Purity of all final compounds was confirmed by HPLC/MS analysis and determined to be ≥90%. $^1$H and $^{13}$C NMR spectra were recorded on a Bruker AM 400 spectrometer (operating at 400 and 101 MHz respectively) or a Bruker AVIII spectrometer (operating at 500 and 126 MHz respectively) in CDCl$_3$ (residual internal standard CHCl$_3$=δ 7.26), DMSO-d$_6$ (residual internal standard CD$_3$SOCD$_2$H=δ 2.50), or acetone-d$_6$ (residual internal standard CD$_3$COCD$_2$H=δ 2.05). The chemical shifts (δ) reported are given in parts per million (ppm) and the coupling constants (J) are in Hertz (Hz). The spin multiplicities are reported as s=singlet, bs=broad singlet, bm=broad multiplet=doublet, t=triplet, q=quartet, p=pentuplet, dd=doublet of doublet, ddd=doublet of doublet of doublet, dt=doublet of triplet, td=triplet of doublet, tt=triplet of triplet, and m=multiplet.

HPLC/MS analysis was carried out with gradient elution (5% CH$_3$CN to 100% CH$_3$CN) on an Agilent 1200 RRLC with a photodiode array UV detector and an Agilent 6224 TOF mass spectrometer (also used to produce high resolution mass spectra). Automated preparative RP HPLC purification was carried out by Mass Directed Fractionation with gradient elution (a narrow CH$_3$CN gradient was chosen based on the retention time of the target from LCMS analysis of the crude sample) on an Agilent 1200 instrument with photodiode array detector, an Agilent 6120 quadrupole mass spectrometer, and a HTPAL LEAP autosampler. Fractions were triggered using an MS and UV threshold determined by HPLC/MS analysis of the crude sample. One of two column/mobile phase conditions were chosen for both analysis and purification to promote the targets neutral state: 0.02% formic acid with Waters Atlantis T3 5 um, 19×150 mm (Prep scale), Waters Atlantis T3 1.7 um, 2.1×50 mm (Analytical Scale); pH 9.8 NH$_4$OH with Waters XBridge C18 5 um, 19×150 mm (Prep scale), Waters BEH C-18 1.7 um, 2.1×50 mm (Analytical Scale). Medium pressure liquid chromatography (MPLC) was performed on a Teledyne Icso CombiFlash Rf purification system using gradient elution through standard RediSep Rf columns. Microwave irradiated reactions were carried out using a Biotage Initiator Classic synthesizer.

The following are experimental reactions used to synthesize intermediates and the final isoxazole and benzamide compounds.

General Procedure (Isoxazole Amide) 1:

To a solution of isoxazole carboxylic acid (0.390 mmol, 1 eq.) in dry THF (1.5 mL) in a 4 dram vial was added thionyl chloride (0.558 mmol, 1.43 eq.) and was stirred at reflux for 0.5 h. After cooling to about 35° C., a solution of the requisite aniline (0.390 mmol, 1 eq.) and triethylamine (1.560 mmol, 4 eq.) in dry THF (1 mL) was added drop wise. After stirring at room temperature for 2 hours the reaction mixture was quenched with 1N HCl and extracted with ethyl acetate (×3). The combined organic layer was dried over anhydrous Na$_2$SO$_4$, filtered, and evaporated to dryness. The resulting residue was purified according to the preparative RP-HPLC methods described herein.

General Procedure (Isoxazole Amide) 2:

To a solution of the appropriate aniline (0.049 mmol, 1 eq.) in DMF (0.1 M, 0.5 mL) was added PyBOP (0.097 mmol, 2 eq.), Hunig's base (0.107 mmol, 2.2 eq.), and the appropriate benzoic acid (0.049 mmol, 1 eq.). The reaction mixture was subjected to microwave radiation at 120° C. for 20 min, following which the resulting residue was purified according to the preparative RP HPLC methods described herein.

Synthesis of Intermediates

KSC-392-136

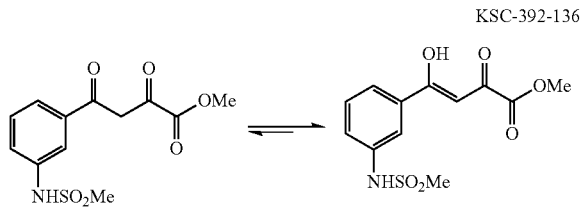

KSC-392-136

(Z)-Methyl 4-hydroxy-4-(3-(methylsulfonamido)phenyl)-2-oxobut-3-enoate (KSC-392-136): To a solution of N-(3-acetylphenyl)methanesulfonamide (0.5 g, 2.345 mmol, 1 eq.) in Et$_2$O (9.4 mL, 0.25M) was added sodium methoxide (1.126 ml, 4.92 mmol, 2.1 eq.), followed by dimethyl oxalate (0.277 g, 2.345 mmol, 1 eq.) and the mixture was stirred for 24 h at room temperature. Upon completion, the mixture was quenched with 1N HCl and extracted with EtOAc (×3). The combined organic layers were washed with brine, dried over anhydrous Na₂SO₄, and evaporated to dryness. The resulting residue was purified via MPLC (silica, 10-100% hexanes/EtOAc) to provide (Z)-methyl 4-hydroxy-4-(3-(methylsulfonamido)phenyl)-2-oxobut-3-enoate (0.844 g, 2.115 mmol, 90% yield) (KSC-392-136) as light yellow solid. ¹H NMR (500 MHz, DMSO-d₆) δ 10.10 (s, 1H), 7.92-7.79 (m, 2H), 7.61-7.41 (m, 2H), 7.06 (s, 1H), 3.87 (s, 3H), 3.05 (s, 3H); HRMS (ESI-TOF) m/z: [M−H]⁻ Calcd for Cl₂H₁₂NO₆S 298.0391; Found 298.0378.

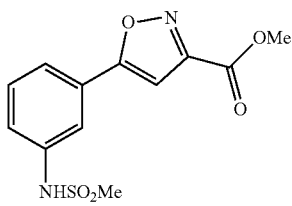

KSC-392-147

Methyl 5-(3-hydroxy-4-methoxyphenyl)isoxazole-3-carboxylate (KSC-392-147): To a stirred solution of (7)-methyl 4-hydroxy-4-(3-(methylsulfonamido)phenyl)-2-oxobut-3-enoate (0.400 g, 1.336 mmol) in MeOH (4.86 mL, 0.2 M) was added hydroxylamine hydrochloride (0.203 g, 2.91 mmol) at room temperature. The resulting mixture was then heated to reflux for 24 h. Upon completion, the reaction mixture was concentrated under reduced pressure. The crude residue was dissolved in EtOAc, washed with water, dried over anhydrous Na₂SO₄, and evaporated to dryness. The resulting residue was purified via MPLC (silica, 10-100% hexanes/EtOAc) to provide methyl 5-(3-(methylsulfonamido)phenyl)isoxazole-3-carboxylate (0.368 g, 1.242 mmol, 93% yield) (KSC-392-147) as off-white solid. ¹H NMR (400 MHz, Acetone-d₆) δ 7.91-7.85 (m, 1H), 7.71 (dt, J=7.6, 1.4 Hz, 1H), 7.55 (td, J=7.8, 0.6 Hz, 1H), 7.50 (ddd, J=8.1, 2.2, 1.3 Hz, 1H), 7.22 (s, 1H), 3.96 (s, 3H), 3.09 (s, 3H); ¹³C NMR (101 MHz, Acetone-d₆) δ 171.70, 160.73, 157.74, 140.33, 131.23, 128.46, 122.99, 122.45, 117.66, 101.41. HRMS (ESI-TOF) m/z: [M−H]⁻ Calcd for C₁₄H₁₀ClO₃ 261.0324; Found 261.0237.

5-(3-(Methylsulfonamido)phenyl)isoxazole-3-carboxylic acid (KSC-392-152): To methyl 5-(3-(methylsulfonamido)phenyl)isoxazole-3-carboxylate (0.360 g, 1.215 mmol) in a mixture of EtOH (7.23 ml):THF (3.62 ml) (2:1, 0.112M) was added 1 M NaOH (2.065 ml, 2.065 mmol) and heated to reflux for 4 h. Upon completion, the reaction mixture was concentrated and diluted with 1N HCl. The aqueous layer was extracted with EtOAc (×3). The combined organic layers were washed with brine, dried over anhydrous Na₂SO₄, and concentrated in vacuo to provide 5-(3-(methylsulfonamido)phenyl)isoxazole-3-carboxylic acid (0.332 g, 1.176 mmol, 97% yield) (KSC-392-152) as off-white solid. ¹H NMR (400 MHz, DMSO-d₆) δ 10.03 (s, 1H), 7.74-7.65 (m, 2H), 7.57-7.48 (m, 1H), 7.38 (s, 1H), 7.35 (ddd, J=8.1, 2.2, 1.0 Hz, 1H), 3.07 (s, 3H); HRMS (ESI-TOF) m/z: [M+H]⁺ Calcd for C₁₁H₁₁N₂O₅S 283.0383; Found 283.0374.

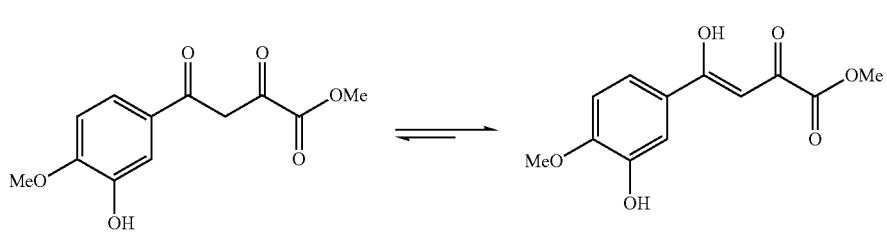

KSC-392-122

Methyl 4-(3-hydroxy-4-methoxyphenyl)-2,4-dioxobutanoate (KSC-392-122): To a solution of 1-(3-hydroxy-4-methoxyphenyl)ethanone (0.533 g, 1.901 mmol) in Et₂O (7.60 ml, 0.25M) was added sodium methoxide (0.652 ml, 2.85 mmol), followed by dimethyl oxalate (0.224 g, 1.901 mmol) and the mixture was stirred for 24 h at room temperature. Upon completion, the mixture was quenched with 1N HCl and extracted with EtOAc (×3). The combined organic layers were washed with brine, dried over anhydrous Na₂SO₄, and evaporated to dryness. The resulting residue was purified MPLC (silica, 10-100% hexanes/EtOAc) to provide 4-(3-hydroxy-4-methoxyphenyl)-2,4-dioxobutanoate (0.250 g, 0.991 mmol, 52.2% yield) (KSC-392-122) as yellow solid. ¹H NMR (400 MHz, Acetone-d₆) δ 7.68 (dd, J=8.5, 2.2 Hz, 1H), 7.55 (d, J=2.2 Hz, 1H), 7.13 (d, J=8.5 Hz, 1H), 7.06 (s, 1H), 3.97 (s, 3H), 3.89 (s, 3H); HRMS (ESI-TOF) m/z: [M+Na]⁺ Calcd for Cl₂H₁₂NaO₆ 275.0526; Found 275.0543.

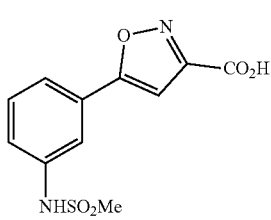

KSC-392-152

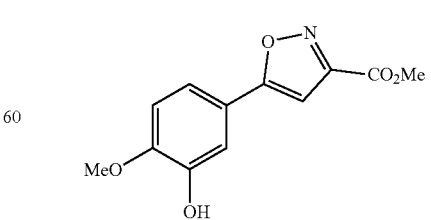

KSC-392-089

Methyl 5-(3-hydroxy-4-methoxyphenyl)isoxazole-3-carboxylate (KSC-392-089): To a stirred solution of (Z)-methyl 4-hydroxy-4-(3-hydroxy-4-methoxyphenyl)-2-oxobut-3-enoate (0.245 g, 0.971 mmol) in MeOH (4.86 ml, 0.2 M) was added hydroxylamine hydrochloride (0.203 g, 2.91 mmol) at room temperature. The resulting mixture was then heated to reflux for 24 h. Upon completion, the reaction mixture was concentrated under reduced pressure. The crude residue was dissolved in EtOAc, washed with water, dried over anhydrous $Na_2SO_4$, and evaporated to dryness. The resulting residue was purified via MPLC (silica, 10-100% hexanes/EtOAc) to provide methyl 5-(3-hydroxy-4-methoxyphenyl)isoxazole-3-carboxylate (0.222 g, 0.891 mmol, 92% yield) (KSC-392-089) as off-white solid. $^1$H NMR (400 MHz, DMSO-$d_6$) δ 9.47 (s, 1H), 7.41 (dd, J=8.4, 2.2 Hz, 1H), 7.33 (d, J=2.1 Hz, 1H), 7.29 (s, 1H), 7.09 (d, J=8.5 Hz, 1H), 3.93 (s, 3H), 3.86 (s, 3H); $^{13}$C NMR (101 MHz, DMSO) δ 171.35, 159.91, 156.47, 150.09, 146.92, 118.77, 117.83, 112.48, 112.44, 99.09, 55.68, 52.71; HRMS (ESI-TOF) m/z: [M+H]$^+$ Calcd for $C_{12}H_{12}NO_5$ 250.0710; Found 250.0707.

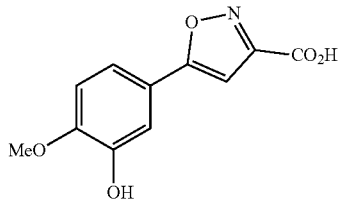

KSC-392-095

5-(3-Hydroxy-4-methoxyphenyl)isoxazole-3-carboxylic acid (KSC-392-095): To methyl 5-(3-hydroxy-4-methoxyphenyl)isoxazole-3-carboxylate (0.223 g, 0.895 mmol) in a mixture of EtOH (5.3 mL): THF (2.7 mL) (2:1, 0.112M) was added 1 M NaOH (1.5 ml, 1.521 mmol) and heated to reflux for 4 h. Upon completion, the reaction mixture was concentrated and diluted with 1N HCl. The aqueous layer was extracted with EtOAc (×3). The combined organic layers were washed with brine, dried over anhydrous $Na_2SO_4$, and concentrated in vacuo to provide 5-(3-hydroxy-4-methoxyphenyl)isoxazole-3-carboxylic acid (0.208 g, 0.884 mmol, 99% yield) as off-white solid. $^1$H NMR (400 MHz, Acetone-$d_6$) δ 7.42 (dd, J=8.3, 2.2 Hz, 1H), 7.39 (d, J=2.1 Hz, 1H), 7.11 (d, J=8.4 Hz, 1H), 7.05 (s, 1H), 3.92 (s, 3H); $^{13}$C NMR (101 MHz, Acetone) δ 172.53, 161.24, 158.15, 150.73, 147.99, 120.76, 118.90, 113.28, 112.77, 99.84, 56.39; HRMS (ESI-TOF) m/z: [M+H]$^+$ Calcd for $C_{11}H_{10}NO_5$ 236.0553; Found 236.0545.

0.25M) was added sodium methoxide (0.267 ml, 1.168 mmol), followed by dimethyl oxalate (0.092 g, 0.779 mmol) and the mixture was stirred for 24 h at room temperature. Upon completion, the mixture was quenched with 1N HCl and extracted with EtOAc (×3). The combined organic layers were washed with brine, dried over anhydrous $Na_2SO_4$, and evaporated to dryness. The resulting residue was purified MPLC (silica, 10-100% hexanes/EtOAc) to provide methyl 4-(4-fluoro-3-hydroxyphenyl)-2,4-dioxobutanoate (0.133 g, 0.554 mmol, 71% yield) (KSC-392-097) as light yellow liquid which solidified on cooling. $^1$H NMR (400 MHz, Acetone-$d_6$) δ 7.72 (dd, J=8.5, 2.3 Hz, 1H), 7.66 (ddd, J=8.6, 4.4, 2.3 Hz, 1H), 7.31 (dd, J=10.7, 8.5 Hz, 1H), 7.08 (s, 1H), 3.90 (s, 3H); HRMS (ESI-TOF) m/z: [M+H]$^+$ Calcd for $C_{14}H_{10}ClO_3$ 261.0324; Found 261.0348.

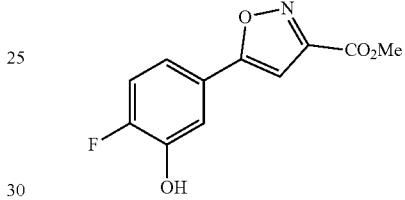

KSC-392-083

Methyl 5-(4-fluoro-3-hydroxyphenyl)isoxazole-3-carboxylate (KSC-392-083): To a stirred solution of (Z)-methyl 4-(4-fluoro-3-hydroxyphenyl)-4-hydroxy-2-oxobut-3-enoate (0.198 g, 0.824 mmol, 1 eq.) in MeOH (4 mL, 0.2 M) was added hydroxylamine hydrochloride (0.172 g, 2.473 mmol) at room temperature. The resulting mixture was then heated to reflux for 24 h. Upon completion, the reaction mixture was concentrated under reduced pressure. The crude residue was dissolved in EtOAc, washed with water, dried over anhydrous $Na_2SO_4$, and evaporated to dryness. The resulting residue was purified via MPLC (silica, 10-100% hexanes/EtOAc) to provide methyl methyl 5-(4-fluoro-3-hydroxyphenyl)isoxazole-3-carboxylate (0.080 g, 0.337 mmol, 41% yield) (KSC-392-083) as off-white solid. $^1$H NMR (400 MHz, DMSO-$d_6$) δ 10.39 (d, J=0.9 Hz, 1H), 7.49

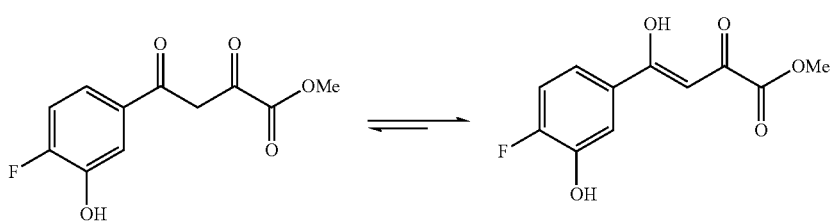

KSC-392-097

Methyl 4-(4-fluoro-3-hydroxyphenyl)-2,4-dioxobutanoate (KSC-392-097): To a solution of 1-(4-fluoro-3-hydroxyphenyl)ethanone (0.120 g, 0.779 mmol) in $Et_2O$ (3 ml, (dd, J=8.3, 2.2 Hz, 1H), 7.47-7.38 (m, 2H), 7.34 (dd, J=11.0, 8.5 Hz, 1H), 3.92 (s, 3H); HRMS (ESI-TOF) m/z: [M+H]$^+$ Calcd for $C_{11}H_9FNO_4$ 238.0510; Found 238.0501.

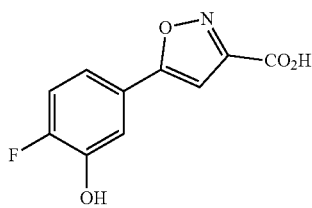

KSC-392-088

5-(4-Fluoro-3-hydroxyphenyl)isoxazole-3-carboxylic acid (KSC-392-088): To methyl 5-(4-fluoro-3-hydroxyphenyl)isoxazole-3-carboxylate (0.08 g, 0.337 mmol) in a mixture of EtOH (2 mL): THF (1 mL) (2:1, 0.112M) was added 1 M NaOH (0.573 ml, 0.573 mmol) and heated to reflux for 4 h. Upon completion, the reaction mixture was concentrated and diluted with 1N HCl. The aqueous layer was extracted with EtOAc (×3). The combined organic layers were washed with brine, dried over anhydrous $Na_2SO_4$, and concentrated in vacuo to provide 5-(4-fluoro-3-hydroxyphenyl)isoxazole-3-carboxylic acid (0.070 g, 0.314 mmol, 93% yield) as off-white solid. $^1$H NMR (400 MHz, DMSO-$d_6$) δ 10.38 (bs, 1H), 7.47 (dd, J=8.3, 2.1 Hz, 1H), 7.42-7.38 (m, 1H), 7.35-7.31 (m, 1H), 7.30 (s, 1H); $^{13}$C NMR (101 MHz, DMSO-$d_6$) δ 170.09, 160.75, 157.75, 152.53 (d, J=246.5 Hz), 145.58 (d, J=12.9 Hz), 123.01, 117.69 (d, J=7.2 Hz), 117.18 (d, J=19.3 Hz), 114.95 (d, J=3.7 Hz), 100.54; HRMS (ESI-TOF) m/z: [M+H]$^+$ Calcd for $C_{10}H_7FNO_4$ 224.0354; Found 224.0342.

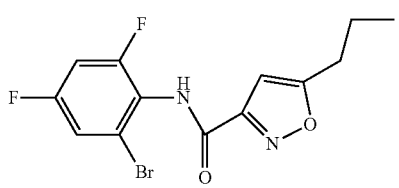

KSC-338-013

N-(2-Bromo-4,6-difluorophenyl)-5-propylisoxazole-3-carboxamide (KSC-338-013): $^1$H NMR (400 MHz, DMSO-$d_6$) δ 10.53 (s, 1H), 7.67-7.59 (m, 1H), 7.56-7.45 (m, 1H), 6.70 (s, 1H), 2.83 (t, J=7.4 Hz, 2H), 1.70 (h, J=7.4 Hz, 2H), 0.95 (t, J=7.4 Hz, 3H); HRMS (ESI-TOF) m/z: [M+H]$^+$ Calcd for $C_{13}H_{12}BrF_2N_2O_2$ 345.0045; Found 345.0045.

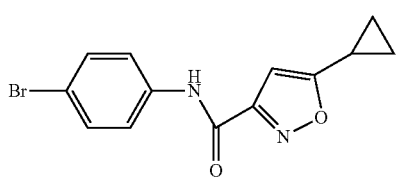

KSC-338-014

N-(4-Bromophenyl)-5-cyclopropylisoxazole-3-carboxamide (KSC-338-014): $^1$H NMR (400 MHz, DMSO-$d_6$) δ 10.72 (s, 1H), 7.80-7.65 (m, 2H), 7.58-7.43 (m, 2H), 6.59 (s, 1H), 2.29-2.15 (m, 1H), 1.17-1.06 (m, 2H), 1.01-0.85 (m, 2H); HRMS (ESI-TOF) m/z: [M+H]$^+$ Calcd for $C_{13}H_{12}BrN_2O_2$ 307.0077; Found 307.0077.

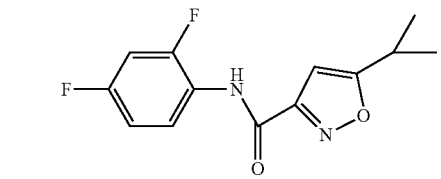

KSC-338-015

N-(2,4-Difluorophenyl)-5-isopropylisoxazole-3-carboxamide (KSC-338-015): $^1$H NMR (400 MHz, DMSO-$d_6$) δ 10.45 (s, 1H), 7.61-7.49 (m, 1H), 7.41-7.29 (m, 1H), 7.18-7.08 (m, 1H), 6.67 (d, J=0.9 Hz, 1H), 3.24-3.11 (m, 1H), 1.29 (d, J=6.9 Hz, 6H); HRMS (ESI-TOF) m/z: [M+H]$^+$ Calcd for $C_{13}H_{13}F_2N_2O_2$ 267.0940; Found 267.0945.

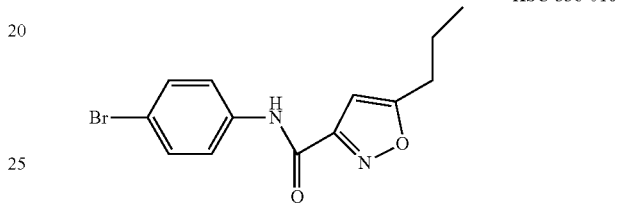

KSC-338-016

N-(4-Bromophenyl)-5-propylisoxazole-3-carboxamide (KSC-338-016): $^1$H NMR (400 MHz, DMSO-$d_6$) δ 10.75 (s, 1H), 7.76-7.65 (m, 2H), 7.59-7.49 (m, 2H), 6.67 (s, 1H), 2.80 (t, J=7.4 Hz, 2H), 1.68 (h, J=7.4 Hz, 2H), 0.92 (t, J=7.3 Hz, 3H); HRMS (ESI-TOF) m/z: [M+H]$^+$ Calcd for $C_{13}H_{14}BrN_2O_2$ 309.0233; Found 309.0234.

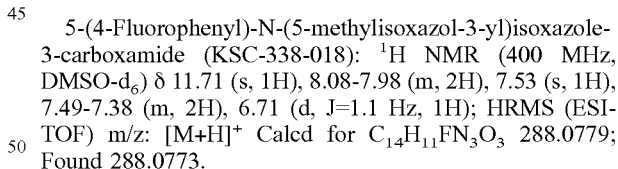

KSC-338-018

5-(4-Fluorophenyl)-N-(5-methylisoxazol-3-yl)isoxazole-3-carboxamide (KSC-338-018): $^1$H NMR (400 MHz, DMSO-$d_6$) δ 11.71 (s, 1H), 8.08-7.98 (m, 2H), 7.53 (s, 1H), 7.49-7.38 (m, 2H), 6.71 (d, J=1.1 Hz, 1H); HRMS (ESI-TOF) m/z: [M+H]$^+$ Calcd for $C_{14}H_{11}FN_3O_3$ 288.0779; Found 288.0773.

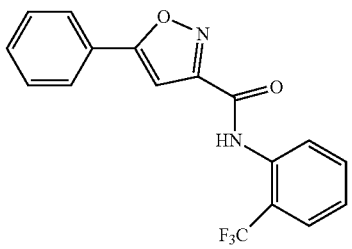

KSC-338-020

5-Phenyl-N-(2-(trifluoromethyl)phenyl)isoxazole-3-carboxamide (KSC-338-020): $^1$H NMR (400 MHz, DMSO-$d_6$) δ 10.50 (s, 1H), 8.02-7.91 (m, 2H), 7.86-7.72 (m, 2H), 7.67-7.60 (m, 1H), 7.63-7.53 (m, 4H), 7.50 (s, 1H); HRMS (ESI-TOF) m/z: [M+H]+ Calcd for $C_{17}H_{12}F_3N_2O_2$ 333.0845; Found 333.0831.

KSC-338-021

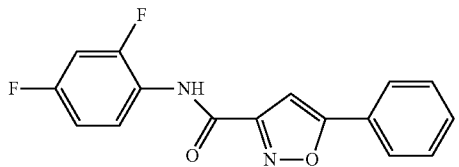

N-(2,4-Difluorophenyl)-5-phenylisoxazole-3-carboxamide (KSC-338-021): $^1$H NMR (400 MHz, DMSO-d$_6$) δ 10.57 (s, 1H), 8.02-7.87 (m, 2H), 7.67-7.53 (m, 4H), 7.51 (s, 1H), 7.40 (ddd, J=10.6, 9.1, 2.9 Hz, 1H), 7.20-7.10 (m, 2H); HRMS (ESI-TOF) m/z: [M+NH$_4$]+ Calcd for $C_{16}H_{14}F_2N_3O_2$ 318.1049; Found 318.1059.

KSC-338-023

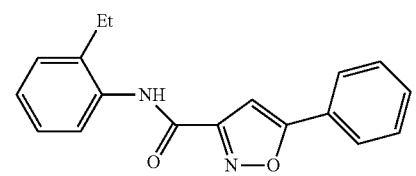

5-Chloro-N-ethyl-2-methoxy-N-phenylbenzamide (KSC-338-010): $^1$H NMR (400 MHz, DMSO-d$_6$) δ 10.28 (s, 1H), 8.02-7.90 (m, 2H), 7.63-7.52 (m, 3H), 7.48 (s, 1H), 7.40-7.28 (m, 2H), 7.30-7.22 (m, 2H), 2.64 (q, J=7.6 Hz, 2H), 1.15 (t, J=7.5 Hz, 3H); HRMS (ESI-TOF) m/z: [M+H]+ Calcd for $C_{18}H_{17}N_2O_2$ 293.1285; Found 293.1283.

KSC-338-024

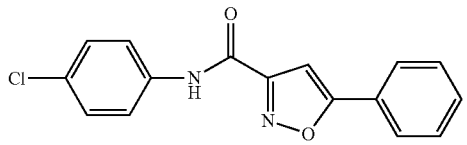

N-(4-Chlorophenyl)-5-phenylisoxazole-3-carboxamide (KSC-338-024): $^1$H NMR (400 MHz, DMSO-d$_6$) δ 10.92 (s, 1H), 8.01-7.93 (m, 2H), 7.89-7.81 (m, 2H), 7.62-7.53 (m, 3H), 7.50 (s, 1H), 7.49-7.40 (m, 2H); HRMS (ESI-TOF) m/z: [M+H]+ Calcd for $C_{16}H_{12}ClN_2O_2$ 299.0582; Found 299.0572.

KSC-338-074

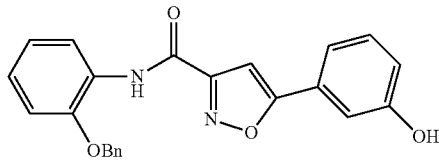

N-(2-(Benzyloxy)phenyl)-5-(3-hydroxyphenyl)isoxazole-3-carboxamide (KSC-338-074):
This compound was prepared following the General Procedure (isoxazole amide) 2 using 5-(3-hydroxyphenyl) isoxazole-3-carboxylic acid (10 mg, 0.049 mmol) and 2-(benzyloxy)aniline (10 mg, 0.049 mmol). Yield: 5 mg (25%); 100% purity. $^1$H NMR (400 MHz, DMSO-d$_6$) δ 9.90 (s, 1H), 9.64 (s, 1H), 8.06-7.98 (m, 2H), 7.55-7.48 (m, 2H), 7.47-7.28 (m, 7H), 7.23-7.14 (m, 2H), 7.05-6.99 (m, 2H), 6.95 (ddd, J=7.7, 2.4, 1.4 Hz, 1H), 5.25 (s, 2H); HRMS (ESI-TOF) m/z: [M+H]+ Calcd for $C_{23}H_{19}N_2O_4$ 387.1339; Found 387.1343.

KSC-338-075

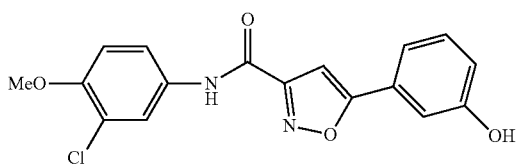

N-(3-Chloro-4-methoxyphenyl)-5-(3-hydroxyphenyl) isoxazole-3-carboxamide (KSC-338-075): This compound was prepared following the General Procedure (isoxazole amide) 2 using 5-(3-hydroxyphenyl)isoxazole-3-carboxylic acid (10 mg, 0.049 mmol) and 3-chloro-4-methoxyaniline (8 mg, 0.049 mmol). Yield: 3 mg (16%); 100% purity. $^1$H NMR (400 MHz, DMSO-d$_6$) δ 10.78 (s, 1H), 9.90 (s, 1H), 7.94 (d, J=2.5 Hz, 1H), 7.72 (dd, J=9.0, 2.6 Hz, 1H), 7.43-7.32 (m, 3H), 7.34-7.27 (m, 1H), 7.18 (d, J=9.1 Hz, 1H), 6.95 (ddd, J=7.2, 2.5, 1.8 Hz, 1H), 3.85 (s, 3H); HRMS (ESI-TOF) m/z: [M+H]+ Calcd for $C_{17}H_{14}ClN_2O_4$ 345.0637; Found 345.0649.

KSC-338-094

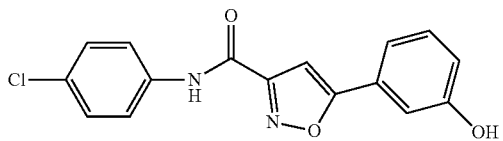

N-(4-Chlorophenyl)-5-(3-hydroxyphenyl)isoxazole-3-carboxamide (KSC-338-094): This compound was prepared following the General Procedure (isoxazole amide) 2 using 5-(3-hydroxyphenyl)isoxazole-3-carboxylic acid (20 mg, 0.097 mmol) and 4-chloroaniline (12 mg, 0.097 mmol). Yield: 9 mg (28%); 100% purity. NMR (400 MHz, DMSO-d$_6$) δ 10.90 (s, 1H), 9.94 (s, 1H), 7.88-7.79 (m, 2H), 7.48-7.40 (m, 2H), 7.43-7.32 (m, 3H), 7.33-7.27 (m, 1H), 6.98-6.91 (m, 1H); HRMS (ESI-TOF) m/z: [M–H]– Calcd for $C_{16}H_{10}ClN_2O_3$ 313.0385; Found 313.0393.

KSC-338-095

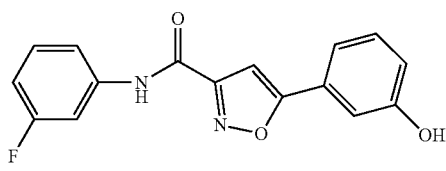

N-(3-Fluorophenyl)-5-(3-hydroxyphenyl)isoxazole-3-carboxamide (KSC-338-095): This compound was prepared following the General Procedure (isoxazole amide) 2 using 5-(3-hydroxyphenyl)isoxazole-3-carboxylic acid (20 mg, 0.097 mmol) and 3-fluoroaniline (11 mg, 0.097 mmol).

Yield: 7 mg (23%); 100% purity. NMR (400 MHz, DMSO-$d_6$) δ 10.94 (s, 1H), 7.69 (dt, J=11.5, 2.3 Hz, 1H), 7.57 (ddd, J=8.2, 2.0, 0.9 Hz, 1H), 7.46-7.31 (m, 4H), 7.31-7.23 (m, 1H), 7.04-6.88 (m, 2H); HRMS (ESI-TOF) m/z: [M−H]⁻ Calcd for $C_{16}H_{10}FN_2O_3$ 297.0681; Found 297.0663.

2H), 7.94 (d, J=2.5 Hz, 1H), 7.72 (dd, J=9.0, 2.6 Hz, 1H), 7.68-7.62 (m, 2H), 7.54 (s, 1H), 7.18 (d, J=9.0 Hz, 1H), 3.85 (s, 3H); HRMS (ESI-TOF) m/z: [M+H]⁺ Calcd for $C_{17}H_{13}Cl_2N_2O_3$ 363.0298; Found 363.0277.

KSC-338-100

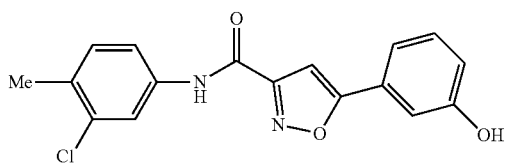

N-(3-Chloro-4-methylphenyl)-5-(3-hydroxyphenyl)isoxazole-3-carboxamide (KSC-338-100): This compound was prepared following the General Procedure (isoxazole amide) 2 using 5-(3-hydroxyphenyl)isoxazole-3-carboxylic acid (20 mg, 0.097 mmol) and 3-chloro-4-methylaniline (14 mg, 0.097 mmol). Yield: 14 mg (45%); 100% purity. ¹H NMR (400 MHz, DMSO-$d_6$) δ 10.85 (s, 1H), 9.94 (s, 1H), 7.95 (d, J=2.2 Hz, 1H), 7.64 (dd, J=8.3, 2.2 Hz, 1H), 7.43-7.31 (m, 4H), 7.33-7.27 (m, 2H), 6.98-6.90 (m, 1H), 2.30 (s, 3H); HRMS (ESI-TOF) m/z: [M+H]⁺ Calcd for $C_{17}H_{14}ClN_2O_3$ 329.0687; Found 329.0679.

KSC-392-010

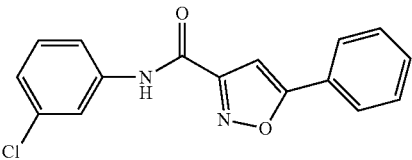

N-(3-Chlorophenyl)-5-phenylisoxazole-3-carboxamide (KSC-392-010): This compound was prepared following the General Procedure (isoxazole amide) 2 using 55-phenylisoxazole-3-carboxylic acid (30 mg, 0.159 mmol) and 3-chloroaniline (20 mg, 0.159 mmol). Yield: 30 mg (63%); 100% purity. ¹H NMR (400 MHz, DMSO-$d_6$) δ 10.95 (s, 1H), 8.00-7.88 (m, 3H), 7.73 (ddd, J=8.3, 2.1, 1.0 Hz, 1H), 7.62-7.53 (m, 3H), 7.48 (s, 1H), 7.41 (t, J=8.1 Hz, 1H), 7.22 (ddd, J=8.0, 2.1, 0.9 Hz, 1H); HRMS (ESI-TOF) m/z: [M+H]⁺ Calcd for $C_{16}H_{12}ClN_2O_2$ 299.0582; Found 299.0559.

KSC-392-008

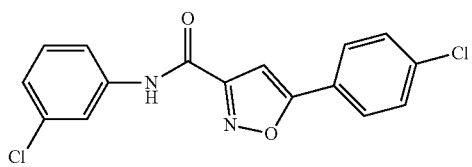

N-(3-Chlorophenyl)-5-(4-chlorophenyl)isoxazole-3-carboxamide (KSC-392-008): This compound was prepared following the General Procedure (isoxazole amide) 2 using 5-(4-chlorophenyl)isoxazole-3-carboxylic acid (30 mg, 0.134 mmol) and 3-chloroaniline (17 mg, 0.134 mmol). Yield: 28 mg (62%); 100% purity. ¹H NMR (400 MHz, DMSO-$d_6$) δ 10.97 (s, 1H), 8.03-7.95 (m, 2H), 7.95 (t, J=2.0 Hz, 1H), 7.73 (ddd, J=8.2, 2.0, 1.0 Hz, 1H), 7.69-7.60 (m, 2H), 7.52 (s, 1H), 7.41 (t, J=8.1 Hz, 1H), 7.22 (ddd, J=8.1, 2.1, 0.9 Hz, 1H); HRMS (ESI-TOF) m/z: [M−H]⁻ Calcd for $C_{16}H_9Cl_2N_2O_2$ 331.0046; Found 331.0027.

KSC-392-011

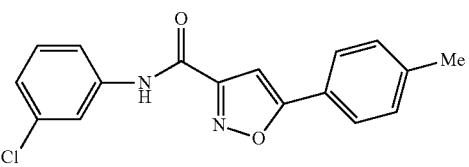

N-(3-Chlorophenyl)-5-(p-tolyl)isoxazole-3-carboxamide (KSC-392-011): This compound was prepared following the General Procedure (isoxazole amide) 2 using 5-(p-tolyl)isoxazole-3-carboxylic acid (30 mg, 0.148 mmol) and 3-chloroaniline (19 mg, 0.148 mmol). Yield: 15 mg (35%); 100% purity. ¹H NMR (400 MHz, DMSO-$d_6$) δ 10.93 (s, 1H), 7.95 (t, J=2.0 Hz, 1H), 7.88-7.79 (m, 2H), 7.73 (ddd, J=8.3, 2.0, 0.9 Hz, 1H), 7.45-7.34 (m, 4H), 7.22 (ddd, J=8.0, 2.1, 0.9 Hz, 1H), 2.38 (s, 3H); HRMS (ESI-TOF) m/z: [M+H]⁺ Calcd for $C_{17}H_{14}ClN_2O_2$ 313.0738; Found 313.0726.

KSC-392-009

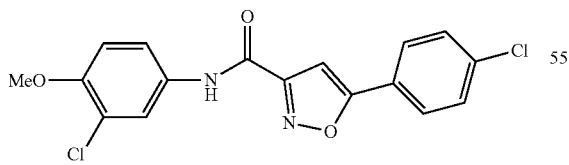

N-(3-Chloro-4-methoxyphenyl)-5-(4-chlorophenyl)isoxazole-3-carboxamide (KSC-392-009): This compound was prepared following the General Procedure (isoxazole amide) 2 using 5-(4-chlorophenyl)isoxazole-3-carboxylic acid (30 mg, 0.134 mmol) and 3-chloro-4-methoxyaniline (21 mg, 0.134 mmol). Yield: 8 mg (15%); 98.9% purity. ¹H NMR (400 MHz, DMSO-$d_6$) δ 10.81 (s, 1H), 8.04-7.97 (m,

KSC-392-012

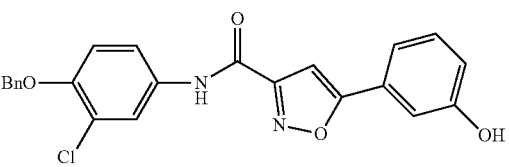

N-(4-(Benzyloxy)-3-chlorophenyl)-5-(3-hydroxyphenyl)isoxazole-3-carboxamide (KSC-392-012): This compound was prepared following the General Procedure (isoxazole amide) 2 using 5-(3-hydroxyphenyl)isoxazole-3-carboxylic acid (30 mg, 0.146 mmol) and 4-(benzyloxy)-3-chloroaniline (34 mg, 0.146 mmol). Yield: 16 mg (25%); 97.9% purity. ¹H NMR (400 MHz, DMSO-$d_6$) δ 10.78 (s, 1H), 10.00 (s, 1H), 7.93 (d, J=2.6 Hz, 1H), 7.66 (dd, J=9.0, 2.6

Hz, 1H), 7.51-7.43 (m, 2H), 7.45-7.31 (m, 6H), 7.32-7.26 (m, 1H), 7.26 (d, J=9.1 Hz, 1H), 6.98-6.90 (m, 1H), 5.20 (s, 2H); HRMS (ESI-TOF) m/z: [M+H]+ Calcd for C23H18ClN2O4 421.0950; Found 421.0935.

KSC-392-032

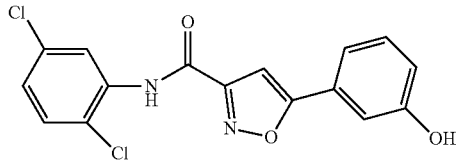

N-(2,5-Dichlorophenyl)-5-(3-hydroxyphenyl)isoxazole-3-carboxamide (KSC-392-032): This compound was prepared following the General Procedure (isoxazole amide) 2 using 5-(3-hydroxyphenyl)isoxazole-3-carboxylic acid (20 mg, 0.097 mmol) and 2,5-dichloroaniline (16 mg, 0.097 mmol). Yield: 2 mg (6%); 100% purity; HRMS (ESI-TOF) m/z: [M–H]− Calcd for C16H9Cl2N2O3 346.9995; Found 347.0006.

KSC-392-033

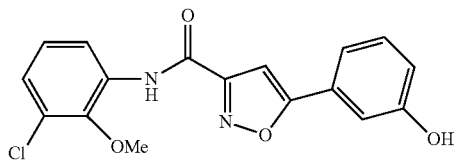

N-(3-Chloro-2-methoxyphenyl)-5-(3-hydroxyphenyl)isoxazole-3-carboxamide (KSC-392-033): This compound was prepared following the General Procedure (isoxazole amide) 2 using 5-(3-hydroxyphenyl)isoxazole-3-carboxylic acid (20 mg, 0.097 mmol) and 3-chloro-2-methoxyaniline (15 mg, 0.097 mmol). Yield: 4 mg (13%); 100% purity. NMR (400 MHz, DMSO-d6) δ 9.94 (s, 1H), 9.91 (s, 1H), 7.92-7.84 (m, 1H), 7.46 (s, 1H), 7.44-7.33 (m, 3H), 7.32 (t, J=2.0 Hz, 1H), 7.22 (t, J=8.1 Hz, 1H), 6.95 (ddd, J=7.7, 2.4, 1.6 Hz, 1H), 3.85 (s, 3H); HRMS (ESI-TOF) m/z: [M+H]+ Calcd for C17H14ClN2O4 345.0637; Found 345.0616.

KSC-392-038

N-(5-Chloro-2-methylphenyl)-5-(3-methoxyphenyl)isoxazole-3-carboxamide (KSC-392-038): This compound was prepared following the General Procedure (isoxazole amide) 2 using 5-(3-methoxyphenyl)isoxazole-3-carboxylic acid (20 mg, 0.091 mmol) and 5-chloro-2-methylaniline (13 mg, 0.091 mmol). Yield: 15 mg (47%); 100% purity. NMR (400 MHz, DMSO-d6) δ 10.36 (s, 1H), 7.59-7.44 (m, 5H), 7.33 (d, J=8.3 Hz, 1H), 7.27 (dd, J=8.2, 2.2 Hz, 1H), 7.13 (ddd, J=8.2, 2.6, 1.1 Hz, 1H), 3.86 (s, 3H), 2.24 (s, 3H); HRMS (ESI-TOF) m/z: [M+H]+ Calcd for C18H16ClN2O3 343.0844; Found 343.0828.

KSC-392-041

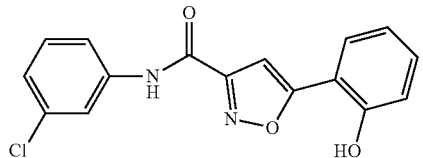

N-(3-Chlorophenyl)-5-(2-hydroxyphenyl)isoxazole-3-carboxamide (KSC-392-041): This compound was prepared following the General Procedure (isoxazole amide) 2 using 5-(2-hydroxyphenyl)isoxazole-3-carboxylic acid (30 mg, 0.146 mmol) and 3-chloroaniline (19 mg, 0.146 mmol). Yield: 7 mg (16%); 99.6% purity. 1H NMR (400 MHz, DMSO-d6) 10.92 (s, 1H), 10.80 (s, 1H), 7.98 (t, J=2.0 Hz, 1H), 7.85 (dd, J=7.9, 1.6 Hz, 1H), 7.77 (ddd, J=8.2, 1.8, 0.7 Hz, 1H), 7.44-7.33 (m, 2H), 7.26 (s, 1H), 7.21 (ddd, J=8.0, 2.1, 0.9 Hz, 1H), 7.10-7.06 (m, 1H), 7.02-6.96 (m, 1H); 13C NMR (101 MHz, DMSO-d6) δ 167.60, 159.36, 157.65, 154.95, 139.52, 132.97, 132.02, 130.39, 126.75, 124.07, 120.02, 119.52, 118.96, 116.58, 113.14, 102.21; HRMS (ESI-TOF) m/z: [M+]+ Calcd for C16H12ClN2O3 315.0531; Found 315.0483.

KSC-392-042

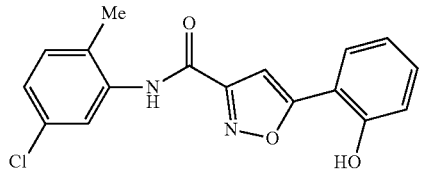

N-(5-Chloro-2-methylphenyl)-5-(2-hydroxyphenyl)isoxazole-3-carboxamide (KSC-392-042): This compound was prepared following the General Procedure (isoxazole amide) 2 using 5-(2-hydroxyphenyl)isoxazole-3-carboxylic acid (30 mg, 0.146 mmol) and 5-chloro-2-methylaniline (21 mg, 0.146 mmol). Yield: 7 mg (15%); 99% purity. 1H NMR (400 MHz, DMSO-d6) δ 10.80 (s, 1H), 10.35 (s, 1H), 7.86 (dd, J=7.9, 1.7 Hz, 1H), 7.53 (d, J=2.2 Hz, 1H), 7.39 (ddd, J=8.3, 7.3, 1.7 Hz, 1H), 7.38-7.30 (m, 1H), 7.28 (dd, J=8.2, 2.3 Hz, 1H), 7.25 (s, 1H), 7.09 (dd, J=8.4, 1.1 Hz, 1H), 7.06-6.93 (m, 1H), 2.26 (s, 3H); 13C NMR (101 MHz, DMSO-d6) δ 167.58, 159.12, 157.54, 154.93, 136.53, 132.26, 131.98, 131.86, 129.85, 126.75, 126.06, 125.67, 119.52, 116.56, 113.18, 102.20, 17.21; HRMS (ESI-TOF) m/z: [M+H]+ Calcd for C17H14ClN2O3 329.0687; Found 329.0656.

KSC-392-048

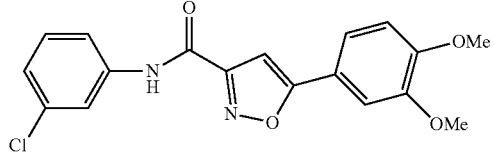

N-(5-Chloro-2-methylphenyl)-5-(2-hydroxyphenyl)isoxazole-3-carboxamide (KSC-392-048): This compound was prepared following the General Procedure (isoxazole amide) 2 using 5-(2-hydroxyphenyl)isoxazole-3-carboxylic acid (30 mg, 0.146 mmol) and 5-chloro-2-methylaniline (21 mg, 0.146 mmol). Yield: 7 mg (15%); 100% purity. $^1$H NMR (400 MHz, DMSO-$d_6$) δ 10.80 (s, 1H), 10.35 (s, 1H), 7.86 (dd, J=7.9, 1.7 Hz, 1H), 7.53 (d, J=2.2 Hz, 1H), 7.39 (ddd, J=8.3, 7.3, 1.7 Hz, 1H), 7.38-7.30 (m, 1H), 7.28 (dd, J=8.2, 2.3 Hz, 1H), 7.25 (s, 1H), 7.09 (dd, J=8.4, 1.1 Hz, 1H), 7.06-6.93 (m, 1H), 2.26 (s, 3H); $^{13}$C NMR (101 MHz, DMSO-$d_6$) δ 167.58, 159.12, 157.54, 154.93, 136.53, 132.26, 131.98, 131.86, 129.85, 126.75, 126.06, 125.67, 119.52, 116.56, 113.18, 102.20, 17.21; HRMS (ESI-TOF) m/z: [M+H]$^+$ Calcd for $C_{18}H_{16}ClN_2O_4$ 359.0793; Found 359.0774.

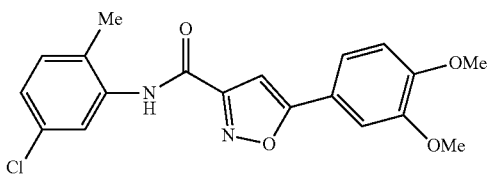

KSC-392-049

N-(5-Chloro-2-methylphenyl)-5-(3,4-dimethoxyphenyl)isoxazole-3-carboxamide (KSC-392-049): This compound was prepared following the General Procedure (isoxazole amide) 2 using 5-(3,4-dimethoxyphenyl)isoxazole-3-carboxylic acid (30 mg, 0.120 mmol) and 5-chloro-2-methylaniline (17 mg, 0.120 mmol). Yield: 9 mg (20%); 100% purity. $^1$H NMR (400 MHz, DMSO-$d_6$) δ 10.31 (s, 1H), 7.58-7.47 (m, 3H), 7.43 (s, 1H), 7.36-7.29 (m, 1H), 7.27 (dd, J=8.2, 2.2 Hz, 1H), 7.13 (d, J=8.4 Hz, 1H), 3.87 (s, 3H), 3.84 (s, 3H), 2.24 (s, 3H); $^{13}$C NMR (101 MHz, DMSO-$d_6$) δ 170.89, 159.31, 157.49, 150.99, 149.16, 136.52, 132.21, 131.88, 129.87, 126.06, 125.58, 118.89, 112.04, 109.24, 98.92, 55.79, 55.65, 17.20; HRMS (ESI-TOF) m/z: [M+H]$^+$ Calcd for $C_{19}H_{18}ClN_2O_4$ 373.0950; Found 373.0912.

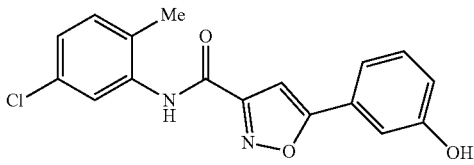

KSC-392-065

N-(5-chloro-2-methylphenyl)-5-(3-hydroxyphenyl)isoxazole-3-carboxamide (KSC-392-065): This compound was prepared following the General Procedure (isoxazole amide) 1 using 5-(3-hydroxyphenyl)isoxazole-3-carboxylic acid (80 mg, 0.390 mmol) and 5-chloro-2-methylaniline (55 mg, 0.390 mmol). Yield: 55 mg (43%); 99% purity. $^1$H NMR (400 MHz, Acetone-$d_6$) δ 9.19 (s, 1H), 7.95 (d, J=2.3 Hz, 1H), 7.50-7.37 (m, 3H), 7.32 (d, J=8.2 Hz, 1H), 7.23 (s, 1H), 7.19 (dd, J=8.2, 2.3 Hz, 1H), 7.03 (ddd, J=7.9, 2.4, 1.2 Hz, 1H), 2.38 (s, 3H); $^{13}$C NMR (101 MHz, Acetone-$d_6$) δ 172.82, 160.59, 159.11, 158.03, 137.76, 132.82, 132.07, 131.58, 130.67, 128.96, 126.42, 124.48, 119.08, 118.30, 113.52, 100.39, 17.49; HRMS (ESI-TOF) m/z: [M–H]$^-$ Calcd for $C_{17}H_{12}ClN_2O_3$ 327.0542, found: 327.0538.

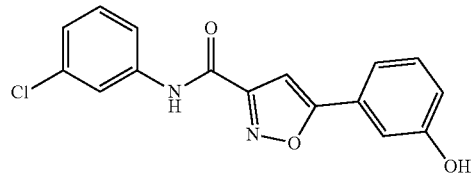

KSC-392-066

N-(3-Chlorophenyl)-5-(3-hydroxyphenyl)isoxazole-3-carboxamide (KSC-392-066): This compound was prepared following the General Procedure (isoxazole amide) 1 using 5-(3-hydroxyphenyl)isoxazole-3-carboxylic acid (80 mg, 0.390 mmol) and 3-chloroaniline (50 mg, 0.390 mmol). Yield: 26 mg (21%); 95% purity. $^1$H NMR (400 MHz, Acetone-$d_6$) δ 9.81 (s, 1H), 8.10 (t, J=1.9 Hz, 1H), 7.85-7.78 (m, 1H), 7.47-7.33 (m, 4H), 7.24-7.17 (m, 1H), 7.03 (ddd, J=7.8, 2.3, 1.2 Hz, 1H). $^{13}$C NMR (101 MHz, Acetone-$d_6$) δ 172.64, 160.67, 159.07, 158.30, 140.63, 134.92, 131.54, 131.30, 128.93, 125.30, 121.13, 119.66, 119.02, 118.26, 113.50, 100.43; HRMS (ESI-TOF) m/z: [M–H]$^-$ Calcd for $C_{16}H_{10}ClN_2O_3$ 313.0385, found: 313.0377.

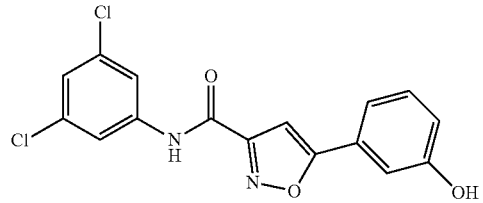

KSC-392-067

N-(3,5-Dichlorophenyl)-5-(3-hydroxyphenyl)isoxazole-3-carboxamide (KSC-392-067): This compound was prepared following the General Procedure (isoxazole amide) 1 using 5-(3-hydroxyphenyl)isoxazole-3-carboxylic acid (100 mg, 0.487 mmol) and 3,5-dichloroaniline (79 mg, 0.487 mmol). Yield: 48 mg (28%); 96.2% purity. $^1$H NMR (400 MHz, Acetone-$d_6$) δ 9.91 (s, 1H), 7.99 (d, J=1.9 Hz, 2H), 7.47-7.34 (m, 3H), 7.25 (t, J=1.8 Hz, 1H), 7.21 (s, 1H), 7.02 (ddd, J=7.7, 2.4, 1.4 Hz, 1H); $^{13}$C NMR (101 MHz, Acetone-$d_6$) δ 172.66, 160.25, 158.95, 158.38, 141.34, 135.68, 131.41, 131.41, 128.71, 124.76, 119.50, 119.50, 118.96, 118.15, 113.41, 100.32; HRMS (ESI-TOF) m/z: [M–H]$^-$ Calcd for $C_{16}H_9Cl_2N_2O_3$ 346.9995, found: 347.0005.

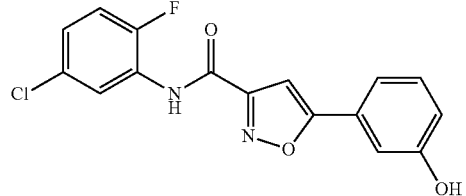

KSC-392-068

N-(5-Chloro-2-fluorophenyl)-5-(3-hydroxyphenyl)isoxazole-3-carboxamide (KSC-392-068): This compound was prepared following the General Procedure (isoxazole amide) 1 using 5-(3-hydroxyphenyl)isoxazole-3-carboxylic acid (100 mg, 0.487 mmol) and 5-chloro-2-fluoroaniline (71 mg, 0.487 mmol). Yield: 40 mg (24%); 98.5% purity. $^1$H NMR (400 MHz, DMSO-$d_6$) δ 10.62 (s, 1H), 9.90 (s, 1H), 7.80-7.73 (m, 1H), 7.43 (s, 1H), 7.42-7.33 (m, 4H), 7.33-7.29 (m, 1H), 6.95 (ddd, J=7.5, 2.4, 1.6 Hz, 1H); $^{13}$C NMR (101 MHz, DMSO-$d_6$) δ 170.90, 158.96, 157.93, 157.42, 154.18 (d, J=248.2 Hz), 130.52, 127.83 (d, J=3.3 Hz), 127.20, 127.03 (d, J=7.9 Hz), 126.01, 125.84, 118.05, 117.56 (d, J=21.8 Hz), 116.73, 112.19, 99.94; FIRMS (ESI-TOF) m/z: [M−H]$^−$ Calcd for $C_{16}H_9ClFN_2O_3$ 331.0291, found: 331.0276.

KSC-392-069

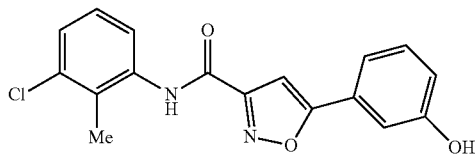

N-(3-chloro-2-methylphenyl)-5-(3-hydroxyphenyl)isoxazole-3-carboxamide (KSC-392-069): This compound was prepared following the General Procedure (isoxazole amide) 1 using 5-(3-hydroxyphenyl)isoxazole-3-carboxylic acid (100 mg, 0.487 mmol) and 3-chloro-2-methylaniline (69 mg, 0.487 mmol). Yield: 35 mg (22%); 100% purity. $^1$H NMR (400 MHz, DMSO-$d_6$) δ 10.51 (s, 1H), 9.89 (s, 1H), 7.43-7.38 (m, 3H), 7.38-7.34 (m, 1H), 7.32-7.30 (m, 1H), 7.30-7.24 (m, 1H), 6.95 (ddd, J=7.4, 2.5, 1.6 Hz, 1H), 2.27 (s, 3H); $^{13}$C NMR (101 MHz, DMSO-$d_6$) δ 170.74, 159.36, 157.95, 157.52, 136.73, 133.81, 132.06, 130.52, 127.29, 127.22, 126.97, 125.77, 117.99, 116.69, 112.18, 99.96, 15.20; HRMS (ESI-TOF) m/z: [M−H]$^−$ Calcd for $C_{17}H_{12}ClN_2O_3$ 327.0542, found: 327.0554.

KSC-392-072

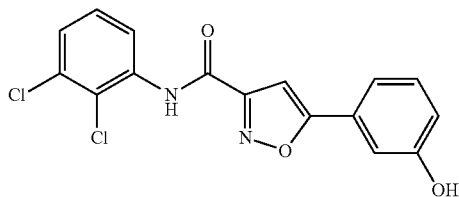

N-(2,3-Dichlorophenyl)-5-(3-hydroxyphenyl)isoxazole-3-carboxamide (KSC-392-072): This compound was prepared following the General Procedure (isoxazole amide) 1 using 5-(3-hydroxyphenyl)isoxazole-3-carboxylic acid (80 mg, 0.390 mmol) and 2,3-dichloroaniline (63 mg, 0.487 mmol). Yield: 33 mg (24%); 100% purity. $^1$H NMR (400 MHz, DMSO-$d_6$) δ 10.54 (s, 1H), 9.90 (s, 1H), 7.68 (dd, J=8.0, 1.2 Hz, 1H), 7.61 (dd, J=8.1, 1.5 Hz, 1H), 7.48-7.34 (m, 4H), 7.32 (t, J=2.0 Hz, 1H), 6.95 (ddd, J=7.6, 2.5, 1.5 Hz, 1H); $^{13}$C NMR (101 MHz, DMSO-$d_6$) δ 171.01, 159.01, 157.91, 157.31, 135.82, 132.03, 130.56, 128.28, 128.25, 127.62, 127.20, 126.31, 118.05, 116.75, 112.15, 99.98; HRMS (ESI-TOF) m/z: [M−H]$^−$ Calcd for $C_{16}H_9Cl_2N_2O_3$ 346.9995, found: 347.0001.

KSC-392-073

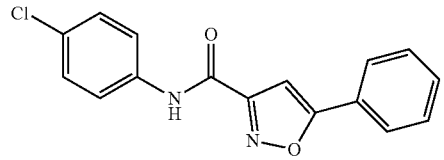

N-(4-Chlorophenyl)-5-phenylisoxazole-3-carboxamide (KSC-392-073): This compound was prepared following the General Procedure (isoxazole amide) 1 using 5-phenylisoxazole-3-carboxylic acid (80 mg, 0.423 mmol) and 4-chloroaniline (54 mg, 0.423 mmol). Yield: 72 mg (57%); 99.3% purity. $^1$H NMR (400 MHz, DMSO-$d_6$) δ 10.91 (s, 1H), 8.00-7.93 (m, 2H), 7.89-7.82 (m, 2H), 7.61-7.53 (m, 3H), 7.50 (s, 1H), 7.47-7.41 (m, 2H); $^{13}$C NMR (101 MHz, DMSO-$d_6$) δ 170.61, 159.72, 157.26, 136.96, 130.91, 129.30, 128.62, 128.09, 126.17, 125.80, 122.09, 100.11; HRMS (ESI-TOF) m/z: [M−H]$^−$ Calcd for $C_{16}H_{11}ClN_2O_2$ 297.0436, found: 297.0439.

KSC-392-074

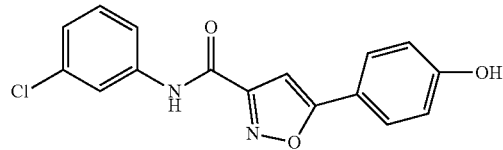

N-(3-Chlorophenyl)-5-(4-hydroxyphenyl)isoxazole-3-carboxamide (KSC-392-074): This compound was prepared following the General Procedure (isoxazole amide) 1 using 5-(4-hydroxyphenyl)isoxazole-3-carboxylic acid (80 mg, 0.390 mmol) and 3-chloroaniline (50 mg, 0.390 mmol). Yield: 67 mg (59%); 98.9% purity. $^1$H NMR (400 MHz, DMSO-$d_6$) δ 10.89 (s, 1H), 10.19 (s, 1H), 7.98 (t, J=2.0 Hz, 1H), 7.82-7.73 (m, 3H), 7.40 (t, J=8.1 Hz, 1H), 7.24 (s, 1H), 7.20 (ddd, J=8.0, 2.1, 0.9 Hz, 1H), 6.96-6.90 (m, 2H); $^{13}$C NMR (101 MHz, DMSO-$d_6$) δ 171.20, 159.92, 159.50, 157.66, 139.52, 133.01, 130.38, 127.71, 124.07, 120.00, 118.94, 117.34, 116.07, 97.87; HRMS (ESI-TOF) m/z: [M−H]$^−$ Calcd for $C_{16}H_{10}ClN_2O_3$ 313.0385, found: 313.0374.

KSC-392-075

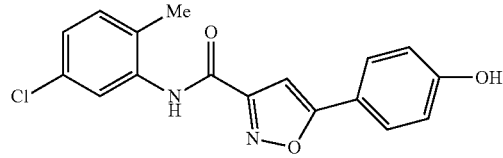

N-(5-Chloro-2-methylphenyl)-5-(4-hydroxyphenyl)isoxazole-3-carboxamide (KSC-392-075): This compound was prepared following the General Procedure (isoxazole amide) 1 using 5-(4-hydroxyphenyl)isoxazole-3-carboxylic acid (80 mg, 0.390 mmol) and 5-chloro-2-methylaniline (55 mg, 0.390 mmol). Yield: 48 mg (38%); 93.5% purity. $^{1}$H NMR (400 MHz, DMSO-d$_{6}$) δ 10.78 (s, 1H), 9.90 (s, 1H), 7.94 (d, J=2.5 Hz, 1H), 7.72 (dd, J=9.0, 2.6 Hz, 1H), 7.43-7.32 (m, 3H), 7.34-7.27 (m, 1H), 7.18 (d, J=9.1 Hz, 1H), 6.95 (ddd, J=7.2, 2.5, 1.8 Hz, 1H), 3.85 (s, 3H); $^{13}$C NMR (101 MHz, DMSO-d$_{6}$) δ 171.20, 159.90, 159.25, 157.55, 136.54, 132.14, 131.88, 129.89, 127.69, 126.03, 125.54, 117.38, 116.06, 97.85, 17.21; HRMS (ESI-TOF) m/z: [M−H]$^{−}$ Calcd for C$_{17}$H$_{12}$ClN$_{2}$O$_{3}$ 327.0542, found: 327.0506.

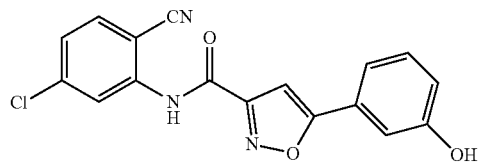

KSC-392-077

N-(5-Chloro-2-cyanophenyl)-5-(3-hydroxyphenyl)isoxazole-3-carboxamide (KSC-392-077): This compound was prepared following the General Procedure (isoxazole amide) 1 using 5-(3-hydroxyphenyl)isoxazole-3-carboxylic acid (80 mg, 0.390 mmol) and 2-amino-4-chlorobenzonitrile (59 mg, 0.390 mmol). Yield: 10 mg (7%); 96.7% purity. $^{1}$H NMR (400 MHz, DMSO-d$_{6}$) δ 11.15 (s, 1H), 9.91 (s, 1H), 7.96 (d, J=8.5 Hz, 1H), 7.81 (d, J=2.1 Hz, 1H), 7.57 (dd, J=8.4, 2.1 Hz, 1H), 7.46 (s, 1H), 7.45-7.38 (m, 1H), 7.42-7.33 (m, 1H), 7.36-7.30 (m, 1H), 6.96 (ddd, J=7.8, 2.4, 1.3 Hz, 1H); $^{13}$C NMR (101 MHz, DMSO-d$_{6}$) δ 171.09, 158.90, 157.93, 157.69, 140.71, 138.26, 134.67, 130.53, 127.16, 126.79, 126.34, 118.09, 116.77, 115.95, 112.21, 107.70, 100.04; HRMS (ESI-TOF) m/z: [M+H]$^{+}$ Calcd for C$_{17}$H$_{11}$ClN$_{3}$O$_{3}$ 340.0484, found: 340.0475.

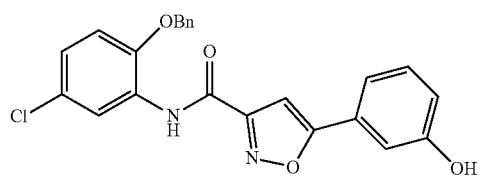

KSC-392-078

N-(2-(Benzyloxy)-5-chlorophenyl)-5-(3-hydroxyphenyl)isoxazole-3-carboxamide (KSC-392-078): This compound was prepared following the General Procedure (isoxazole amide) 1 using 5-(3-hydroxyphenyl)isoxazole-3-carboxylic acid (80 mg, 0.390 mmol) and 2-(benzyloxy)-5-chloroaniline (91 mg, 0.390 mmol). Yield: 73 mg (42%); 94% purity. $^{1}$H NMR (400 MHz, DMSO-d$_{6}$) δ 9.91 (s, 1H), 9.63 (s, 1H), 8.13 (s, 1H), 7.53-7.49 (m, 2H), 7.44-7.31 (m, 7H), 7.20 (d, J=1.5 Hz, 2H), 6.96 (ddd, J=7.7, 2.5, 1.4 Hz, 1H), 5.24 (s, 2H); $^{13}$C NMR (101 MHz, DMSO-d$_{6}$) δ 171.36, 159.14, 157.94, 156.56, 147.48, 136.30, 130.48, 128.46, 128.02, 127.58, 127.41, 127.16, 124.81, 124.40, 121.04, 118.10, 116.77, 114.32, 112.25, 99.74, 70.39; HRMS (ESI-TOF) m/z: [M+H]$^{+}$ Calcd for C$_{23}$H$_{18}$ClN$_{2}$O$_{4}$ 421.0950, found: 421.0939.

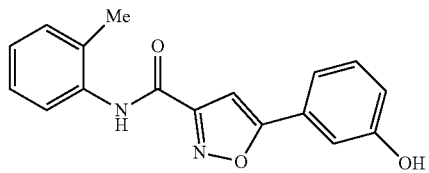

KSC-392-080

5-(3-Hydroxyphenyl)-N-(o-tolyl)isoxazole-3-carboxamide (KSC-392-080): This compound was prepared following the General Procedure (isoxazole amide) 1 using 5-(3-hydroxyphenyl)isoxazole-3-carboxylic acid (80 mg, 0.390 mmol) and o-toluidine (42 mg, 0.390 mmol). Yield: 45 mg (40%); 99.5% purity. $^{1}$H NMR (400 MHz, DMSO-d$_{6}$) δ 10.24 (s, 1H), 9.90 (s, 1H), 7.44-7.32 (m, 4H), 7.34-7.26 (m, 2H), 7.29-7.15 (m, 2H), 6.95 (ddd, J=7.4, 2.5, 1.7 Hz, 1H), 2.26 (s, 3H); $^{13}$C NMR (101 MHz, DMSO-d$_{6}$) δ 170.64, 159.58, 157.93, 157.27, 135.14, 133.39, 130.51, 130.37, 127.34, 126.39, 126.22, 126.08, 117.95, 116.69, 112.16, 99.92, 17.72; FIRMS (ESI-TOF) m/z: [M+H]$^{+}$ Calcd for C$_{17}$H$_{15}$N$_{2}$O$_{3}$ 295.1077, found: 295.1081.

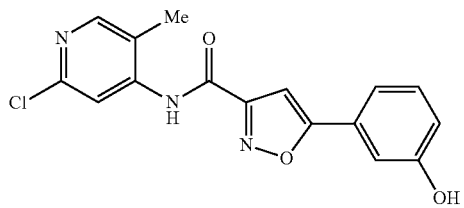

KSC-392-141

N-(2-Chloro-5-methylpyridin-4-yl)-5-(3-hydroxyphenyl)isoxazole-3-carboxamide (KSC-392-141): This compound was prepared following the General Procedure (isoxazole amide) 1 using 5-(3-hydroxyphenyl)isoxazole-3-carboxylic acid (25 mg, 0.122 mmol) and 2-chloro-5-methylpyridin-4-amine (17 mg, 0.122 mmol). Yield: 3 mg (7%); 96.2% purity. $^{1}$H NMR (500 MHz, DMSO-d$_{6}$) δ 10.56 (s, 1H), 9.50 (s, 1H), 8.44 (d, J=2.3 Hz, 1H), 8.00 (d, J=2.3 Hz, 1H), 7.42 (dd, J=8.4, 2.2 Hz, 1H), 7.34 (d, J=2.2 Hz, 1H), 7.29 (s, 1H), 7.10 (d, J=8.5 Hz, 1H), 3.85 (s, 3H), 2.45 (s, 3H); $^{13}$C NMR (126 MHz, DMSO-d$_{6}$) δ 171.16, 159.11, 157.84, 152.42, 150.12, 146.98, 144.89, 133.19, 132.23, 127.85, 118.94, 117.93, 112.51, 98.58, 55.74, 20.66; HRMS (ESI-TOF) m/z: [M+H]$^{+}$ Calcd for C$_{16}$H$_{13}$ClN$_{3}$O$_{3}$ 330.0640, found: 330.0682.

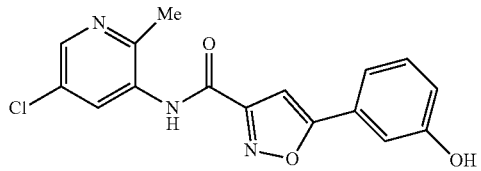

KSC-392-125

N-(5-Chloro-2-methylpyridin-3-yl)-5-(3-hydroxyphenyl)isoxazole-3-carboxamide (KSC-392-125): This compound was prepared following the General Procedure (isoxazole amide) 1 using 5-(3-hydroxyphenyl)isoxazole-3-carboxylic acid (28 mg, 0.136 mmol) and 2 5-chloro-2-methylpyridin-3-amine (19 mg, 0.136 mmol). Yield: 16 mg (34%); 96.2% purity. $^1$H NMR (500 MHz, DMSO-d$_6$) δ 10.61 (s, 1H), 9.92 (s, 1H), 8.44 (d, J=2.3 Hz, 1H), 8.00 (d, J=2.4 Hz, 1H), 7.44 (s, 1H), 7.41 (dt, J=7.7, 1.4 Hz, 1H), 7.37 (t, J=7.8 Hz, 1H), 7.32 (dd, J=2.4, 1.6 Hz, 1H), 6.95 (ddd, J=7.8, 2.5, 1.2 Hz, 1H), 2.46 (s, 3H); $^{13}$C NMR (126 MHz, DMSO-d$_6$) δ 170.95, 159.17, 157.99, 157.70, 152.44, 144.94, 133.21, 132.19, 130.63, 127.84, 127.27, 118.10, 116.80, 112.21, 100.11, 20.67; HRMS (ESI-TOF) m/z: [M+H]$^+$ Calcd for C$_{16}$H$_{13}$ClN$_3$O$_3$ 330.0640, found: 330.0595.

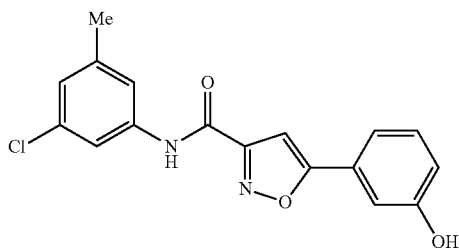

KSC-392-143

N-(3-Chloro-5-methylphenyl)-5-(3-hydroxyphenyl)isoxazole-3-carboxamide (KSC-392-143): This compound was prepared following the General Procedure (isoxazole amide) 1 using 5-(3-hydroxyphenyl)isoxazole-3-carboxylic acid (25 mg, 0.122 mmol) and 3-chloro-5-methylaniline (17 mg, 0.122 mmol). Yield: 9 mg (24%); 100% purity. $^1$H NMR (500 MHz, DMSO-d$_6$) δ 10.85 (s, 1H), 9.92 (s, 1H), 7.76-7.74 (m, 1H), 7.59 (s, 1H), 7.41 (s, 1H), 7.40-7.34 (m, 2H), 7.31 (dd, J=2.5, 1.5 Hz, 1H), 7.06 (s, 2H), 6.95 (ddd, J=7.6, 2.5, 1.5 Hz, 1H), 2.31 (s, 3H); $^{13}$C NMR (126 MHz, DMSO-d$_6$) δ 170.78, 159.68, 157.99, 157.48, 140.38, 139.26, 132.78, 130.63, 127.29, 124.75, 119.52, 118.09, 117.25, 116.78, 112.21, 100.07, 20.99; HRMS (ESI-TOF) m/z: [M+H]$^+$ Calcd for C$_{17}$H$_{14}$ClN$_2$O$_3$ 329.0687, found: 329.0742.

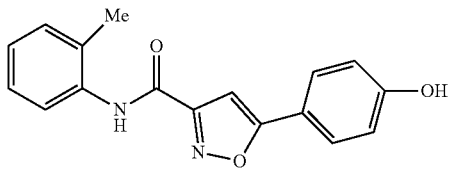

KSC-392-081

5-(4-Hydroxyphenyl)-N-(o-tolyl)isoxazole-3-carboxamide (KSC-392-081): This compound was prepared following the General Procedure (isoxazole amide) 1 using 5-(4-hydroxyphenyl)isoxazole-3-carboxylic acid (12 mg, 0.058 mmol) and o-toluidine (6 mg, 0.058 mmol). Yield: 12 mg (67%); 99.5% purity. $^1$H NMR (400 MHz, DMSO-d$_6$) δ 10.19 (s, 1H), 10.17 (s, 1H), 7.83-7.74 (m, 2H), 7.42-7.36 (m, 1H), 7.31-7.27 (m, 1H), 7.26-7.15 (m, 3H), 6.96-6.89 (m, 2H), 2.25 (s, 3H); $^{13}$C NMR (101 MHz, DMSO-d$_6$) δ 171.04, 159.83, 159.48, 157.44, 135.18, 133.34, 130.35, 127.65, 126.33, 126.19, 126.06, 117.43, 116.03, 97.82, 17.71; HRMS (ESI-TOF) m/z: [M+H]$^+$ Calcd for C$_{17}$H$_{15}$N$_2$O$_3$ 295.1077, found: 295.1066.

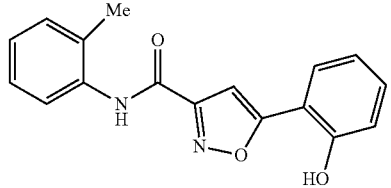

KSC-392-082

5-(2-Hydroxyphenyl)-N-(o-tolyl)isoxazole-3-carboxamide (KSC-392-082): This compound was prepared following the General Procedure (isoxazole amide) 1 using 5-(2-hydroxyphenyl)isoxazole-3-carboxylic acid (80 mg, 0.390 mmol) and o-toluidine (42 mg, 0.390 mmol). Yield: 40 mg (35%); 98% purity. $^1$H NMR (400 MHz, DMSO-d$_6$) δ 10.80 (s, 1H), 10.25 (s, 1H), 7.85 (dd, J=7.9, 1.7 Hz, 1H), 7.43-7.34 (m, 2H), 7.32-7.25 (m, 1H), 7.26-7.17 (m, 3H), 7.09 (d, J=8.1 Hz, 1H), 7.04-6.95 (m, 1H), 2.26 (s, 3H); $^{13}$C NMR (101 MHz, DMSO-d$_6$) δ 167.52, 159.37, 157.48, 155.02, 135.21, 133.44, 131.93, 130.36, 126.76, 126.37, 126.29, 126.07, 119.46, 116.60, 113.28, 102.20, 17.74; HRMS (ESI-TOF) m/z: [M+H]$^+$ Calcd for C$_{17}$H$_{15}$N$_2$O$_3$ 295.1077, found: 295.1068.

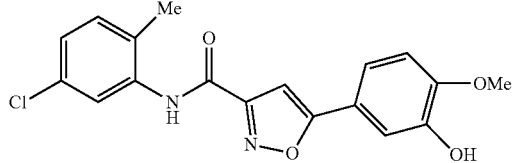

KSC-392-086

N-(5-Chloro-2-methylphenyl)-5-(3-hydroxy-4-methoxyphenyl)isoxazole-3-carboxamide (KSC-392-086): This compound was prepared following the General Procedure (isoxazole amide) 1 using 5-(3-hydroxy-4-methoxyphenyl)isoxazole-3-carboxylic acid (11 mg, 0.047 mmol) and 5-chloro-2-methylaniline (7 mg, 0.047 mmol). Yield: 8 mg (47%); 99.8% purity. $^1$H NMR (400 MHz, DMSO-d$_6$) δ 10.28 (s, 1H), 9.49 (s, 1H), 7.52 (d, J=2.2 Hz, 1H), 7.41 (dd, J=8.4, 2.2 Hz, 1H), 7.36-7.29 (m, 2H), 7.30-7.22 (m, 2H), 7.09 (d, J=8.5 Hz, 1H), 3.85 (s, 3H), 2.24 (s, 3H); $^{13}$C NMR (101 MHz, DMSO-d$_6$) δ 170.95, 159.27, 157.49, 150.04, 146.96, 136.52, 132.16, 131.88, 129.87, 126.04, 125.54, 117.80, 112.50, 98.44, 55.70, 17.20; HRMS (ESI-TOF) m/z: [M+H]$^+$ Calcd for C$_{18}$H$_{16}$ClN$_2$O$_4$ 359.0793, found: 359.0789.

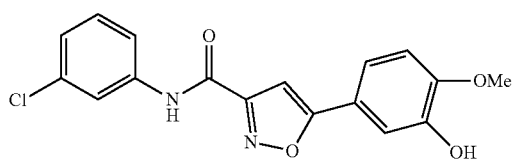

KSC-392-087

N-(3-Chlorophenyl)-5-(3-hydroxy-4-methoxyphenyl)isoxazole-3-carboxamide (KSC-392-087): This compound was prepared following the General Procedure (isoxazole amide) 1 using 5-(3-hydroxy-4-methoxyphenyl)isoxazole-3-carboxylic acid (10 mg, 0.043 mmol) and 3-chloroaniline (5 mg, 0.043 mmol). Yield: 3 mg (23%); 99.2% purity. $^1$H NMR (400 MHz, DMSO-$d_6$) δ 10.89 (s, 1H), 9.50 (s, 1H), 8.00-7.94 (m, 1H), 7.75 (ddd, J=8.3, 2.0, 0.9 Hz, 1H), 7.41 (ddd, J=8.1, 5.0, 2.8 Hz, 2H), 7.33 (d, J=2.2 Hz, 1H), 7.27 (s, 1H), 7.22 (ddd, J=8.0, 2.1, 0.9 Hz, 1H), 7.09 (d, J=8.5 Hz, 1H), 3.85 (s, 3H); $^{13}$C NMR (101 MHz, DMSO-$d_6$) δ 171.16, 159.72, 157.80, 150.28, 147.20, 139.70, 133.18, 130.62, 124.29, 120.15, 119.14, 119.12, 118.01, 112.71, 112.70, 98.66, 55.91; HRMS (ESI-TOF) m/z: [M+H]$^+$ Calcd for $C_{17}H_{14}ClN_2O_4$ 345.0637, found: 345.0630.

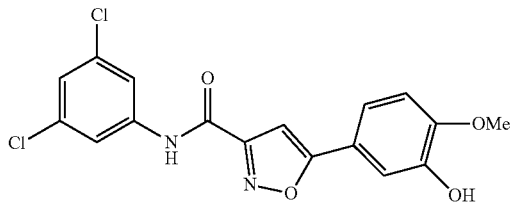

KSC-392-099

N-(3,5-Dichlorophenyl)-5-(3-hydroxy-4-methoxyphenyl) isoxazole-3-carboxamide (KSC-392-099): This compound was prepared following the General Procedure (isoxazole amide) 1 using 5-(3-hydroxy-4-methoxyphenyl)isoxazole-3-carboxylic acid (25 mg, 0.106 mmol) and 3,5-dichloroaniline (17 mg, 0.106 mmol). Yield: 2 mg (6%); 93.9% purity. $^1$H NMR (500 MHz, DMSO-$d_6$) δ 11.08 (bs, 2H), 7.92 (d, J=1.9 Hz, 2H), 7.42 (dd, J=8.4, 2.2 Hz, 1H), 7.40 (t, J=1.9 Hz, 1H), 7.33 (d, J=2.2 Hz, 1H), 7.28 (s, 1H), 7.10 (d, J=8.5 Hz, 1H), 3.85 (s, 3H); $^{13}$C NMR (126 MHz, DMSO-$d_6$) δ 171.18, 159.42, 157.94, 150.17, 147.03, 140.59, 134.11, 118.90, 112.51, 98.61, 55.76; HRMS (ESI-TOF) m/z: [M+H]$^+$ Calcd for $C_{17}H_{13}Cl_2N_2O_4$ 379.0247, found: 379.0237.

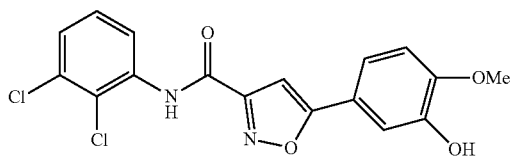

KSC-392-101

N-(2,3-Dichlorophenyl)-5-(3-hydroxy-4-methoxyphenyl) isoxazole-3-carboxamide (KSC-392-101): This compound was prepared following the General Procedure (isoxazole amide) 1 using 5-(3-hydroxy-4-methoxyphenyl)isoxazole-3-carboxylic acid (25 mg, 0.106 mmol) and 2,3-dichloroaniline (17 mg, 0.106 mmol). Yield: 7 mg (18%); 100% purity. $^1$H NMR (500 MHz, DMSO-$d_6$) δ 10.50 (s, 1H), 9.49 (s, 1H), 7.68 (dd, J=8.1, 1.5 Hz, 1H), 7.60 (dd, J=8.1, 1.5 Hz, 1H), 7.48-7.38 (m, 2H), 7.34 (d, J=2.2 Hz, 1H), 7.30 (s, 1H), 7.10 (d, J=8.5 Hz, 1H), 3.85 (s, 3H); $^{13}$C NMR (126 MHz, DMSO-$d_6$) δ 171.27, 159.00, 157.48, 150.12, 146.96, 135.91, 132.07, 127.58, 118.92, 98.51, 55.73; HRMS (ESI-TOF) m/z: [M+H]$^+$ Calcd for $C_{17}H_{13}Cl_2N_2O_4$ 379.0247, found: 379.0251.

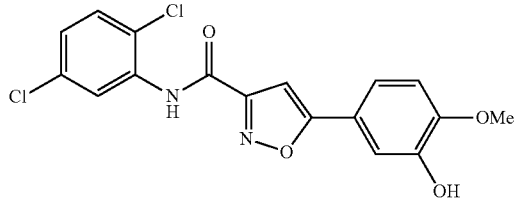

KSC-392-120-P1

N-(2,5-Dichlorophenyl)-5-(3-hydroxy-4-methoxyphenyl) isoxazole-3-carboxamide (KSC-392-120-P1): This compound was prepared following the General Procedure (isoxazole amide) 1 using 5-(3-hydroxy-4-methoxyphenyl) isoxazole-3-carboxylic acid (25 mg, 0.106 mmol) and 2,5-dichloroaniline (17 mg, 0.106 mmol). Yield: 11 mg (26%); 98% purity. $^1$H NMR (400 MHz, Acetone-$d_6$) δ 9.32 (s, 1H), 8.49 (d, J=2.5 Hz, 1H), 7.59 (d, J=8.6 Hz, 1H), 7.47 (dd, J=8.4, 2.2 Hz, 1H), 7.43 (d, J=2.2 Hz, 1H), 7.28 (dd, J=8.6, 2.5 Hz, 1H), 7.18 (s, 1H), 7.14 (d, J=8.4 Hz, 1H), 3.94 (s, 3H); $^{13}$C NMR (101 MHz, Acetone-$d_6$) δ 173.45, 160.01, 151.02, 148.11, 136.16, 133.79, 131.48, 126.39, 123.28, 122.75, 120.56, 119.14, 113.42, 112.85, 98.73, 56.44; FIRMS (ESI-TOF) m/z: [M+H]$^+$ Calcd for $C_{17}H_{13}Cl_2N_2O_4$ 379.0247, found: 379.0252.

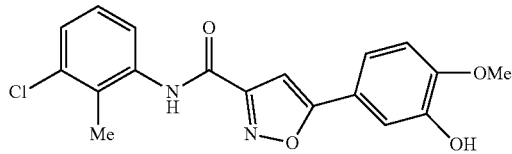

KSC-392-139

N-(3-Chloro-2-methylphenyl)-5-(3-hydroxy-4-methoxyphenyl)isoxazole-3-carboxamide (KSC-392-139): This compound was prepared following the General Procedure (isoxazole amide) 1 using 5-(3-hydroxy-4-methoxyphenyl) isoxazole-3-carboxylic acid (25 mg, 0.106 mmol) and 3-chloro-2-methylaniline (15 mg, 0.106 mmol). Yield: 13 mg (33%); 95.7% purity. $^1$H NMR (500 MHz, DMSO-$d_6$) δ 10.52 (s, 1H), 9.49 (s, 1H), 7.41 (ddd, J=8.0, 4.6, 1.8 Hz, 2H), 7.35 (dd, J=8.0, 1.3 Hz, 1H), 7.33 (d, J=2.2 Hz, 1H), 7.31-7.24 (m, 2H), 7.09 (d, J=8.5 Hz, 1H), 3.85 (s, 3H), 2.26 (s, 3H); $^{13}$C NMR (126 MHz, DMSO-$d_6$) δ 170.99, 159.37, 157.71, 150.07, 146.97, 136.81, 133.87, 132.15, 127.29, 127.07, 125.88, 119.03, 117.89, 112.50, 98.56, 55.73, 15.31; HRMS (ESI-TOF) m/z: [M+H]$^+$ Calcd for $C_{18}H_{16}ClN_2O_4$ 359.0793, found: 359.0881.

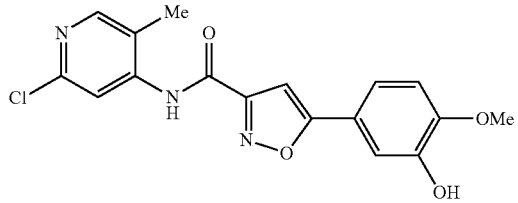

KSC-392-140

N-(2-Chloro-5-methylpyridin-4-yl)-5-(3-hydroxy-4-methoxyphenyl)isoxazole-3-carboxamide (KSC-392-140):

This compound was prepared following the General Procedure (isoxazole amide) 1 using 5-(3-hydroxy-4-methoxyphenyl)isoxazole-3-carboxylic acid (25 mg, 0.106 mmol) and 2-chloro-5-methylpyridin-4-amine (15 mg, 0.106 mmol). Yield: 2 mg (4%); 100% purity. $^1$H NMR (500 MHz, DMSO-$d_6$) δ 10.33 (s, 1H), 9.50 (s, 1H), 8.37-8.20 (m, 1H), 7.82 (s, 1H), 7.42 (dd, J=8.4, 2.2 Hz, 1H), 7.34 (d, J=2.2 Hz, 1H), 7.33 (s, 1H), 7.10 (d, J=8.5 Hz, 1H), 3.85 (s, 3H), 2.28 (s, 3H); $^{13}$C NMR (126 MHz, DMSO-$d_6$) δ 171.31, 158.99, 157.83, 150.17, 148.06, 146.99, 145.30, 125.98, 118.86, 117.61, 112.51, 98.60, 55.75, 14.15; HRMS (ESI-TOF) m/z: [M+H]$^+$ Calcd for $C_{17}H_{15}ClN_3O_4$ 360.0746, found: 360.0803.

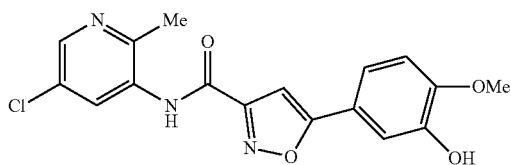

KSC-392-142

N-(5-Chloro-2-methylpyridin-3-yl)-5-(3-hydroxy-4-methoxyphenyl)isoxazole-3-carboxamide (KSC-392-142): This compound was prepared following the General Procedure (isoxazole amide) 1 using 5-(3-hydroxy-4-methoxyphenyl)isoxazole-3-carboxylic acid (25 mg, 0.106 mmol) and 5-chloro-2-methylpyridin-3-amine (15 mg, 0.106 mmol). Yield: 9 mg (23%); 98.3% purity. $^1$H NMR (500 MHz, DMSO-$d_6$) δ 10.56 (s, 1H), 9.50 (bs, 1H), 8.44 (d, J=2.3 Hz, 1H), 8.00 (d, J=2.3 Hz, 1H), 7.42 (dd, J=8.4, 2.2 Hz, 1H), 7.34 (d, J=2.2 Hz, 1H), 7.29 (s, 1H), 7.10 (d, J=8.5 Hz, 1H), 3.85 (s, 3H), 2.45 (s, 3H); $^{13}$C NMR (126 MHz, DMSO-$d_6$) δ 171.16, 159.11, 157.84, 152.42, 150.12, 146.98, 144.89, 133.19, 132.23, 127.85, 118.94, 117.93, 112.51, 98.58, 55.74, 20.66; HRMS (ESI-TOF) m/z: [M+H]$^+$ Calcd for $C_{17}H_{15}ClN_3O_4$ 360.0746, found: 360.0816.

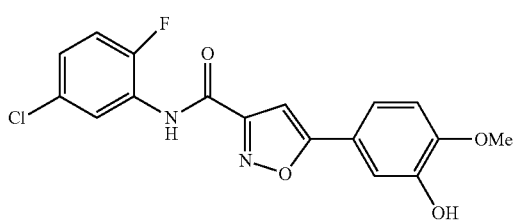

KSC-392-121-P1

N-(5-Chloro-2-fluorophenyl)-5-(3-hydroxy-4-methoxyphenyl)isoxazole-3-carboxamide (KSC-392-121-P1): This compound was prepared following the General Procedure (isoxazole amide) 1 using 5-(3-hydroxy-4-methoxyphenyl) isoxazole-3-carboxylic acid (25 mg, 0.106 mmol) and 5-chloro-2-fluoroaniline (15 mg, 0.106 mmol). Yield: 8 mg (20%); 96% purity. $^1$H NMR (500 MHz, Acetone-$d_6$) δ 9.32 (s, 1H), 8.29 (dd, J=6.8, 2.6 Hz, 1H), 7.47 (dd, J=8.4, 2.2 Hz, 1H), 7.42 (d, J=2.2 Hz, 1H), 7.34 (dd, J=10.3, 8.8 Hz, 1H), 7.28 (ddd, J=8.8, 4.5, 2.6 Hz, 1H), 7.16 (s, 1H), 7.14 (d, J=8.4 Hz, 1H), 3.94 (s, 3H); $^{13}$C NMR (126 MHz, Acetone-$d_6$) δ 173.14, 129.81 (d, J=3.4 Hz), 126.43 (d, J=7.9 Hz), 123.91, 120.60, 119.11, 117.75 (d, J=21.4 Hz), 113.40, 112.81, 98.86, 56.43; HRMS (ESI-TOF) m/z: [M+H]$^+$ Calcd for $C_{17}H_{13}ClFN_2O_4$ 363.0542, found: 363.0549.

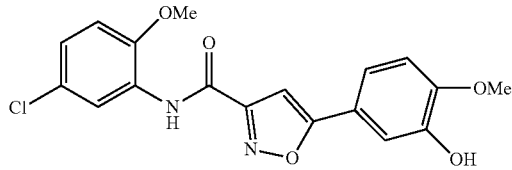

KSC-392-106

N-(5-Chloro-2-methoxyphenyl)-5-(3-hydroxy-4-methoxyphenyl)isoxazole-3-carboxamide (KSC-392-106): This compound was prepared following the General Procedure (isoxazole amide) 1 using 5-(3-hydroxy-4-methoxyphenyl)isoxazole-3-carboxylic acid (25 mg, 0.106 mmol) and 5-chloro-2-methoxyaniline (17 mg, 0.106 mmol). Yield: 13 mg (32%); 99.7% purity. $^1$H NMR (500 MHz, DMSO-$d_6$) δ 9.52 (s, 1H), 9.50 (s, 1H), 8.12 (d, J=2.7 Hz, 1H), 7.42 (dd, J=8.4, 2.2 Hz, 1H), 7.33 (d, J=2.2 Hz, 1H), 7.31 (s, 1H), 7.24 (dd, J=8.8, 2.6 Hz, 1H), 7.16 (d, J=8.8 Hz, 1H), 7.09 (d, J=8.5 Hz, 1H), 3.90 (s, 3H), 3.85 (s, 3H); $^{13}$C NMR (126 MHz, DMSO) δ 171.71, 159.28, 156.95, 150.32, 148.73, 147.13, 127.30, 125.09, 124.16, 121.08, 119.05, 118.13, 112.99, 112.67, 112.62, 98.48, 56.58, 55.88; HRMS (ESI-TOF) m/z: [M+H]$^+$ Calcd for $C_{18}H_{16}ClN_2O_5$ 375.0742, found: 375.0711.

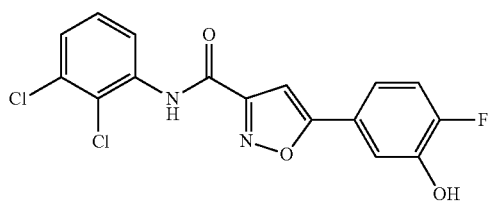

KSC-392-104

N-(2,3-Dichlorophenyl)-5-(4-fluoro-3-hydroxyphenyl) isoxazole-3-carboxamide (KSC-392-104): This compound was prepared following the General Procedure (isoxazole amide) 1 using 5-(4-fluoro-3-hydroxyphenyl)isoxazole-3-carboxylic acid (12 mg, 0.024 mmol) and 2,3-dichloroaniline (8.7 mg, 0.024 mmol). Yield: 2 mg (7%); 98.3% purity. $^1$H NMR (500 MHz, DMSO-$d_6$) δ 10.56 (bs, 1H), 10.43 (bs, 1H), 7.67 (dd, J=8.0, 1.5 Hz, 1H), 7.61 (dd, J=8.1, 1.5 Hz, 1H), 7.51 (dd, J=8.2, 2.2 Hz, 1H), 7.48-7.41 (m, 3H), 7.36 (dd, J=11.0, 8.5 Hz, 1H); $^{13}$C NMR (126 MHz, DMSO-$d_6$) δ 170.28, 159.13, 157.32, 152.63 (d, J=246.7 Hz), 145.69 (d, J=13.1 Hz), 135.86, 132.09, 128.35, 128.31, 127.69, 126.38, 122.96 (d, J=3.6 Hz), 117.83 (d, J=7.2 Hz), 117.33 (d, J=19.3 Hz), 114.99 (d, J=3.7 Hz), 99.90; HRMS (ESI-TOF) m/z: [M+Na]$^+$ Calcd for $C_{16}H_9Cl_2FN_2NaO_3$ 388.9866, found: 388.9826.

KSC-392-158

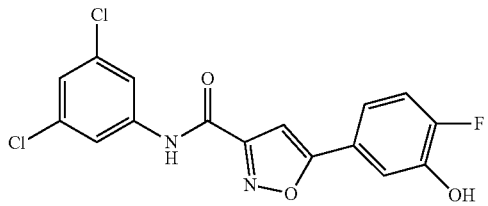

N-(3,5-Dichlorophenyl)-5-(4-fluoro-3-hydroxyphenyl)isoxazole-3-carboxamide (KSC-392-158): This compound was prepared following the General Procedure (isoxazole amide) 1 using 5-(4-fluoro-3-hydroxyphenyl)isoxazole-3-carboxylic acid (25 mg, 0.112 mmol) and 3,5-dichloroaniline (18 mg, 0.112 mmol). Yield: 8 mg (20%); 100% purity. $^1$H NMR (500 MHz, DMSO-$d_6$) δ 11.11 (s, 1H), 10.43 (bs, 1H), 7.93 (d, J=1.9 Hz, 2H), 7.51 (dd, J=8.3, 2.2 Hz, 1H), 7.44 (ddd, J=8.4, 4.3, 2.2 Hz, 1H), 7.42 (s, 1H), 7.40 (t, J=1.9 Hz, 1H), 7.36 (dd, J=11.0, 8.5 Hz, 1H); $^{13}$C NMR (126 MHz, DMSO-$d_6$) δ 170.19, 159.47, 157.67, 152.65 (d, J=246.7 Hz), 145.69 (d, J=13.0 Hz), 140.41, 134.11, 123.75, 122.92 (d, J=3.4 Hz), 118.70, 117.86 (d, J=7.2 Hz), 117.35 (d, J=19.3 Hz), 115.01 (d, J=3.7 Hz), 99.99; HRMS (ESI-TOF) m/z: [M−H]$^+$ Calcd for $C_{16}H_8Cl_2FN_2O_3$ 364.9896, found: 364.9883.

KSC-392-105

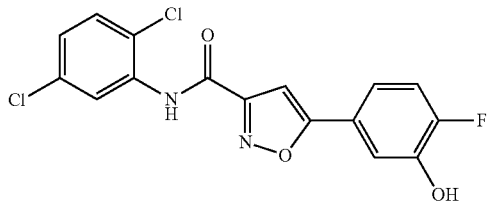

N-(2,5-Dichlorophenyl)-5-(4-fluoro-3-hydroxyphenyl)isoxazole-3-carboxamide (KSC-392-105): This compound was prepared following the General Procedure (isoxazole amide) 1 using 5-(4-fluoro-3-hydroxyphenyl)isoxazole-3-carboxylic acid (17 mg, 0.076 mmol) and 2,5-dichloroaniline (12 mg, 0.076 mmol). Yield: 6 mg (19%); 94.7% purity. $^1$H NMR (500 MHz, DMSO-$d_6$) δ 10.43 (bs, 2H), 7.85 (d, J=2.5 Hz, 1H), 7.63 (d, J=8.6 Hz, 1H), 7.51 (dd, J=8.3, 2.2 Hz, 1H), 7.48-7.39 (m, 3H), 7.35 (dd, J=11.0, 8.5 Hz, 1H); $^{13}$C NMR (126 MHz, DMSO-$d_6$) δ 170.34, 159.06, 157.30, 152.65 (d, J=246.8 Hz), 145.72 (d, J=12.9 Hz), 135.14, 131.68, 131.07, 127.53, 127.29, 126.72, 122.93 (d, J=3.5 Hz), 117.82 (d, J=7.1 Hz), 117.32 (d, J=19.2 Hz), 115.00 (d, J=3.7 Hz), 99.88; HRMS (ESI-TOF) m/z: [M+Na]$^+$ Calcd for $C_{16}H_9Cl_2FN_2NaO_3$ 388.9866, found: 388.9832.

KSC-392-116

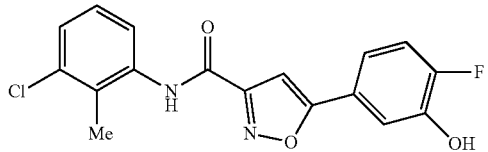

N-(3-Chloro-2-methylphenyl)-5-(4-fluoro-3-hydroxyphenyl)isoxazole-3-carboxamide (KSC-392-116): This compound was prepared following the General Procedure (isoxazole amide) 1 using 5-(4-fluoro-3-hydroxyphenyl)isoxazole-3-carboxylic acid (29 mg, 0.130 mmol) and 3-chloro-2-methylaniline (18 mg, 0.130 mmol). Yield: 14 mg (30%); 97.9% purity. $^1$H NMR (500 MHz, DMSO-$d_6$) δ 10.56 (s, 1H), 10.41 (s, 1H), 7.50 (dd, J=8.3, 2.2 Hz, 1H), 7.47-7.38 (m, 3H), 7.39-7.31 (m, 2H), 7.28 (t, J=8.0 Hz, 1H), 2.26 (s, 3H); $^{13}$C NMR (126 MHz, DMSO-$d_6$) δ 169.99, 158.50 (d, J=247.1 Hz), 153.56, 151.60, 145.66 (d, J=12.8 Hz), 136.75, 133.87, 132.17, 127.33, 127.07, 125.90, 123.05 (d, J=3.4 Hz), 117.80 (d, J=7.2 Hz), 117.33 (d, J=19.2 Hz), 114.95 (d, J=3.6 Hz), 99.95, 15.30; HRMS (ESI-TOF) m/z: [M+H]$^+$ Calcd for $C_{17}H_{13}ClFN_2O_3$ 347.0593, found: 347.0597.

KSC-392-149

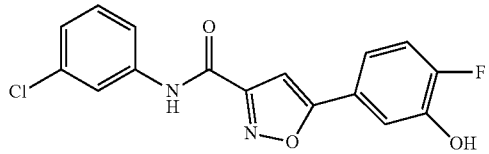

N-(3-Chlorophenyl)-5-(4-fluoro-3-hydroxyphenyl)isoxazole-3-carboxamide (KSC-392-149): This compound was prepared following the General Procedure (isoxazole amide) 1 using 5-(4-fluoro-3-hydroxyphenyl)isoxazole-3-carboxylic acid (25 mg, 0.112 mmol) and 3-chloroaniline (14 mg, 0.112 mmol). Yield: 10 mg (20%); 100% purity. $^1$H NMR (500 MHz, DMSO-$d_6$) δ 10.96 (s, 1H), 10.45 (bs, 1H), 7.97 (t, J=2.0 Hz, 1H), 7.76 (ddd, J=8.3, 2.2, 1.0 Hz, 1H), 7.51 (dd, J=8.3, 2.2 Hz, 1H), 7.47-7.38 (m, 3H), 7.36 (dd, J=11.0, 8.5 Hz, 1H), 7.23 (ddd, J=8.0, 2.1, 0.9 Hz, 1H); $^{13}$C NMR (126 MHz, DMSO-$d_6$) δ 170.03, 159.71, 157.47, 152.64 (d, J=246.8 Hz), 145.74 (d, J=12.8 Hz), 139.51, 133.06, 130.54, 120.01, 119.00, 117.77 (d, J=7.2 Hz), 117.33 (d, J=19.3 Hz), 114.99 (d, J=3.7 Hz), 99.95; HRMS (ESI-TOF) m/z: [M+Na]$^+$ Calcd for $C_{16}H_{10}ClFN_2NaO_3$ 355.0262, found: 355.0252.

KSC-392-150

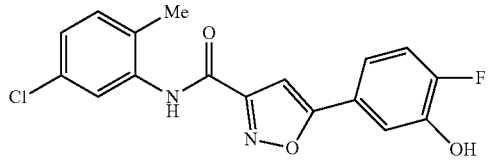

N-(5-Chloro-2-methylphenyl)-5-(4-fluoro-3-hydroxyphenyl)isoxazole-3-carboxamide (KSC-392-150): This compound was prepared following the General Procedure (isoxazole amide) 1 using 5-(4-fluoro-3-hydroxyphenyl)isoxazole-3-carboxylic acid (25 mg, 0.112 mmol) and 5-chloro-2-methylaniline (16 mg, 0.112 mmol). Yield: 7 mg (18%); 100% purity. NMR (500 MHz, DMSO-$d_6$) δ 10.36 (s, 1H), 7.51 (dd, J=7.0, 2.1 Hz, 2H), 7.43 (ddd, J=8.4, 4.3, 2.2 Hz, 1H), 7.40 (s, 1H), 7.39-7.30 (m, 2H), 7.27 (dd, J=8.2, 2.3 Hz, 1H), 2.24 (s, 3H); $^{13}$C NMR (126 MHz, DMSO-$d_6$) δ 169.99, 159.40, 157.31, 152.60 (d, J=246.5 Hz), 145.80 (d, J=12.8 Hz), 136.45, 132.30, 131.92, 129.86, 126.14, 125.67, 117.57 (d, J=7.0 Hz), 117.23 (d, J=19.3 Hz), 114.93 (d, J=3.8 Hz), 99.84, 17.24; HRMS (ESI-TOF) m/z: [M+H]$^+$ Calcd for $C_{17}H_{13}ClFN_2O_3$ 347.0593, found: 347.0599.

KSC-392-155

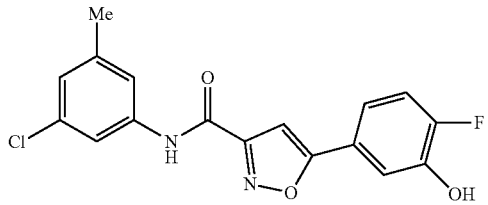

N-(3-Chloro-5-methylphenyl)-5-(4-fluoro-3-hydroxyphenyl)isoxazole-3-carboxamide (KSC-392-155): This compound was prepared following the General Procedure (isoxazole amide) 1 using 5-(4-fluoro-3-hydroxyphenyl)isoxazole-3-carboxylic acid (25 mg, 0.112 mmol) and 3-chloro-5-methylaniline (16 mg, 0.112 mmol). Yield: 10 mg (25%); 99.4% purity. $^1$H NMR (500 MHz, DMSO-$d_6$) δ 10.85 (s, 1H), 10.43 (s, 1H), 7.75 (t, J=2.0 Hz, 1H), 7.59-7.57 (m, 1H), 7.50 (dd, J=8.3, 2.2 Hz, 1H), 7.43 (ddd, J=8.4, 4.3, 2.2 Hz, 1H), 7.39 (s, 1H), 7.35 (dd, J=11.0, 8.5 Hz, 1H), 7.07-7.05 (m, 1H), 2.31 (s, 3H); $^{13}$C NMR (126 MHz, DMSO-$d_6$) δ 170.00, 159.74, 157.43, 152.63 (d, J=246.7 Hz), 145.71 (d, J=12.8 Hz), 140.39, 139.24, 132.79, 124.77, 122.99 (d, J=3.5 Hz), 119.54, 117.80 (d, J=7.2 Hz), 117.34 (d, J=18.8 Hz), 117.26, 114.99 (d, J=3.7 Hz), 99.93, 20.99; HRMS (ESI-TOF) m/z: [M−H]$^-$ Calcd for $C_{17}H_{11}ClFN_2O_3$ 345.0442, found: 345.0434.

KSC-392-156

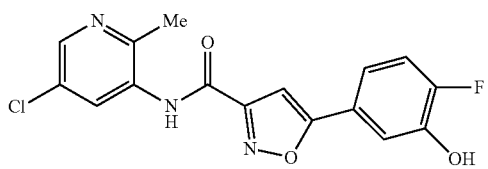

N-(5-Chloro-2-methylpyridin-3-yl)-5-(4-fluoro-3-hydroxyphenyl)isoxazole-3-carboxamide (KSC-392-156): This compound was prepared following the General Procedure (isoxazole amide) 1 using 5-(4-fluoro-3-hydroxyphenyl)isoxazole-3-carboxylic acid (25 mg, 0.112 mmol) and 5-chloro-2-methylpyridin-3-amine (16 mg, 0.112 mmol). Yield: 5 mg (12%); 100% purity. $^1$H NMR (500 MHz, DMSO-$d_6$) δ 10.60 (bs, 2H), 8.44 (d, J=2.4 Hz, 1H), 8.00 (d, J=2.4 Hz, 1H), 7.51 (dd, J=8.3, 2.2 Hz, 1H), 7.46-7.39 (m, 2H), 7.35 (dd, J=11.0, 8.5 Hz, 1H), 2.45 (s, 3H); $^{13}$C NMR (126 MHz, DMSO-$d_6$) δ 170.20, 159.25, 157.68, 152.70 (d, J=246.7 Hz), 152.46, 145.89 (d, J=12.9 Hz), 144.95, 133.23, 132.21, 127.86, 122.97 (d, J=3.3 Hz), 117.67 (d, J=7.1 Hz), 117.32 (d, J=19.3 Hz), 115.03 (d, J=3.7 Hz), 99.94, 20.67; HRMS (ESI-TOF) m/z: [M−H]$^-$ Calcd for $C_{16}H_{10}ClFN_3O_3$ 346.0395, found: 346.0386.

KSC-392-157

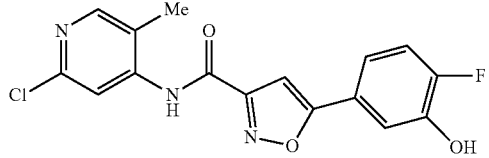

N-(2-Chloro-5-methylpyridin-4-yl)-5-(4-fluoro-3-hydroxyphenyl)isoxazole-3-carboxamide (KSC-392-157): This compound was prepared following the General Procedure (isoxazole amide) 1 using 5-(4-fluoro-3-hydroxyphenyl)isoxazole-3-carboxylic acid (25 mg, 0.112 mmol) and 2-chloro-5-methylpyridin-4-amine (16 mg, 0.112 mmol). Yield: 3 mg (6%); 91.2% purity. $^1$H NMR (500 MHz, DMSO-$d_6$) δ 10.46 (s, 1H), 10.39 (s, 1H), 8.32 (t, J=0.7 Hz, 1H), 7.82 (s, 1H), 7.52 (dd, J=8.3, 2.2 Hz, 1H), 7.49-7.42 (m, 2H), 7.37 (dd, J=11.0, 8.5 Hz, 1H), 2.28 (s, 3H); $^{13}$C NMR (126 MHz, DMSO-$d_6$) δ 170.23, 159.06, 157.59, 152.60 (d, J=246.9 Hz), 151.08, 147.99, 145.63 (d, J=12.9 Hz), 145.19, 126.01, 122.84, 117.79 (d, J=7.1 Hz), 117.67, 117.30 (d, J=19.3 Hz), 114.93 (d, J=3.7 Hz), 99.93, 14.09; HRMS (ESI-TOF) m/z: [M+H]$^+$ Calcd for $C_{16}H_{12}ClFN_3O_3$ 348.0546, found: 348.0605.

KSC-392-151

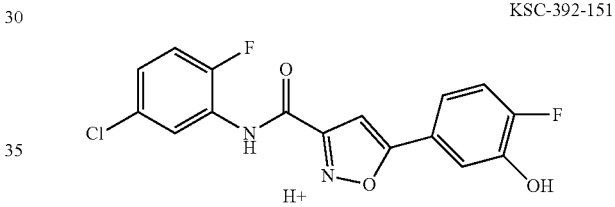

N-(5-Chloro-2-fluorophenyl)-5-(4-fluoro-3-hydroxyphenyl)isoxazole-3-carboxamide (KSC-392-151): This compound was prepared following the General Procedure (isoxazole amide) 1 using 5-(4-fluoro-3-hydroxyphenyl)isoxazole-3-carboxylic acid (25 mg, 0.112 mmol) and 5-chloro-2-fluoroaniline (16 mg, 0.112 mmol). Yield: 3 mg (7%); 94.2% purity. $^1$H NMR (500 MHz, DMSO-$d_6$) δ 10.63 (s, 2H), 7.78-7.70 (m, 1H), 7.50 (dd, J=8.3, 2.2 Hz, 1H), 7.45-7.38 (m, 4H), 7.35 (dd, J=11.0, 8.5 Hz, 1H); $^{13}$C NMR (126 MHz, DMSO-$d_6$) δ 170.17, 159.10, 157.43, 154.47 (d, J=211.3 Hz), 152.51 (d, J=209.9 Hz), 145.75 (d, J=12.8 Hz), 127.88 (d, J=3.2 Hz), 127.19 (d, J=7.8 Hz), 126.21, 125.93 (d, J=13.8 Hz), 122.96 (d, J=3.6 Hz), 117.77 (d, J=6.8 Hz), 117.69 (d, J=21.8 Hz), 117.33 (d, J=19.3 Hz), 115.00 (d, J=3.7 Hz), 99.91; HRMS (ESI-TOF) m/z: [M−H]$^-$ Calcd for $C_{16}H_8ClF_2N_2O_3$ 349.0192, found: 349.0180.

KSC-392-107

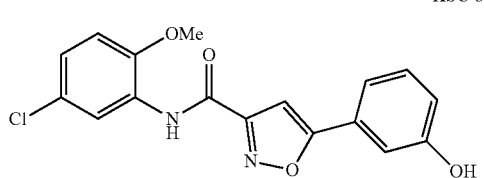

N-(5-Chloro-2-methoxyphenyl)-5-(3-hydroxyphenyl)isoxazole-3-carboxamide (KSC-392-107): This compound was prepared following the General Procedure (isoxazole amide) 1 using 5-(3-hydroxyphenyl)isoxazole-3-carboxylic acid (25 mg, 0.122 mmol) and 5-chloro-2-methoxyaniline (19 mg, 0.122 mmol). Yield: 13 mg (32%); 100% purity. $^1$H NMR (500 MHz, DMSO-$d_6$) δ 9.95 (bs, 1H), 9.58 (bs, 1H), 8.10 (d, J=2.7 Hz, 0H), 7.46 (s, 1H), 7.40 (dt, J=7.7, 1.4 Hz, 1H), 7.3-7.34 (m, 1H), 7.31 (t, J=2.0 Hz, 0H), 7.25 (dd, J=8.8, 2.6 Hz, 1H), 7.16 (d, J=8.8 Hz, 1H), 6.95 (ddd, J=7.8, 2.5, 1.2 Hz, 1H), 3.90 (s, 3H); $^{13}$C NMR (126 MHz, DMSO-$d_6$) δ 171.26, 159.13, 157.97, 156.62, 148.62, 130.53, 127.15, 127.03, 124.96, 123.92, 121.03, 118.10, 116.70, 112.79, 112.17, 99.79, 56.35; HRMS (ESI-TOF) m/z: [M+H]$^+$ Calcd for $C_{17}H_{14}ClN_2O_4$ 345.0637, found: 345.0608.

KSC-392-109

N-(5-Chloro-2-(dimethylamino)phenyl)-5-(3-hydroxyphenyl)isoxazole-3-carboxamide (KSC-392-109): This compound was prepared following the General Procedure (isoxazole amide) 1 using 5-(3-hydroxyphenyl)isoxazole-3-carboxylic acid (25 mg, 0.122 mmol) and 4-chloro-N1,N1-dimethylbenzene-1,2-diamine (22 mg, 0.122 mmol). Yield: 13 mg (29%); 98.2% purity. $^1$H NMR (500 MHz, DMSO-$d_6$) δ 9.94 (bs, 1H), 9.83 (s, 1H), 8.26 (d, J=2.5 Hz, 1H), 7.49 (s, 1H), 7.42 (dt, J=7.7, 1.3 Hz, 1H), 7.38-7.36 (m, 1H), 7.35-7.32 (m, 2H), 7.22 (dd, J=8.5, 2.5 Hz, 1H), 6.95 (ddd, J=8.0, 2.5, 1.1 Hz, 1H), 2.67 (s, 6H); $^{13}$C NMR (126 MHz, DMSO-$d_6$) δ 171.50, 159.30, 157.93, 156.31, 142.82, 132.68, 130.53, 127.94, 127.14, 124.47, 122.05, 119.45, 118.12, 116.77, 112.18, 99.77, 44.08; HRMS (ESI-TOF) m/z: [M+H]$^+$ Calcd for $C_{18}H_{17}ClN_3O_3$ 358.0953, found: 358.0930.

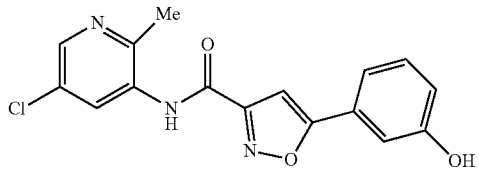

KSC-392-125

N-(5-Chloro-2-methylpyridin-3-yl)-5-(3-hydroxyphenyl)isoxazole-3-carboxamide (KSC-392-125): This compound was prepared following the General Procedure (isoxazole amide) 1 using 5-(3-hydroxyphenyl)isoxazole-3-carboxylic acid (28 mg, 0.136 mmol) and 5-chloro-2-methylpyridin-3-amine (19 mg, 0.136 mmol). Yield: 16 mg (34%); 100% purity. NMR (500 MHz, DMSO-$d_6$) δ 10.61 (s, 1H), 9.92 (s, 1H), 8.44 (d, J=2.3 Hz, 1H), 8.00 (d, J=2.4 Hz, 1H), 7.44 (s, 1H), 7.41 (dt, J=7.7, 1.4 Hz, 1H), 7.37 (t, J=7.8 Hz, 1H), 7.32 (dd, J=2.4, 1.6 Hz, 1H), 6.95 (ddd, J=7.8, 2.5, 1.2 Hz, 1H), 2.46 (s, 3H); $^{13}$C NMR (126 MHz, DMSO-$d_6$) δ 170.95, 159.17, 157.99, 157.70, 152.44, 144.94, 133.21, 132.19, 130.63, 127.84, 127.27, 118.10, 116.80, 112.21, 100.11, 20.67; HRMS (ESI-TOF) m/z: [M+H]$^+$ Calcd for $C_{18}H_{17}ClN_3O_3$ 330.0640, found: 330.0595.

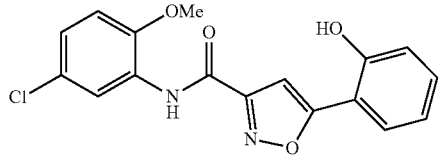

KSC-392-108

N-(5-Chloro-2-(dimethylamino)phenyl)-5-(3-hydroxyphenyl)isoxazole-3-carboxamide (KSC-392-108): This compound was prepared following the General Procedure (isoxazole amide) 1 using 5-(2-hydroxyphenyl)isoxazole-3-carboxylic acid (25 mg, 0.122 mmol) and 5-chloro-2-methoxyaniline (19 mg, 0.122 mmol). Yield: 3 mg (7%); 97.8% purity. $^1$H NMR (500 MHz, DMSO-$d_6$) δ 10.87 (bs, 1H), 9.61 (s, 1H), 8.10 (d, J=2.7 Hz, 1H), 7.84 (dd, J=7.9, 1.7 Hz, 1H), 7.38 (ddd, J=8.6, 7.3, 1.7 Hz, 1H), 7.26 (dd, J=8.8, 2.6 Hz, 1H), 7.24 (s, 1H), 7.19-7.15 (m, 1H), 7.08 (dd, J=8.3, 1.1 Hz, 1H), 6.99 (dd, J=8.1, 0.8 Hz, 1H), 3.90 (s, 3H); $^{13}$C NMR (126 MHz, DMSO-$d_6$) δ 168.19, 158.97, 156.89, 155.17, 148.78, 132.22, 127.11, 126.79, 125.04, 123.96, 121.25, 119.53, 116.66, 113.05, 112.88, 101.98, 56.41; HRMS (ESI-TOF) m/z: [M+H]$^+$ Calcd for $C_{17}H_{14}ClN_2O_4$ 345.0637, found: 345.0596.

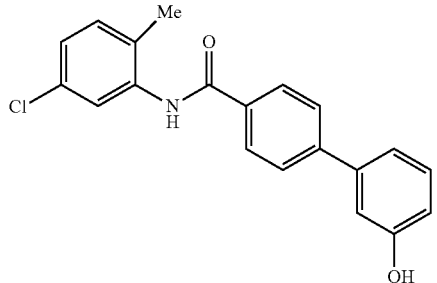

KSC-392-125

N-(5-Chloro-2-methylphenyl)-3'-hydroxy-[1,1'-biphenyl]-4-carboxamide (KSC-392-125): This compound was prepared following the General Procedure (isoxazole amide) 1 using 3'-hydroxy-[1,1'-biphenyl]-4-carboxylic acid (30 mg, 0.140 mmol) and 5-chloro-2-methylaniline (20 mg, 0.140 mmol). Yield: 10 mg (20%); 95% purity. $^1$H NMR (500 MHz, DMSO-$d_6$) δ 9.98 (s, 1H), 9.65 (bs, 1H), 8.05 (d, J=8.5 Hz, 2H), 7.77 (d, J=8.5 Hz, 2H), 7.51 (d, J=2.3 Hz, 1H), 7.34-7.26 (m, 2H), 7.24 (dd, J=8.2, 2.3 Hz, 1H), 7.16 (ddd, J=7.7, 1.8, 0.9 Hz, 1H), 7.10 (t, J=2.1 Hz, 1H), 6.83 (ddd, J=8.1, 2.5, 0.9 Hz, 1H), 2.25 (s, 3H); $^{13}$C NMR (126 MHz, DMSO-$d_6$) δ 165.11, 157.94, 143.48, 140.55, 137.83, 132.96, 132.35, 131.84, 130.12, 129.81, 128.40, 126.59, 125.83, 125.58, 117.68, 115.17, 113.68, 17.44; HRMS (ESI-TOF) m/z: [M−H]$^−$ Calcd for $C_{20}H_{15}ClNO_2$ 336.0791, found: 336.0782.

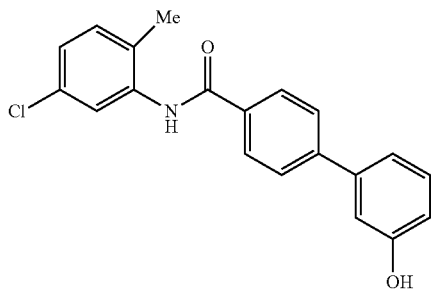

KSC-392-125

N-(5-Chloro-2-methylphenyl)-3'-hydroxy-[1,1'-biphenyl]-4-carboxamide (KSC-392-125): This compound was prepared following the General Procedure (isoxazole amide) 1 using 3'-hydroxy-[1,1'-biphenyl]-4-carboxylic acid (30 mg, 0.140 mmol) and 5-chloro-2-methylaniline (20 mg, 0.140 mmol). Yield: 10 mg (20%); 95% purity. $^1$H NMR (500 MHz, DMSO-$d_6$) δ 9.98 (s, 1H), 9.65 (bs, 1H), 8.05 (d, J=8.5 Hz, 2H), 7.77 (d, J=8.5 Hz, 2H), 7.51 (d, J=2.3 Hz, 1H), 7.34-7.26 (m, 2H), 7.24 (dd, J=8.2, 2.3 Hz, 1H), 7.16 (ddd, J=7.7, 1.8, 0.9 Hz, 1H), 7.10 (t, J=2.1 Hz, 1H), 6.83 (ddd, J=8.1, 2.5, 0.9 Hz, 1H), 2.25 (s, 3H); $^{13}$C NMR (126 MHz, DMSO-$d_6$) δ 165.11, 157.94, 143.48, 140.55, 137.83, 132.96, 132.35, 131.84, 130.12, 129.81, 128.40, 126.59, 125.83, 125.58, 117.68, 115.17, 113.68, 17.44; HRMS (ESI-TOF) m/z: [M−H]$^-$ Calcd for $C_{20}H_{15}ClNO_2$ 336.0791, found: 336.0782.

KSC-392-162

N-(3-Chlorophenyl)-5-(3-(methylsulfonamido)phenyl)isoxazole-3-carboxamide (KSC-392-162): This compound was prepared following the General Procedure (isoxazole amide) 1 using 5-(3-(methylsulfonamido)phenyl)isoxazole-3-carboxylic acid (25 mg, 0.089 mmol) and 3-chloroaniline (11 mg, 0.089 mmol). Yield: 8 mg (23%); 100% purity. $^1$H NMR (500 MHz, DMSO-$d_6$) δ 10.97 (s, 1H), 10.06 (s, 1H), 7.97 (t, J=2.1 Hz, 1H), 7.79-7.69 (m, 3H), 7.55 (t, J=7.9 Hz, 1H), 7.49 (s, 1H), 7.42 (t, J=8.1 Hz, 1H), 7.38 (ddd, J=8.1, 2.2, 1.0 Hz, 1H), 7.23 (ddd, J=8.0, 2.1, 0.9 Hz, 1H), 3.08 (s, 3H); $^{13}$C NMR (126 MHz, DMSO-$d_6$) δ 170.24, 159.74, 157.39, 139.49, 139.40, 133.06, 130.55, 127.14, 124.26, 121.86, 121.52, 120.06, 119.04, 116.11, 100.65; HRMS (ESI-TOF) m/z: [M+H]$^+$ Calcd for $C_{17}H_{15}ClN_3O_4S$ 392.0466, found: 392.0470.

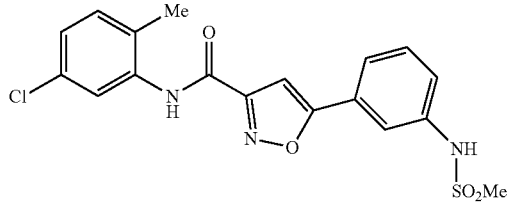

KSC-392-163

N-(5-Chloro-2-methylphenyl)-5-(3-(methylsulfonamido)phenyl)isoxazole-3-carboxamide (KSC-392-163): This compound was prepared following the General Procedure (isoxazole amide) 1 using 5-(3-(methylsulfonamido)phenyl)isoxazole-3-carboxylic acid (25 mg, 0.089 mmol) and 5-chloro-2-methylaniline (113 mg, 0.089 mmol). Yield: 6 mg (16%); 98.9% purity. $^1$H NMR (500 MHz, DMSO-$d_6$) δ 10.40 (s, 1H), 10.06 (s, 1H), 7.76-7.67 (m, 4H), 7.54 (t, J=7.9 Hz, 1H), 7.51 (d, J=2.3 Hz, 1H), 7.48 (s, 1H), 7.37 (ddd, J=8.1, 2.2, 1.0 Hz, 1H), 7.36-7.30 (m, 1H), 7.27 (dd, J=8.2, 2.2 Hz, 1H), 3.08 (s, 3H), 2.24 (s, 3H); $^{13}$C NMR (126 MHz, DMSO-$d_6$) δ 170.24, 159.50, 157.33, 139.41, 136.51, 132.46, 132.01, 130.59, 129.94, 127.19, 126.27, 125.82, 121.79, 121.50, 116.06, 100.63, 17.32; HRMS (ESI-TOF) m/z: [M+H]$^+$ Calcd for $C_{18}H_{17}ClN_3O_4S$ 406.0623, found: 406.063.

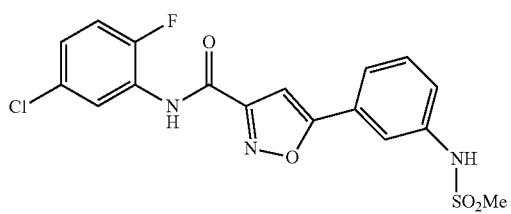

KSC-392-164

N-(5-Chloro-2-fluorophenyl)-5-(3-(methylsulfonamido)phenyl)isoxazole-3-carboxamide (KSC-392-164): This compound was prepared following the General Procedure (isoxazole amide) 1 using 5-(3-(methylsulfonamido)phenyl)isoxazole-3-carboxylic acid (25 mg, 0.089 mmol) and 5-chloro-2-fluoroaniline (13 mg, 0.089 mmol). Yield: 3 mg (7%); 97% purity. $^1$H NMR (500 MHz, DMSO-$d_6$) δ 10.68 (s, 1H), 10.06 (s, 1H), 7.78-7.66 (m, 3H), 7.54 (t, J=7.9 Hz, 1H), 7.51 (s, 1H), 7.44-7.34 (m, 3H), 3.08 (s, 3H); $^{13}$C NMR (126 MHz, DMSO-$d_6$) 170.37, 159.12, 157.38, 154.37 (d, J=248.2 Hz), 139.41, 130.60, 127.90 (d, J=3.2 Hz), 127.26 (d, J=7.9 Hz), 127.12, 125.90 (d, J=13.7 Hz), 121.85, 121.53, 117.71 (d, J=21.8 Hz), 116.06, 100.61, 40.43; HRMS (ESI-TOF) m/z: [M+H]$^+$ Calcd for $C_{17}H_{14}ClFN_3O_4S$ 410.0372, found: 410.0374.

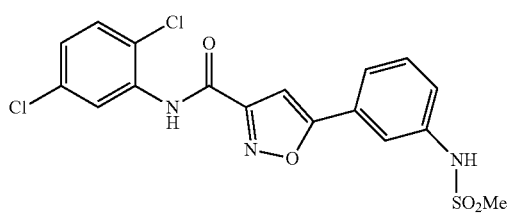

KSC-392-165

N-(2,5-Dichlorophenyl)-5-(3-(methylsulfonamido)phenyl)isoxazole-3-carboxamide (KSC-392-165): This compound was prepared following the General Procedure (isoxazole amide) 1 using 5-(3-(methylsulfonamido)phenyl)isoxazole-3-carboxylic acid (25 mg, 0.089 mmol) and 2,5-dichloroaniline (14 mg, 0.089 mmol). Yield: 8 mg (21%); 95.7% purity. $^1$H NMR (500 MHz, DMSO-$d_6$) δ 10.47 (s, 1H), 10.07 (s, 1H), 7.84 (d, J=2.6 Hz, 1H), 7.77-7.69 (m, 4H), 7.64 (d, J=8.6 Hz, 1H), 7.58-7.51 (m, 1H), 7.52 (s, 1H), 7.42 (dd, J=8.7, 2.5 Hz, 1H), 7.38 (ddd, J=8.2, 2.2, 1.0 Hz, 1H), 3.09 (s, 3H); $^{13}$C NMR (126 MHz, DMSO-$d_6$) δ 170.54, 159.10, 157.27, 139.41, 135.13, 131.69, 131.09, 130.60, 127.63, 127.43, 127.10, 126.88, 121.86, 121.54, 116.06, 100.58, 40.43; HRMS (ESI-TOF) m/z: [M+H]$^+$ Calcd for $C_{17}H_{14}Cl_2N_3O_4S$ 426.0077, found: 426.0087.

KSC-392-166

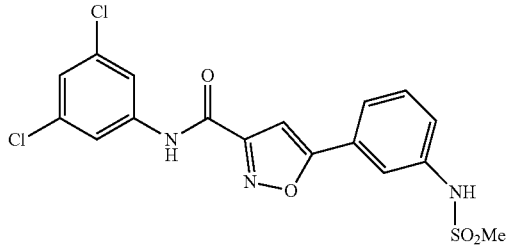

N-(3,5-Dichlorophenyl)-5-(3-(methylsulfonamido)phenyl)isoxazole-3-carboxamide (KSC-392-166): This compound was prepared following the General Procedure (isoxazole amide) 1 using 5-(3-(methylsulfonamido)phenyl)isoxazole-3-carboxylic acid (25 mg, 0.089 mmol) and 3,5-dichloroaniline (14 mg, 0.089 mmol). Yield: 6 mg (15%); 92.9% purity. $^1$H NMR (500 MHz, DMSO-$d_6$) δ 11.13 (s, 1H), 10.06 (s, 1H), 7.93 (d, J=1.9 Hz, 2H), 7.77-7.70 (m, 2H), 7.55 (t, J=7.9 Hz, 1H), 7.50 (s, 1H), 7.41 (t, J=1.9 Hz, 1H), 7.38 (ddd, J=8.1, 2.2, 1.0 Hz, 1H), 3.08 (s, 3H); $^{13}$C NMR (126 MHz, DMSO-$d_6$) δ 170.40, 159.50, 157.60, 140.39, 139.40, 134.11, 130.60, 127.06, 123.79, 121.91, 121.56, 118.75, 116.12, 100.68, 40.43; HRMS (ESI-TOF) m/z: [M+H]$^+$ Calcd for $C_{17}H_{14}Cl_2N_3O_4S$ 426.0077, found: 426.0051.

KSC-392-167

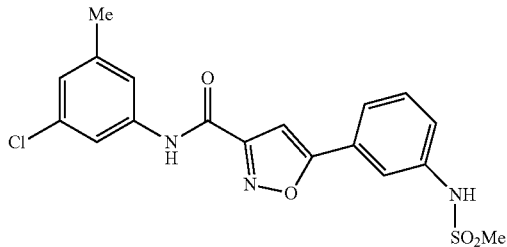

N-(3-Chloro-5-methylphenyl)-5-(3-(methylsulfonamido)phenyl)isoxazole-3-carboxamide (KSC-392-167): This compound was prepared following the General Procedure (isoxazole amide) 1 using 5-(3-(methylsulfonamido)phenyl)isoxazole-3-carboxylic acid (25 mg, 0.089 mmol) and 3-chloro-5-methylaniline (13 mg, 0.089 mmol). Yield: 8 mg (22%); 98.3% purity. $^1$H NMR (500 MHz, DMSO-$d_6$) δ 10.87 (s, 1H), 10.06 (s, 1H), 7.78-7.68 (m, 3H), 7.59 (d, J=1.3 Hz, 1H), 7.54 (t, J=7.9 Hz, 1H), 7.47 (s, 1H), 7.37 (ddd, J=8.1, 2.2, 1.0 Hz, 1H), 3.08 (s, 3H), 2.32 (s, 3H); $^{13}$C NMR (126 MHz, DMSO-$d_6$) δ 170.20, 159.75, 157.34, 140.39, 139.40, 139.22, 132.78, 130.59, 127.14, 124.79, 121.85, 121.51, 119.57, 117.30, 116.10, 100.60, 40.43, 20.99; HRMS (ESI-TOF) m/z: [M+H]$^+$ Calcd for $C_{18}H_{17}ClN_3O_4S$ 406.0623, found: 406.0633.

KSC-392-170

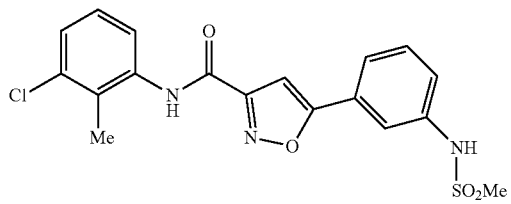

N-(3-Chloro-2-methylphenyl)-5-(3-(methylsulfonamido)phenyl)isoxazole-3-carboxamide (KSC-392-170): This compound was prepared following the General Procedure (isoxazole amide) 1 using 5-(3-(methylsulfonamido)phenyl)isoxazole-3-carboxylic acid (25 mg, 0.089 mmol) and 3-chloro-2-methylaniline (13 mg, 0.089 mmol). Yield: 8 mg (22%); 98.3% purity. $^1$H NMR (500 MHz, DMSO-$d_6$) δ 10.60 (s, 1H), 10.07 (s, 1H), 7.74 (t, J=1.8 Hz, 1H), 7.71 (dt, J=7.8, 1.3 Hz, 1H), 7.54 (t, J=7.9 Hz, 1H), 7.48 (s, 1H), 7.41 (dd, J=8.0, 1.1 Hz, 1H), 7.40-7.33 (m, 2H), 7.28 (t, J=7.9 Hz, 1H), 3.08 (s, 3H), 2.26 (s, 3H); $^{13}$C NMR (126 MHz, DMSO-$d_6$) δ 170.24, 159.51, 157.47, 139.53, 136.74, 133.89, 132.23, 127.38, 127.20, 127.10, 125.95, 121.79, 121.40, 116.05, 100.62, 40.43, 15.33; HRMS (ESI-TOF) m/z: [M+H]$^+$ Calcd for $C_{18}H_{17}ClN_3O_4S$ 406.0623, found: 406.0628.

KSC-392-168

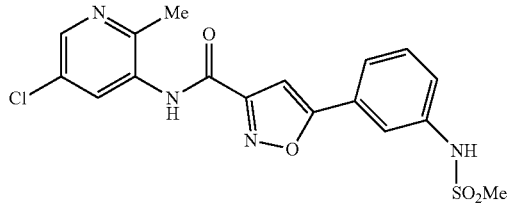

N-(5-Chloro-2-methylpyridin-3-yl)-5-(3-(methylsulfonamido)phenyl)isoxazole-3-carboxamide (KSC-392-168): This compound was prepared following the General Procedure (isoxazole amide) 1 using 5-(3-(methylsulfonamido)phenyl)isoxazole-3-carboxylic acid (25 mg, 0.089 mmol) and 5-chloro-2-methylpyridin-3-amine (13 mg, 0.089 mmol). Yield: 2 mg (6%); 100% purity. $^1$H NMR (500 MHz, DMSO-$d_6$) δ 10.65 (s, 1H), 10.06 (s, 1H), 8.45 (d, J=2.3 Hz, 1H), 8.00 (d, J=2.3 Hz, 1H), 7.78-7.65 (m, 2H), 7.55 (t, J=7.9 Hz, 1H), 7.51 (s, 1H), 7.38 (ddd, J=8.1, 2.2, 1.0 Hz, 1H), 3.09 (s, 3H), 2.46 (s, 3H); $^{13}$C NMR (126 MHz, DMSO-$d_6$) δ 170.38, 159.27, 157.60, 152.53, 145.02, 139.41, 133.33, 132.16, 130.60, 127.86, 127.13, 121.85, 121.53, 116.07, 100.66, 40.43, 20.68; FIRMS (ESI-TOF) m/z: [M+H]$^+$ Calcd for $C_{17}H_{16}ClN_4O_4S$ 407.0575, found: 407.0596.

Synthesis of Representative Benzamide Intermediates

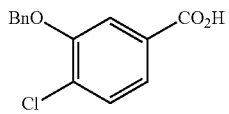

KSC-392-022

3-(Benzyloxy)-4-chlorobenzoic acid (KSC-392-022): Benzyl bromide (0.793 ml, 6.66 mmol) was added drop wise to a solution of 4-chloro-3-hydroxybenzoic acid (0.5 g, 2.90 mmol) in DMF (2.9 ml) and potassium carbonate (0.881 g, 6.37 mmol). The reaction mixture was stirred overnight at room temperature. Upon completion, the reaction mixture was mixed with water and extracted with ethyl acetate. The combined organic layers were dried with anhydrous sodium sulfate, filtered, and evaporated to dryness. This residue was dissolved in MeOH (1.5 ml 10 M KOH (0.867 ml, 8.67 mmol) was added. The reaction mixture was stirred for 4 h at 50° C. The reddish solution was diluted with water and acidified with 3 N aqueous hydrochloric acid. The precipitate formed was extracted with ethyl acetate, washed with water, dried with anhydrous sodium sulfate, filtered, and evaporated to dryness. The resulting residue was purified according to the preparative RP HPLC methods described in the General Experimental section. Isolated 3-(benzyloxy)-4-chlorobenzoic acid (0.454 g, 1.728 mmol, 59.6% yield) as a white solid. $^1$H NMR (400 MHz, DMSO-$d_6$) δ 7.68 (d, J=1.7 Hz, 1H), 7.60-7.51 (m, 2H), 7.50-7.45 (m, 2H), 7.44-7.38 (m, 2H), 7.37-7.32 (m, 1H), 5.27 (s, 2H); HRMS (ESI-TOF) m/z: [M+H]$^+$ Calcd for $C_{14}H_{10}ClO_3$ 261.0318; Found 261.0348.

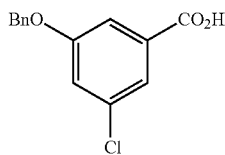

KSC-392-023

3-(Benzyloxy)-5-chlorobenzoic acid (KSC-392-023): This compound was prepared following the procedure KSC-392-022 using 3-chloro-5-hydroxybenzoic acid (100 mg, 0.579 mmol). Yield: 89 mg (59%), 94.7% purity. $^1$H NMR (400 MHz, DMSO-$d_6$) δ 7.49-7.47 (m, 1H), 7.47-7.43 (m, 3H), 7.42-7.32 (m, 4H), 5.19 (s, 2H); HRMS (ESI-TOF) m/z: [M−H]$^−$ Calcd for $C_{14}H_{10}ClO_3$ 261.0318; Found 261.0237.

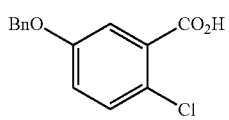

KSC-392-024

5-(Benzyloxy)-2-chlorobenzoic acid (KSC-392-024): This compound was prepared following the procedure KSC-392-022 using 2-chloro-5-hydroxybenzoic acid (500 mg, 2.90 mmol). Yield: 131 mg (17%), 100% purity. $^1$H NMR (400 MHz, DMSO-$d_6$) δ 13.44 (s, 1H), 7.48-7.30 (m, 7H), 7.17 (dd, J=8.8, 3.1 Hz, 1H), 5.15 (s, 2H); HRMS (ESI-TOF) m/z: [M+H]$^+$ Calcd for $C_{14}H_{12}ClO3$ 263.0469; Found 263.0430.

General Procedure (Benzamides) 1

To a solution of the appropriate aniline (0.268 mmol, 1 eq.) in DMF (0.32 M, 0.840 mL) was added PyBOP (0.536 mmol, 2 eq.), Hunig's base (0.429 mmol, 1.6 eq.), and the appropriate benzoic acid (0.268 mmol, 1 eq.). The reaction mixture was subjected to microwave radiation at 120° C. for 15 min following which the resulting residue was purified according to the preparative RP HPLC methods described herein.

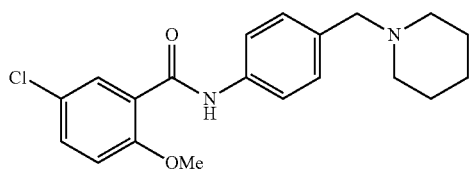

KSC-338-032

5-Chloro-2-methoxy-N-(4-(piperidin-1-ylmethyl)phenyl)benzamide (KSC-338-032): This compound was prepared following the General Procedure (benzamides) 1 using 4-(piperidin-1-ylmethyl)aniline (51 mg, 0.268 mmol) and 5-chloro-2-methoxybenzoic acid (50 mg, 0.268 mmol). Yield: 67 mg (69%). $^1$H NMR (400 MHz, DMSO-$d_6$) δ 10.15 (s, 1H), 7.70-7.60 (m, 2H), 7.59 (d, J=2.8 Hz, 1H), 7.54 (dd, J=8.8, 2.8 Hz, 1H), 7.27-7.20 (m, 2H), 7.20 (d, J=8.9 Hz, 1H), 3.88 (s, 3H), 3.37 (s, 2H), 2.39-2.16 (m, 4H), 1.48 (p, J=5.5 Hz, 4H), 1.42-1.30 (m, 2H); HRMS (ESI-TOF) m/z: [M+H]$^+$ Calcd for $C_{20}H_{24}ClN_2O_2$ 359.1521; Found 359.1517.

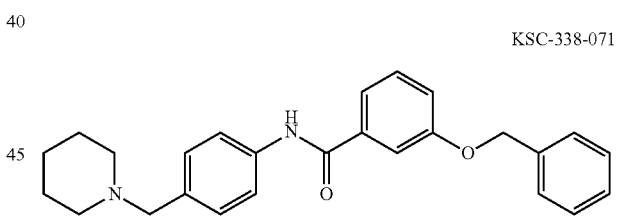

KSC-338-071

3-(Benzyloxy)-N-(4-(piperidin-1-ylmethyl)phenyl)benzamide (KSC-338-071): $^1$H NMR (400 MHz, DMSO-$d_6$) δ 10.18 (s, 1H), 7.74-7.65 (m, 2H), 7.61-7.55 (m, 1H), 7.58-7.50 (m, 1H), 7.52-7.36 (m, 5H), 7.29-7.19 (m, 3H), 5.19 (s, 2H), 3.38 (s, 2H), 2.35-2.15 (bm, 4H), 1.48 (p, J=5.4 Hz, 4H), 1.42-1.32 (m, 2H); HRMS (ESI-TOF) m/z: [M+H]$^+$ Calcd for $C_{26}H_{29}N_2O_2$ 401.2224; Found 401.2219.

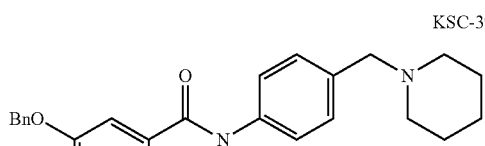

KSC-392-029

3-(Benzyloxy)-4-chloro-N-(4-(piperidin-1-ylmethyl)phenyl)benzamide (KSC-392-029): This compound was prepared following the General Procedure (benzamides) 1 using 4-(piperidin-1-ylmethyl)aniline (36 mg, 0.190 mmol) and 3-(benzyloxy)-4-chlorobenzoic acid (50 mg, 0.190 mmol). Yield: 49 mg (59%); 100% purity. $^1$H NMR (400 MHz, DMSO-$d_6$) δ 10.26 (s, 1H), 7.75 (d, J=1.8 Hz, 1H), 7.70-7.62 (m, 2H), 7.64-7.53 (m, 2H), 7.53-7.45 (m, 2H), 7.47-7.38 (m, 2H), 7.40-7.30 (m, 1H), 7.29-7.21 (m, 2H), 5.30 (s, 2H), 3.40-3.34 (m, 2H), 2.38-2.18 (bm, 4H), 1.48 (p, J=5.5 Hz, 4H), 1.41-1.28 (m, 2H); HRMS (ESI-TOF) m/z: [M++H]$^+$ Calcd for $C_{26}H_{28}ClN_2O_2$ 435.1834; Found 435.1815.

Detailed Assay Protocols

μHTS Identification of Small Molecule Inhibitors of the Mitochondrial Permeability Transition Pore Via an Absorbance Assay (Primary Screening Assay, Single Concentration, AID No. 602449)

List of Reagents:

Assay Buffer: 250 mM sucrose, 10 mM MOPS-Tris, 0.01 mM EGTA-Tris, 1.0 mM phosphoric acid, pH 7.4
  Solution 1: 0.5 mg/mL mitochondria in Assay Buffer
  Solution 2: 2.0 mM EGTA-Tris, pH 7.4 in Solution 3
  Solution 3: 80-200 μM $CaCl_2$ depending on mitochondrial activity, 5.0 mM glutamate, 2.5 mM malate in Assay Buffer. Note: Concentration of calcium in the assay is dependent upon the activity of the isolated mitochondria which is determined via a calcium titration just before each high-throughput screening batch. A calcium concentration is used that allows for the arrival at a 2:1 window at the 30 minute time period.

Protocol Summary:

1. Compounds are pre-spotted into assay plates the morning of or the night before the assay. Via the LabCyte Echo, 16 nL of 5 mM compound is transferred to Greiner, 1536-well, clear assay plates (Greiner 782101) to achieve 10 μM in 8 μL assay final volume. To the control wells in Columns 1-4, 16 nL of DMSO is transferred.

2. Prepare positive and negative control solutions, the mitochondrial suspension and the calcium solution working stocks according to the recipes in the Reagent Section.

3. Upon determination of activity, freshly isolated mitochondria from mice are suspended in assay buffer (Solution 1) and 4 μL of this solution is added to all wells of the assay plate with a MultiDrop Combi. Final assay concentration of mitochondria will be about 0.25 mg/mL (Working Stock ~0.5 mg/mL).

4. Following the addition of the mitochondrial suspension, 4 μL of the positive control working stock containing 2.0 mM EGTA-Tris, pH 7.4 in assay buffer (Solution 2) is added to Columns 1-2. Final assay concentration=1.0 mM EGTA-Tris, pH 7.4.

5. Next, 4 μL of Calcium solution (Solution 3) is added to negative control and test compound wells, Columns 3-48. Final concentration of calcium will be 40-100 μM (80-200 μM in the working stock).

6. Assay plate is immediately spun at 1000 rpm for ~60 seconds.

7. Plate is kept at room temperature for 30 minutes and then read on the BMG Pherastar utilizing absorbance at 540 nm.

Comments:

Compounds that demonstrated a corrected % activity >=50% compared to the controls are defined as active in the assay.

The experimental values were normalized by the difference between values from neutral and stimulator control wells in each plate. Then normalized data was corrected to remove systematic plate patterns due to artifacts such as dispensing tip issues etc. Further information about data correction is available at http://www.genedata.com/products/screener.html.

To simplify the distinction between the inactives of the primary screen and of the confirmatory screening stage, the Tiered Activity Scoring System was developed and implemented.

Activity Scoring:

Activity scoring rules were devised to take into consideration compound efficacy, its potential interference with the assay and the screening stage that the data was obtained. Details of the Scoring System will be published elsewhere. Briefly, the outline of the scoring system utilized for the assay is as follows:

1) First tier (0-40 range) is reserved for primary screening data. The score is correlated with % activity in the assay:
  a. If outcome of the primary screen is inactive, then the assigned score is 0
  b. If outcome of the primary screen is inconclusive, then the assigned score is 10
  c. If outcome of the primary screen is active, then the assigned score is 20
  Scoring for Single concentration confirmation screening is not applicable to this assay.
  d. If outcome of the single-concentration confirmation screen is inactive, then the assigned score is 21
  e. If outcome of the single-concentration confirmation screen is inconclusive, then the assigned score is 25
  f. If outcome of the single-concentration confirmation screen is active, then the assigned score is 30

This scoring system helps track the stage of the testing of a particular SID. For the primary hits which are available for confirmation, their scores will be greater than 20. For those which are not further confirmed, their score will stay under 21.

2) Second tier (41-80 range) is reserved for dose-response confirmation data and is not applicable in this assay 3) Third tier (81-100 range) is reserved for resynthesized true positives and their analogues and is not applicable in this assay Single Concentration Confirmation of μHTS Inhibitor Hits of the Mitochondrial Permeability Transition Pore Via a Fluorescent Based Assay (Counterscreen Assay, Single Concentration, AID No. 624504)

List of Reagents:

Assay Buffer: 250 mM sucrose, 10 mM MOPS-Tris, 0.01 mM EGTA-Tris, 1.0 mM phosphoric acid-Tris, pH 7.4.
  Solution 1: 0.5 mg/mL mitochondria in Assay Buffer.
  Solution 2: 0.8 μM Rh123, 5.0 mM glutamate and 2.5 mM malate in Assay Buffer.

Protocol Summary:

1. Compounds are pre-spotted into assay plates the morning of or the night before the assay. Via a LabCyte Echo, 40 nL of 5 mM compound is transferred to a Greiner, 384-well, black assay plates (Greiner 781076) to achieve 10 μM in 20 μl final assay volume. To the positive control wells, 40 nL of 0.2 mM carbonyl cyanide 4-(trifluoromethoxy)phenylhydrazone (FCCP) is transferred. To the negative control wells, 40 nL of DMSO is transferred.

2. Prepare Assay Buffer, Rhodamine 123 (Rh123) Solution and the mitochondrial suspension working stocks according to the recipes in the Reagent Section.

3. Freshly isolated mitochondria from mice are suspended in Assay Buffer (Solution 1) and 10 µL of this solution is added to all wells of the assay plate with a MultiDrop Combi. Final assay concentration of mitochondria will be about 0.25 mg/mL (Working Stock ~0.5 mg/mL), depending on relative activity of mitochondrial preparation.

4. Following the addition of the mitochondrial suspension, 10 µL of Rh123 Solution (Solution 2) is added to each well of the assay plate.

5. Assay plate is immediately spun at 1000 rpm for ~60 seconds.

6. Plate is kept at room temperature for 5 minutes and then read on the BMG Pherastar utilizing a fluorescence intensity optical module that allows for excitation at 480 nm and a read at an emission wavelength of 520 nm.

Comments:

Compounds that demonstrated a % activity_mean >=20% compared to the controls are defined as active in the assay.

To simplify the distinction between the inactives of the primary screen and of the confirmatory screening stage, the Tiered Activity Scoring System was developed and implemented.

Activity Scoring:

Activity scoring rules were devised to take into consideration compound efficacy, its potential interference with the assay and the screening stage that the data was obtained. Details of the Scoring System will be published elsewhere. Briefly, the outline of the scoring system utilized for the assay is as follows:

1) First tier (0-40 range) is reserved for primary screening data. The score is correlated with % activity in the assay. Scoring for the primary screening is not applicable to this assay.
   a. If outcome of the primary screen is inactive, then the assigned score is 0
   b. If outcome of the primary screen is inconclusive, then the assigned score is 10
   c. If outcome of the primary screen is active, then the assigned score is 20
   Scoring for Single concentration confirmation screening is applicable to this assay.
   d. If outcome of the single-concentration confirmation screen is inactive, then the assigned score is 21
   e. If outcome of the single-concentration confirmation screen is inconclusive, then the assigned score is 25
   f. If outcome of the single-concentration confirmation screen is active, then the assigned score is 30
   This scoring system helps track the stage of the testing of a particular SID. For the primary hits which are available for confirmation, their scores will be greater than 20. For those which are not further confirmed, their score will stay under 21.
2) Second tier (41-80 range) is reserved for dose-response confirmation data and is not applicable in this assay.
3) Third tier (81-100 range) is reserved for resynthesized true positives and their analogues and is not applicable in this assay.

Dose Response Confirmation of µHTS Inhibitor Hits of the Mitochondrial Permeability Transition Pore Via an Absorbance Assay (Confirmatory Assay, Concentration-Response, AID No. 651561)

List of Reagents:
Assay Buffer: 250 mM sucrose, 10 mM MOPS-Tris, 0.01 mM EGTA-Tris, 1.0 mM phosphoric acid-Tris, pH 7.4
Solution 1: 0.5 mg/mL mitochondria in Assay Buffer
Solution 2: 2.0 mM EGTA-Tris, pH 7.4 in Solution 3
Solution 3: 80-200 µM $CaCl_2$) depending on mitochondrial activity, 5.0 mM glutamate, 2.5 mM malate in Assay Buffer. Note: Concentration of calcium in the assay is dependent upon the activity of the isolated mitochondria which is determined via a calcium titration just before each high-throughput screening batch. A calcium concentration is used that allows for the arrival at a 2:1 window at the 30 minute time period.

Protocol Summary:

1. Compounds are pre-spotted into assay plates the morning of or the night before the assay. Via the LabCyte Echo, varying volumes of 10 mM test compounds in DMSO are transferred to a Greiner, 1536-well, clear assay plates (Greiner 782101) to achieve appropriate test volume concentrations and range. Varying volumes of DMSO are transferred to the wells of the assay plate to equilibrate ifs concentration between wells for a total volume of 64 nL of DMSO per well or 0.8% final assay concentration. Positive and negative control wells will also contain 64 nL of DMSO.

2. Prepare positive and negative control solutions, the mitochondrial suspension and the calcium solution working stocks according to the recipes in the Reagent Section.

3. Freshly isolated mitochondria from mice are suspended in assay buffer (Solution 1) and 4 µL of this solution is added to all wells of the assay plate with a MultiDrop Combi. Final assay concentration of mitochondria will be about 0.25 mg/mL (Working Stock ~0.5 mg/mL) depending on the relative activity of each batch of mitochondrial preparation.

4. Following the addition of the mitochondrial suspension, 4 µL of the positive control working stock containing 2.0 mM EGTA-Tris, pH 7.4 in assay buffer (Solution 2) is added to Columns 1-2. Final assay concentration=1.0 mM EGTA-Tris, pH 7.4.

5. Next, 4 µL of Calcium solution (Solution 3) is added to negative control and test compound wells, Columns 3-48. Final concentration of calcium will be 40-100 µM (80-200 µM in the working stock) depending on mitochondrial activity.

6. Assay plate is immediately spun at 1000 rpm for ~60 seconds.

7. Plate is kept at room temperature for 30 minutes and then read on the BMG Pherastar utilizing absorbance at 540 nm.

Comments:

Compounds that demonstrated an $EC_{50}$ of 20 µM or less are defined as active in this assay.

To simplify the distinction between the inactives of the primary screen and of the confirmatory screening stage, the Tiered Activity Scoring System was developed and implemented.

Activity Scoring:

Activity scoring rules were devised to take into consideration compound efficacy, its potential interference with the assay and the screening stage that the data was obtained. Details of the Scoring System will be published elsewhere. Briefly, the outline of the scoring system utilized for the assay is as follows:

1) First tier (0-40 range) is reserved for primary screening data. The score is correlated with % activity in the assay. Scoring for the primary screening is not applicable to this assay.
2) Second tier (41-80 range) is reserved for dose-response confirmation data
   a. Inactive compounds of the confirmatory stage are assigned a score value equal 41.
   b. The score is linearly correlated with a compound's potency and, in addition, provides a measure of the likelihood that the compound is not an artifact based on the available information.
  c. The Hill coefficient is taken as a measure of compound behavior in the assay via an additional scaling factor QC:

$$QC=2.6*[\exp(-0.5*nH\wedge 2)-\exp(-1.5*nH\wedge 2)]$$

This empirical factor prorates the likelihood of target- or pathway-specific compound effect vs. its non-specific behavior in the assay. This factor is based on expectation that a compound with a single mode of action that achieved equilibrium in the assay demonstrates the Hill coefficient value of 1. Compounds deviating from that behavior are penalized proportionally to the degree of their deviation.
  d. Summary equation that takes into account all the items discussed above is $$\text{Score}=44+6*(pIC_{50}-3)*QC,$$

Where $pIC_{50}$ is a negative log(10) of the $IC_{50}$ value expressed in mole/L concentration units. This equation results in the Score values above 50 for compounds that demonstrate high potency and predictable behavior. Compounds that are inactive in the assay or whose concentration-dependent behavior are likely to be an artifact of that assay will generally have lower Score values.

3) Third tier (81-100 range) is reserved for resynthesized true positives and their analogues and is not applicable in this assay.

Dose Response Confirmation of μHTS Inhibitor Hits of the Mitochondrial Permeability Transition Pore Via a Fluorescent Based Counterscreen Assay (Counterscreen Assay, Concentration-Response, AID No. 651564)

List of Reagents:
Assay Buffer: 250 mM sucrose, 10 mM MOPS-Tris, 0.01 mM EGTA-Tris, 1.0 mM phosphoric acid-Tris, pH 7.4.
  Solution 1: 0.5 mg/mL mitochondria in Assay Buffer.
  Solution 2: 0.8 μM Rh123, 5.0 mM glutamate and 2.5 mM malate in Assay Buffer.

Protocol Summary:
1. Compounds are pre-spotted into assay plates the morning of or the night before the assay. Via the LabCyte Echo, varying volumes of 10 mM test compounds in DMSO are transferred to a Greiner, 1536-well, clear assay plates (Greiner 782101) to achieve appropriate test volume concentrations and range. Varying volumes of DMSO are transferred to the wells of the assay plate to equilibrate its concentration between wells for a total volume of 64 nL of DMSO per well or 0.8% final assay concentration. Positive and negative control wells will also contain 64 nL of DMSO.
2. Prepare Assay Buffer, Rh123 Solution and the mitochondrial suspension working stocks according to the recipes in the Reagent Section.
3. Freshly isolated mitochondria from mice are suspended in Assay Buffer (Solution 1) and 10 μL of this solution is added to all wells of the assay plate with a MultiDrop Combi. Final assay concentration of mitochondria will be about 0.25 mg/mL (Working Stock ~0.5 mg/mL), depending on relative activity of mitochondrial preparation.
4. Following the addition of the mitochondrial suspension, 10 μL of Rh123 Solution (Solution 2) is added to each well of the assay plate.
5. Assay plate is immediately spun at 1000 rpm for ~60 seconds.
6. Plate is kept at room temperature for 5 minutes and then read on the BMG Pherastar utilizing a fluorescence intensity optical module that allows for excitation at 480 nm and a read at an emission wavelength of 520 nm.

Comments:
Compounds that demonstrated an $EC_{50}$ of 80 μM or less are defined as active in this assay.

To simplify the distinction between the inactives of the primary screen and of the confirmatory screening stage, the Tiered Activity Scoring System was developed and implemented.

Activity Scoring:
Activity scoring rules were devised to take into consideration compound efficacy, its potential interference with the assay and the screening stage that the data was obtained. Details of the Scoring System will be published elsewhere. Briefly, the outline of the scoring system utilized for the assay is as follows:

1) First tier (0-40 range) is reserved for primary screening data and is not applicable in this assay.
2) Second tier (41-80 range) is reserved for dose-response confirmation data
  a. Inactive compounds of the confirmatory stage are assigned a score value equal 41.
  b. The score is linearly correlated with a compound's potency and, in addition, provides a measure of the likelihood that the compound is not an artifact based on the available information.
  c. The Hill coefficient is taken as a measure of compound behavior in the assay via an additional scaling factor QC:

$$QC=2.6*[\exp(-0.5*nH\wedge 2)-\exp(-1.5*nH\wedge 2)]$$

This empirical factor prorates the likelihood of target- or pathway-specific compound effect vs. its non-specific behavior in the assay. This factor is based on expectation that a compound with a single mode of action that achieved equilibrium in the assay demonstrates the Hill coefficient value of 1. Compounds deviating from that behavior are penalized proportionally to the degree of their deviation.
  d. Summary equation that takes into account all the items discussed above is $$\text{Score}=44+6*(pIC_{50}-3)*QC,$$

Where $pIC_{50}$ is a negative log(10) of the $IC_{50}$ value expressed in mole/L concentration units. This equation results in the Score values above 50 for compounds that demonstrate high potency and predictable behavior. Compounds that are inactive in the assay or whose concentration-dependent behavior are likely to be an artifact of that assay will generally have lower Score values.

3) Third tier (81-100 range) is reserved for resynthesized true positives and their analogues and is not applicable in this assay.

Dry Powder Dose Response Confirmation of μHTS Inhibitor Hits of the Mitochondrial Permeability Transition Pore Via an Absorbance. Mitochondrial Swelling (Hit Validation, Confirmatory Assay, Concentration-Response, AID No. 720722)

List of Reagents:
Assay buffer: 250 mM sucrose, 10 mM MOPS-Tris, 0.01 mM EGTA-Tris, 1.0 mM phosphoric acid-Tris, pH 7.4
  Solution 1. 5.0 mM glutamate and 2.5 mM malate in Assay buffer.
  Solution 2. 80-120 μM $CaCl_2$) depending on mitochondrial activity in Solution 1. Note: Concentration of $Ca^{2+}$ in the assay is dependent upon the activity of the isolated mitochondria which is determined via a calcium titration just before each screening batch. A Ca$^{2+}$ concentration is used that allows for the arrival at a 2:1 window at the 20 minute time period.

Solution 3. 1% DMSO in Solution 2.
Solution 4. 2.0 mM EGTA-Tris, pH 7.4 in Solution 3.
Solution 5. 0.5 mg/mL mitochondria in Assay Buffer.

Protocol Summary:
1. Freshly isolate mitochondria, prepare solutions according to the recipes in the reagent section
2. Dispense 100 µL of Solution 4 to Columns 1-2 and Solution 3 Columns 11-12 (positive and negative controls, respectively) of the 96-well clear assay plate (Falcon 353072)
3. Dispense 200 µL of Solution 1 to Row A Columns 3-10.
4. Next, dispense 100 µL of Solution 3 to Rows B-H Columns 3-10.
5. Add 4 µL of 5 mM test compounds in DMSO to Row A Columns 3-10, perform 1:2 serial dilutions Row A to H Columns 3-10.
6. Finally, dispense 100 µl of Solution 5 in all wells. The reaction starts.
7. Keep the plate at room temperature for 20 minutes and then read absorbance at 540 nm on MultiSkan EX, Thermo Scientific.

Comments:
Compounds that demonstrated an EC$_{50}$ of 20 µM or less are defined as active in this assay.

To simplify the distinction between the inactive compounds of the primary screen and of the confirmatory screening stage, the Tiered Activity Scoring System was developed and implemented.

Activity Scoring:
Activity scoring rules were devised to take into consideration compound efficacy, its potential interference with the assay and the screening stage that the data was obtained. Details of the Scoring System will be published elsewhere. Briefly, the outline of the scoring system utilized for the assay is as follows:
1) First tier (0-40 range) is reserved for primary screening data and is not applicable in this assay.
2) Second tier (41-80 range) is reserved for dose-response confirmation data and is not applicable in this assay.
3) Third tier (81-100 range) is reserved for resynthesized true positives and their analogues.
   a. Compounds that failed to reproduce from dry powder or have IC$_{50}$>20 M are assigned inactive and a score value of 81.
   b. The score is linearly correlated with a compound's potency and, in addition, provides a measure of the likelihood that the compound is not an artifact based on the available information. The Hill coefficient is taken as a measure of compound behavior in the assay via an additional scaling factor QC:

$$QC=2.6*[\exp(-0.5*nH;2)-\exp(-1.5*nH;2)]$$

This empirical factor prorates the likelihood of a target- or a pathway-specific compound effect vs. its non-specific behavior in the assay. This factor is based on the expectation that a compound with a single mode of action that achieved an equilibrium in the assay would demonstrate the Hill coefficient value of 1. Compounds deviating from that behavior are penalized proportionally to the degree of their divergence.
   c. The score is calculated using the following equation:

$$\text{Score}=82+3*(pIC_{50}-3)*QC,$$

where pIC$_{50}$ is a negative log(10) of the IC$_{50}$ value expressed in mole/L concentration units, and QC is calculated using Hill coefficient as above. This equation results in the Score values above 85 for compounds that demonstrate high potency and predictable behavior in the assays.

Dry Powders Dose Response Confirmation of µHTS Inhibitor Hits of the Mitochondrial Permeability Transition Pore Via a Fluorescent Based Counterscreen. Rhodamine 123 Quenching (Hit Validation, Counterscreen Assay, Concentration-Response, AID No. 720723)

List of Reagents:
Assay buffer: 250 mM sucrose, 10 mM MOPS-Tris, 0.01 mM EGTA-Tris, 1.0 mM phosphoric acid-Tris, pH 7.4
Solution 1. 5.0 mM glutamate and 2.5 mM malate in Assay Buffer.
Solution 2. 1% DMSO in Solution 1.
Solution 3. 0.8 µM FCCP (the stock 40 µM in DMSO) in Solution 1.
Solution 4. 0.5 mg/mL mitochondria and 0.8 µM Rh123 in Assay Buffer.

Protocol Summary:
1. Freshly isolate mitochondria, prepare solutions according to the recipes in the Reagent Section.
2. Dispense 100 µL of Solution 3 to Columns 1-2 and Solution 2 Columns 11-12 (positive and negative controls, respectively) of the 96-well black assay plate (Falcon 353376).
3. Dispense 200 µL of Solution 1 to Row A Columns 3-10.
4. Next, dispense 100 µL of Solution 2 to Rows B-H Columns 3-10.
5. Add 4 µL of 10 mM test compounds in DMSO to Row A Columns 3-10, perform 1:2 serial dilutions Row A to H Columns 3-10.
6. Finally, dispense 100 µL of Solution 4 in all wells. The reaction starts.
7. Keep the plate at room temperature for 5 minutes and then read fluorescence (excitation 485 nm, emission 538 nm) on Fluoroskan Ascent Fla., Thermo Scientific.

Comments:
Compounds that demonstrated an EC$_{50}$ of 100 µM or less are defined as active in this assay.

To simplify the distinction between the inactives of the primary screen and of the confirmatory screening stage, the Tiered Activity Scoring System was developed and implemented.

Activity Scoring:
Activity scoring rules were devised to take into consideration compound efficacy, its potential interference with the assay and the screening stage that the data was obtained. Details of the Scoring System will be published elsewhere. Briefly, the outline of the scoring system utilized for the assay is as follows:
1) First tier (0-40 range) is reserved for primary screening data and is not applicable in this assay.
2) Second tier (41-80 range) is reserved for dose-response confirmation data and is not applicable in this assay.
3) Third tier (81-100 range) is reserved for resynthesized true positives and their analogues.
   a. Compounds that failed to reproduce from dry powder or have IC$_{50}$>100 M are assigned inactive and a score value of 81.
   b. The score is linearly correlated with a compound's potency and, in addition, provides a measure of the likelihood that the compound is not an artifact based on the available information. The Hill coefficient is taken as a measure of compound behavior in the assay via an additional scaling factor QC:

$$QC=2.6*[\exp(-0.5*nH;2)-\exp(-1.5*nH;2)]$$

This empirical factor prorates the likelihood of a target- or a pathway-specific compound effect vs. its non-specific behavior in the assay. This factor is based on the expectation that a compound with a single mode of action that achieved an equilibrium in the assay would demonstrate the Hill coefficient value of 1. Compounds deviating from that behavior are penalized proportionally to the degree of their divergence.

c. The score is calculated using the following equation:

$$\text{Score}=82+3*(pIC_{50}-3)*QC,$$

where $pIC_{50}$ is a negative log(10) of the $IC_{50}$ value expressed in mole/L concentration units, and QC is calculated using Hill coefficient as above. This equation results in the Score values above 85 for compounds that demonstrate high potency and predictable behavior in the assays.

Dry Powder Dose Response Confirmation µHTS Inhibitor Hits of the Mitochondrial Permeability Transition Pore Via Calcium Retention Capacity Test (Hit Validation, Confirmatory Assay, Concentration-Response, AID No. 720728)

List of Reagents:
Assay buffer: 250 mM sucrose, 10 mM MOPS-Tris, 0.01 mM EGTA-Tris, 1.0 mM phosphoric acid-Tris, pH 7.4.
Solution 1. 10 mM glutamate and 5 mM malate in Assay buffer.
Solution 2. 1% DMSO in Solution 2.
Solution 3. 0.5 mg/mL mitochondria and 1.0 µM Calcium Green-5N in Assay Buffer.
Solution 4. 0.25 mM $CaCl_2$.

Protocol Summary:
1. Freshly isolate mitochondria, prepare solutions according to the recipes in the Reagent Section.
2. Dispense 100 µL of Solution 2 to Columns 1-2 (negative control) of the 96-well black assay plate (Falcon 353376).
3. Dispense 200 µL of Solution 1 to Row A Columns 3-12.
4. Next, dispense 100 µL of Solution 2 to Rows B-H Columns 3-12.
5. Add 4 µL of 5 mM test compounds in DMSO to Row A Columns 3-12, perform 1:2 serial dilutions Row A to H Columns 3-12.
6. Finally, dispense 100 µL of Solution 3 in all wells.
7. Experiment starts. Read Calcium Green-5N fluorescence (excitation 485 nm, emission 538 nm) and perform a train of 4 µL Solution 4 additions with Fluoroskan Ascent Fla., Thermo Scientific.

Comments:
Compounds that demonstrated a $CRC/CRC_0$ of above 1.1 at 12.5 µM are defined as active in this assay.

Concentration-Response Assay to Identify Compounds that Inhibit Mitochondrial Swelling (SAR Assay AID No. 743359)

List of Reagents:
Assay buffer: 250 mM sucrose, 10 mM MOPS-Tris, 0.01 mM EGTA-Tris, 1.0 mM phosphoric acid, pH 7.4
Solution 1. 5.0 mM glutamate and 2.5 mM malate in Assay Buffer.
Solution 2. 100-120 µM $CaCl_2$) depending on mitochondrial activity in Solution 1. Note: Concentration of $Ca^{2+}$ in the assay is dependent upon the activity of the isolated mitochondria which is determined via a calcium titration just before each screening batch. A $Ca^{2+}$ concentration is used that allows for the arrival at a 2:1 window at the 20 minute time period.
Solution 3. 1% DMSO in Solution 2.
Solution 4. 2.0 mM EGTA-Tris, pH 7.4 in Solution 3.
Solution 5. 0.5 mg/mL mitochondria in Assay Buffer.

Protocol Summary:
1. Freshly isolate mitochondria, prepare solutions according to the recipes in the Reagent Section.
2. Dispense 100 µL of Solution 4 to Columns 1-2 and Solution 3 Columns 11-12 (positive and negative controls, respectively) of the 96-well clear assay plate (Falcon 353072).
3. Dispense 200 µL of Solution 1 to Row A Columns 3-10.
4. Next, dispense 100 µL of Solution 3 to Rows B-H Columns 3-10.
5. Add 4 µL of 5 mM test compounds in DMSO to Row A Columns 3-10, perform 1:2 serial dilutions Row A to H Columns 3-10.
6. Finally, dispense 100 µL of Solution 5 in all wells. The reaction starts.
7. Keep the plate at room temperature for 20 minutes and then read absorbance at 540 nm on MultiSkan EX, Thermo Scientific.

Comments:
Compounds that demonstrated an $EC_{50}$ of 20 µM or less are defined as active in this assay.

To simplify the distinction between the inactives of the primary screen and of the confirmatory screening stage, the Tiered Activity Scoring System was developed and implemented.

Activity Scoring:
Activity scoring rules were devised to take into consideration compound efficacy, its potential interference with the assay and the screening stage that the data was obtained. Details of the Scoring System will be published elsewhere. Briefly, the outline of the scoring system utilized for the assay is as follows:

1) First tier (0-40 range) is reserved for primary screening data and is not applicable in this assay.
2) Second tier (41-80 range) is reserved for dose-response confirmation data and is not applicable in this assay.
3) Third tier (81-100 range) is reserved for resynthesized true positives and their analogues.
   a. Compounds that failed to reproduce from dry powder or have $IC_{50}$>20 M are assigned inactive and a score value of 81.
   b. The score is linearly correlated with a compound's potency and, in addition, provides a measure of the likelihood that the compound is not an artifact based on the available information. The Hill coefficient is taken as a measure of compound behavior in the assay via an additional scaling factor QC:

$$QC=2.6*[\exp(-0.5*nH;2)-\exp(-1.5*nH;2)]$$

This empirical factor prorates the likelihood of a target- or a pathway-specific compound effect vs. its non-specific behavior in the assay. This factor is based on the expectation that a compound with a single mode of action that achieved an equilibrium in the assay would demonstrate the Hill coefficient value of 1. Compounds deviating from that behavior are penalized proportionally to the degree of their divergence.

c. The score is calculated using the following equation:

$$\text{Score}=82+3*(pIC_{50}-3)*QC,$$

where $pIC_{50}$ is a negative log(10) of the $IC_{50}$ value expressed in mole/L concentration units, and QC is calculated using Hill coefficient as above. This equation results in the Score values above 85 for compounds that demonstrate high potency and predictable behavior in the assays.

Concentration-Response Counterscreen Assay to Identify Compounds that Prevent Mitochondrial Swelling Via Interference with the IMM Potential (SAR Assay AID No. 743361)

List of Reagents:

Assay buffer: 250 mM sucrose, 10 mM MOPS-Tris, 0.01 mM EGTA-Tris, 1.0 mM phosphoric acid-Tris, pH 7.4

Solution 1. 5.0 glutamate and 2.5 mM malate in Assay Buffer.
Solution 2. 1% DMSO in Solution 1.
Solution 3. 0.8 μM FCCP (the stock 40 μM in DMSO) in Solution 1.
Solution 4. 0.5 mg/mL mitochondria and 0.8 μM Rh123 in Assay Buffer.

Protocol Summary:

1. Freshly isolate mitochondria, prepare solutions according to the recipes in the Reagent Section.
2. Dispense 100 μl of Solution 3 to Columns 1-2 and Solution 2 Columns 11-12 (positive and negative controls, respectively) of the 96-well black assay plate (Falcon 353376).
3. Dispense 200 μL of Solution 1 to Row A Columns 3-10.
4. Next, dispense 100 μL of Solution 2 to Rows B-H Columns 3-10.
5. Add 4 μL of 10 mM test compounds in DMSO to Row A Columns 3-10, perform 1:2 serial dilutions Row A to H Columns 3-10.
6. Finally, dispense 100 μL of Solution 4 in all wells. The reaction starts.
7. Keep the plate at room temperature for 5 minutes and then read fluorescence (excitation 485 nm, emission 538 nm) on Fluoroskan Ascent Fla., Thermo Scientific.

Comments:

Compounds that demonstrated an $EC_{50}$ of 100 μM or less are defined as active in this assay.

To simplify the distinction between the inactives of the primary screen and of the confirmatory screening stage, the Tiered Activity Scoring System was developed and implemented.

Activity Scoring:

Activity scoring rules were devised to take into consideration compound efficacy, its potential interference with the assay and the screening stage that the data was obtained. Details of the Scoring System will be published elsewhere. Briefly, the outline of the scoring system utilized for the assay is as follows:

1) First tier (0-40 range) is reserved for primary screening data and is not applicable in this assay
2) Second tier (41-80 range) is reserved for dose-response confirmation data and is not applicable in this assay.
3) Third tier (81-100 range) is reserved for resynthesized true positives and their analogues.
   a. Compounds that failed to reproduce from dry powder or have $EC_{50}$>100 M are assigned inactive and a score value of 81.
   b. The score is linearly correlated with a compound's potency and, in addition, provides a measure of the likelihood that the compound is not an artifact based on the available information. The Hill coefficient is taken as a measure of compound behavior in the assay via an additional scaling factor QC:

$$QC=2.6*[exp(-0.5*nH;2)-exp(-1.5*nH;2)]$$

This empirical factor prorates the likelihood of a target- or a pathway-specific compound effect vs. its non-specific behavior in the assay. This factor is based on the expectation that a compound with a single mode of action that achieved an equilibrium in the assay would demonstrate the Hill coefficient value of 1. Compounds deviating from that behavior are penalized proportionally to the degree of their divergence.

c. The score is calculated using the following equation:

$$Score=82+3*(pIC_{50}-3)*QC,$$

where $pIC_{50}$ is a negative log(10) of the $IC_{50}$ value expressed in mole/L concentration units, and QC is calculated using Hill coefficient as above. This equation results in the Score values above 85 for compounds that demonstrate high potency and predictable behavior in the assays.

Calcium Retention Capacity Assay to Assess the Propensity of the mtPTP to Open as a Function of Test Compound Concentration (SAR Assay AID No. 743360)

List of Reagents:

Assay buffer: 250 mM sucrose, 10 mM MOPS-Tris, 0.01 mM EGTA-Tris, 1.0 mM phosphoric acid-Tris, pH 7.4.

Solution 1. 10 mM glutamate and 5 mM malate in Assay buffer.
Solution 2. 1% DMSO in Solution 2.
Solution 3. 0.5 mg/mL mitochondria and 1.0 μM Calcium Green-5N in Assay Buffer.
Solution 4. 0.25 mM $CaCl_2$.

Protocol Summary:

1. Freshly isolate mitochondria, prepare solutions according to the recipes in the Reagent Section.
2. Dispense 100 μL of Solution 2 to Columns 1-2 (negative control) of the 96-well black assay plate (Falcon 353376).
3. Dispense 200 μL of Solution 1 to Row A Columns 3-12.
4. Next, dispense 100 μL of Solution 2 to Rows B-H Columns 3-12.
5. Add 4 μL of 5 mM test compounds in DMSO to Row A Columns 3-12, perform 1:2 serial dilutions Row A to H Columns 3-12.
6. Finally, dispense 100 μL of Solution 3 in all wells.
7. Experiment starts. Read Calcium Green-5N fluorescence (excitation 485 nm, emission 538 nm) and perform a train of 4 μL Solution 4 additions with Fluoroskan Ascent Fla., Thermo Scientific.

Comments:

Compounds that demonstrated a $CRC/CRC_0$ of above 1.1 at 12.5 μM are defined as active in this assay.

Calcium Retention Capacity of Permeabilized Cells

Cell Growth and Permeabilization:

HeLa and MEF cells were cultured in Dulbecco's Modified Eagle Medium (Gibco) in the presence of 10% Fetal Bovine Serum and 1% penicillin-streptomycin for 48 hours to reach a 70-80% confluency. On the day of the experiment cells were harvest, suspended in 130 mM KCl, 10 MOPS-Tris, 1 mM phosphoric acid-Tris, 1 mM EGTA-Tris, pH 7.4 to 20 million/mL, and treated with 100 μM digitonin (Calbiochem) for 10 min on ice to permeabilize the plasma membrane. Cells were then washed twice and resuspended in the above buffer except that 100 μM EGTA-Tris was used.

List of Reagents:

Assay Buffer: 130 mM KCl, 10 MOPS-Tris, 1 mM phosphoric acid-Tris, 10 μM EGTA-Tris, pH 7.4

Solution 1. 10 mM glutamate and 5 mM malate in Assay Buffer.
Solution 2. 1% DMSO in Solution 2.

Solution 3. 8 million/mL cells and 1.0 µM Calcium Green-5N in Assay Buffer.

Solution 4. 0.5 mM CaCl$_2$.

Protocol Summary:

1. Harvest and permeabilize the cells according to the instructions above.
2. Dispense 100 µL of Solution 2 to Columns 1-2 (negative control) of the 96-well black assay plate (Falcon 353376).
3. Dispense 200 µL of Solution 1 to Row A Columns 3-12.
4. Next, dispense 100 µL of Solution 2 to Rows B-H Columns 3-12.
5. Add 4 µL of 5 mM test compounds in DMSO to Row A Columns 3-12, perform 1:2 serial dilutions Row A to H Columns 3-12.
6. Finally, dispense 100 µL of Solution 3 in all wells.
7. Experiment starts. Read Calcium Green-5N fluorescence (excitation 485 nm, emission 538 nm) and perform a train of 4 µL Solution 4 additions with Fluoroskan Ascent Fla., Thermo Scientific.

HeLa Cell Viability Assay

HeLa cells were plated in a 96-well plate at 1800 cells/well and treated with a compound for 72 hours over a 9 point 2-fold dilution series, ranging from 0.78 µM to 200 µM. Following 72 hours of treatment, relative viable cell number was determined using CellTiter 96® AQueous One Solution Cell Proliferation Assay from Promega. Each compound treatment was performed in 8—while DMSO treatment in 16—replicates, the latter ones serving as positive controls.

Experimental Procedures for Physiochemcial and In Vitro Pharmacokinetic Property Assays Aqueous Solubility: Solubility analysis was performed using a direct UV kinetic solubility method in a 96-well format. All liquid dispense and transfer steps were performed with the Freedom Evo automated liquid handler (Tecan US). Solubility measurements were performed in an aqueous buffer solution (System Solution, pION Inc, P/N 110151) at pH 5.0, 6.2 and 7.4, in duplicate. Samples were incubated at room temperature for a minimum of 18 hrs to achieve equilibrium, then filtered (filter plate, pION Inc, P/N 110322) to remove any precipitate formed. The concentration of the compounds was measured by UV absorbance (250-498 nm) using the Infinite M200 (Tecan US) and compared to the spectra of the precipitation-free reference solutions. Spectroscopically pure 1-Propanol (Sigma P/N 256404) was used as a cosolvent to suppress precipitation in the reference solutions. The solubility of each compound was determined using µSOL Evolution Plus software v3.2 (pION Inc) and is expressed as the concentration (µg/mL) of a solute in a saturated solution.

Assay Details:

Diclofenac Na and Dipyridamole were used as standards. Diclofenac Na is highly soluble. Dipyridamole is poorly to moderately soluble.

Standards and test compound stocks were made in 100% DMSO

Assay concentration of standards: 500 µM and test compound: 300 µM

Cosolvent used in the reference solution to suppress precipitation: 1-Propanol

Assay DMSO final concentration: 1%

Aqueous and Thiol Stability: Compound was dissolved at 10 µM in 1:1 ACN:PBS and incubated at room temperature with either no thiol source as a negative control, 50 µM glutathione (GSH), or 50 µM dithiothreitol (DTT). The mixtures were sampled every hour for eight hours or every 8 hours for 88 hours and analyzed by RP HPLC/UV/HRMS. The analytical RP HPLCUV/HRMS system utilized for the analysis was a Waters Acquity system with UV-detection and mass-detection (Waters SQD). The analytical method conditions included a Waters Acquity HSS Atlantis C18 column (2.1×50 mm, 1.8 um) and elution with a linear gradient of 99% water to 100% CH$_3$CN at 0.6 mL/min flow rate. Peaks on the 214 nm chromatographs were integrated using the Waters OpenLynx software. Absolute areas under the curve were compared at each time point to determine relative percent compound remaining. The masses of potential adducts were searched for in the final samples to determine if any detectable adduct formed. All samples were prepared in duplicate and the average plotted. Ethacrynic acid, a known Michael acceptor, was used as a positive control.

Plasma Stability: Stability of the compound in human plasma (BioChemed Services, P/N 752PR-EK3-PMG) was determined. All liquid dispense and transfer steps were performed with the Freedom Evo automated liquid handler (Tecan US). Plasma was allowed to thaw at room temperature prior to preparing the assay solution of plasma:1×PBS (1:1). The assay solution was warmed up at 37° C. prior of adding the compound. Immediately after compounds were added, time 0 min aliquots were promptly collected and mixed with cold acetonitrile (spiked with an internal standard). The remainder of the reaction volume was incubated at 37° C. with shaking. Additional aliquots were collected 180 min after the start of the reaction and promptly quenched with cold acetonitrile (spiked with an internal standard). Samples were centrifuged at 3000 rpm for 10 min. The amount of compound in the supernatant was determined by LC/MS/MS (Applied Biosystems, Sciex API4000 Q-Trap) and the percent of parent compound remaining after 180 min was calculated by the following formula:

$$\% \text{ parent compound remaining} = \left[\frac{\text{Concentration at 180 min}}{\text{Concentration at 0 min}} \times 100\right]$$

Results reported are the mean of each reaction duplicate, normalized to the internal standard, and expressed as a percent of compound remaining after the incubation time.

Assay Details:

Human Plasma in K3 EDTA

Procaine and Procainamide were used as standards. Procaine is highly unstable in human plasma, Procainamide is highly stable in human plasma.

Assay concentrations of standards and test compound: 1 µM

Incubation Time: 3 hrs

Reaction pH: 7.4

Assay DMSO final concentration: 2.5%

Hepatic Microsome Stability: Metabolic stability was assessed in the presence of human liver microsomes (XenoTech, P/N H0630) and mouse liver microsomes (XenoTech, P/N M1000). All liquid dispense and transfer steps were performed with the Freedom Evo automated liquid handler (Tecan US). NADPH, a required cofactor for CYP450 metabolism, was provided by the NADPH Regenerating System, Solutions A (BD Biosciences, P/N 451220) and B (BD Biosciences, P/N 451200). Compound stock solutions were initially prepared in 100% DMSO and subsequently diluted in acetonitrile for the assay. The pH of the reactions was kept at ~7.4 with potassium phosphate buffer (BD Biosciences, P/N 451201). The reactions were started after adding NADPH to the reaction plate containing microsomes and compounds and time 0 min aliquots were promptly collected and mixed with ice cold acetonitrile (spiked with internal standards) to quench the reactions. The remainder of the reaction volume was incubated at 37° C. with shaking. Additional aliquots were collected 60 min after the start of the reaction and promptly quenched with ice cold acetonitrile (spiked with an internal standard). Samples were centrifuged at 3000 rpm for 10 min. The amount of compound in the supernatant was determined by LC/MS/MS (Applied Biosystems, Sciex API4000 Q-Trap) and the percent of parent compound remaining after 60 min was calculated by the following formula:

$$\% \text{ parent compound remaining} = \left[ \frac{\text{Concentration at 60 min}}{\text{Concentration at 0 min}} \times 100 \right]$$

All reactions were run in triplicate, except negative controls (no NADPH) which were performed as single reactions. Results reported are the mean of each reaction triplicate, normalized to the internal standard, and expressed as a percent compound remaining after the incubation time.

Assay Details:
Human and Mouse Liver Microsomes: 0.5 mg/mL protein concentration
NADPH Regenerating System: 1.55 mM NADP+, 1.33 mM glucose-6-phosphate, 1.33 mM Magnesium chloride, and 0.4 U/mL glucose-6 phosphate dehydrogenase
Incubation Temperature: 37° C.
Incubation Time: 60 min
Standards: Verapamil-HCl and Testosterone, at 20 µM and 50 µM, respectively
Test compound at 1 µM
Assay DMSO final concentration: ≤0.5%
Assay ACN final concentration: ≤1.2%

Cellular Permeability: Permeability was assessed using the Parallel Artificial Membrane Permeability Assay, PAMPA in a 96-well format. All liquid dispense and transfer steps were performed with the Freedom Evo automated liquid handler (Tecan US). Measurements were performed in 20% ACN and aqueous buffer solution (System Solution, pION Inc, P/N 110151) at pH 5.0, 6.2, and 7.4, in duplicate. A "sandwich" plate (pION Inc, P/N 110212) consisting of a donor bottom plate and an acceptor filter plate was used. The donor wells contained the compounds in 180 µl system solution, and magnetic stir bars. The filter on the bottom of each acceptor well was coated with GIT-0 lipid (pION Inc, P/N 110669) and filled with 200 µl of Acceptor Sink Buffer, pH 7.4 (pION Inc, P/N 110139) containing a surfactant to mimic the function of serum proteins. The permeation time was 30 min and moderate stirring (equivalent to 40 µm Aqueous Boundary Layer thickness) was applied using the Gut-Box™ (pION, Inc, P/N 110205). After the permeation time, the sandwich was disassembled and the amount of compound present in both the donor and acceptor wells was measured by UV absorbance (250-498 nm) using the Infinite M200 (Tecan US) and compared to spectra obtained from reference standards. Mass balance was used to determine the amount of material embedded in the membrane filter. The effective permeability, Pe, was calculated using the software PAMPA Evolution Plus, version 3.2 (pION Inc).

Assay Details:
Verapamil HCl, Metoprolol, and Ranitidine were used as reference standards
Verapamil HCl is considered highly permeable
Metoprolol is considered moderately permeable
Ranitidine is considered poorly permeable
Permeation time: 30 min
Moderate stirring (equivalent to 40 µm ABL, aqueous boundary layer, also known as the unstirred water layer)
Donor buffer pH: 5.0, 6.2 and 7.4
Double-Sink: pH gradients between donor and acceptor compartments; acceptor buffer contains chemical sink
Assay DMSO final concentration: 0.5%

Membrane Permeability through the blood-brain barrier: Permeability was assessed using an in vitro model for the passive transport through the blood-brain barrier, BBB-PAMPA. For this, the Parallel Artificial Membrane Permeability Assay (PAMPA) in a 96-well format was used. All liquid dispense and transfer steps were performed with the Freedom Evo automated liquid handler (Tecan US). Measurements were performed in an aqueous buffer solution (System Solution, pION Inc, P/N 110151) at pH 7.4, in quadruplicate. A "sandwich" plate (pION Inc, P/N 110212) consisting of a donor bottom plate and an acceptor filter plate was used. The donor wells contain the compounds in 180 µl system solution, and magnetic stir bars. The filter on the bottom of each acceptor well is coated with BBB-1 lipid solution (pION Inc, P/N 110672) and filled with 200 µl of Brain Sink Buffer, pH 7.4 (pION Inc, P/N 110674) also containing a surfactant. The permeation time is 60 min. Moderate stirring (equivalent to 40 µM Aqueous Boundary Layer thickness) is applied using the Gut-Box™ (pION, Inc, P/N 110205). After the permeation time, the sandwich is disassembled and the amount of compound present in both the donor and acceptor wells is measured by UV absorbance (250-498 nm) using the Infinite M200 (Tecan US) and compared to spectra obtained from reference standards. Mass balance is used to determine the amount of material embedded in the membrane filter. The effective permeability, $P_e$, is calculated using the software PAMPA Evolution Plus, version 3.2 (pION Inc). The calculated effective permeability, $P_e$, is expressed as a kinetic parameter (centimeter per second). A larger number indicates greater speed and thus greater permeability. Log $P_e$ is often used to report permeability, and is inversely proportional to $P_e$; thus the smaller Log $P_e$ value indicates greater permeability.

Assay Details:
Verapamil-HCl, Corticosterone, and Theophylline are used as reference standards: Verapamil-HCl is considered highly permeable, Corticosterone is considered moderately permeable, and Theophylline is considered poorly permeable.
Permeation time: 60 min
Moderate stirring (equivalent to 40 µm ABL, aqueous boundary layer, also known as the unstirred water layer)
Donor buffer pH: 7.4; Acceptor buffer pH: 7.4
Assay DMSO assay concentration: 0.5%

Plasma Protein Binding: Teflon® Base Plate wells were rinsed with 20% ethanol for 10 minutes. Ethanol was then removed and wells were rinsed with ultrapure water and allowed to dry. RED Inserts from Thermo Scientific (Pierce) were placed (open end up) into the wells of the base plate. All liquid dispense and transfer steps were performed with the Freedom Evo automated liquid handler (Tecan US). The sample chambers (red ring) contained 300 µl of a mixture of plasma and compound. And 500 µl of dialysis buffer (1×PBS, pH7.4) were added to the buffer chambers of the inserts. Duplicate inserts were made for each concentration tested. The base plate was covered with sealing tape and incubated at 37° C. on an orbital shaker at 300 rpm for 4 hours. After the incubation time, equal volume from both chambers were removed and transferred to a 96 well plate containing either plasma or buffer. To precipitate proteins and release compounds, ice cold acetonitrile (with an internal standard) was added. Samples were centrifuged for 10 minutes at 3000 rpm. The amount of compound in the supernatant was determined by LC/MS/MS (Applied Biosystems, Sciex API4000 Q-Trap). The percent of free and bound compounds were calculated with the following formulas:

$$\% \text{ of free parent compound} = \left[\frac{\text{amount of compound in receiver chamber}}{\text{amount of compound in donor chamber}} \times 100\right]$$

% of bound parent compound = 100 − % of free compound

Results reported are the mean of each reaction duplicate, normalized to the internal standard, and expressed as a percent compound bound after the incubation time.
Assay Details:
Human Plasma in K3 EDTA
Propanolol and Metoprolol were used as standards. Propanolol is highly bound, Metoprolol is poorly bound
Assay concentrations of standards and test compounds: 1 µM and 10 µM
Incubation Time: 4 hrs
Reaction pH: 7.4
Assay DMSO final concentration: 1%
Cytotoxicity: Immortalized human hepatocytes, Fa2N-4 cells (XenoTech) were seeded at ~56,000 cells/well, and incubated with a range of concentrations (0.01-50 µM) of the test compound, in duplicate, for 24 hrs at 37° C., 5% $CO_2$. Cell viability was determined by cellular ATP levels using the Luminescence ATP Detection Assay System (ATPlite 1 step, Perkin Elmer, #6016731) and the Infinite M200 plate reader (Tecan).
Assay Details:
Cells used: Fa2N-4, immortalized human hepatocytes
Media used for Fa2N-4 cells: MFE Plating and MFE Support (with 1% Penicillin, Streptomycin, and Amphotercin mixture)
Assay DMSO final concentration=0.5%
Treatment time: 24 hrs
Camptothecin and Terfenadine were used as standards. Camptothecin is highly toxic and Terfenadine is highly non toxic.

Biological Results

The following are tabulated biological results from the aforementioned assays, were values are given as the average over at least three experiments with the standard error of the mean (SEM), e.g. "average±SEM":

TABLE 1

Isoxazole and Benzamide Calcium Retention Capacity; Mitochondrial Swelling; and Rhodamine 123 (Rh123) uptake

| Structure | Calcium Retention Capacity ($CRC/CRC_0$ at 12.5 µM) | Mitochondrial swelling (EC50) | Rh123 uptake (EC50) |
|---|---|---|---|
| 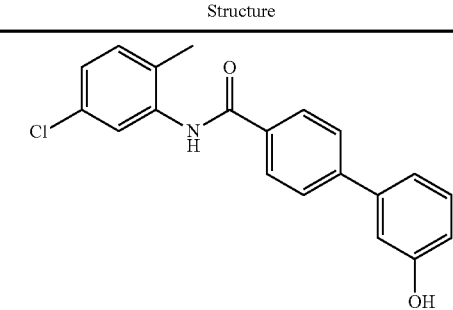 | 2.59 ± 0.22 | 4.710 ± 0.3490 µM | >100 µM |
| (3,5-dichloro isoxazole methoxy phenol structure) | 1.17 ± 0.11 (at 1.56 µM) | 0.277 ± 0.001 µM | >100 µM |
| (2,3-dichloro isoxazole methoxy phenol structure) | 5.21 ± 0.50 (at 1.56 µM) | 0.108 ± 0.01 µM | >100 µM |

TABLE 1-continued
Isoxazole and Benzamide Calcium Retention Capacity; Mitochondrial Swelling; and Rhodamine 123 (Rh123) uptake
| Structure | Calcium Retention Capacity (CRC/CRC$_0$ at 12.5 µM) | Mitochondrial swelling (EC50) | Rh123 uptake (EC50) |
|---|---|---|---|
| 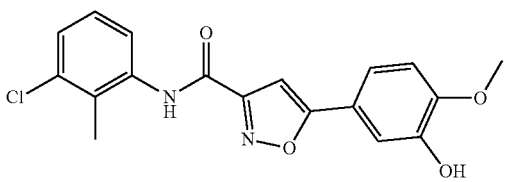 | 13.44 ± 0.93 (9.59 ± 0.85 at 1.56 µM) | 0.0000283 ± 0.0000048 µM | >100 µM |
| 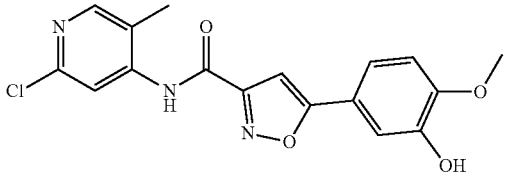 | 4.27 ± 0.40 | 0.366 ± 0.0475 µM | >100 µM |
| 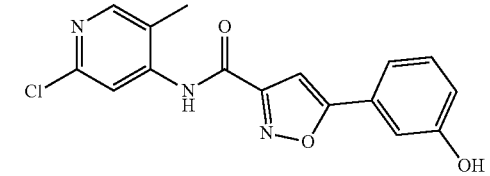 [SMILES: Cc1cnc(Cl)cc1NC(=O)c1cc(-c2cccc(O)c2)on1] | 5.51 ± 0.99 | 0.100 ± 0.0096 µM | >100 µM |
| 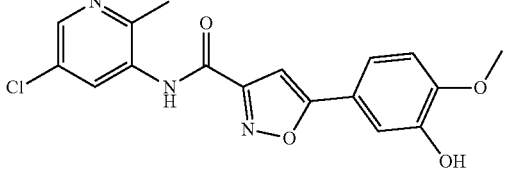 | 13.47 ± 1.32 (10.10 ± 1.14 at 1.56 µM) | 0.011 ± 0.0011 µM | >100 µM |
| 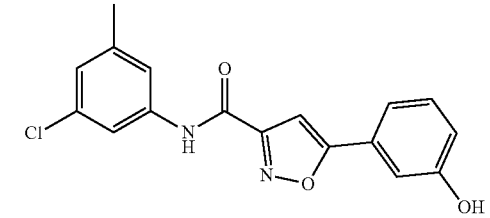 [SMILES: Cc1cc(Cl)cc(NC(=O)c2cc(-c3cccc(O)c3)on2)c1] | 9.34 ± 1.04 | 0.078 ± 0.0050 µM | >100 µM |
| 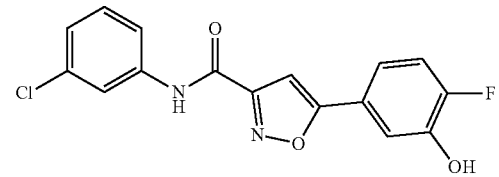 [SMILES: O=C(Nc1cccc(Cl)c1)c1cc(-c2ccc(F)c(O)c2)on1] | 10.17 ± 0.69 | 0.013 ± 0.0020 µM | >100 µM |
| 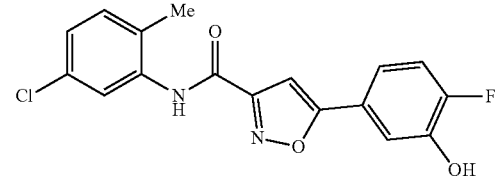 [SMILES: Cc1ccc(Cl)cc1NC(=O)c1cc(-c2ccc(F)c(O)c2)on1] | 19.28 ± 1.59 (15.21 ± 1.26 at 1.56 µM) | 0.000134 ± 0.000016 µM | >100 µM |

TABLE 1-continued

Isoxazole and Benzamide Calcium Retention Capacity; Mitochondrial Swelling; and Rhodamine 123 (Rh123) uptake

| Structure | Calcium Retention Capacity (CRC/CRC$_0$ at 12.5 µM) | Mitochondrial swelling (EC50) | Rh123 uptake (EC50) |
|---|---|---|---|
| (5-chloro-2-fluoroanilide isoxazole with 4-fluoro-3-hydroxyphenyl) | 10.07 ± 0.69 | 0.009 ± 0.0014 µM | >100 µM |
| (2,3-dichloroanilide isoxazole with 4-fluoro-3-hydroxyphenyl) | 9.37 ± 0.65 | 0.0554 ± 0.0041 µM | >100 µM |
| (3-chloro-5-methylanilide isoxazole with 4-fluoro-3-hydroxyphenyl) | 6.08 ± 0.52 | 0.819 ± 0.0589 µM | >100 µM |
| (5-chloro-2-methylpyridin-3-yl amide isoxazole with 4-fluoro-3-hydroxyphenyl) | 10.69 ± 1.00 (9.12 ± 0.88 at 1.56 µM) | 0.016 ± 0.0019 µM | >100 µM |
| (2-chloro-5-methylpyridin-4-yl amide isoxazole with 4-fluoro-3-hydroxyphenyl) | 3.48 ± 0.51 | 2.192 ± 0.1501 µM | >100 µM |
| (3,5-dichloroanilide isoxazole with 4-fluoro-3-hydroxyphenyl) | 7.14 ± 0.69 | 0.0756 ± 0.0092 µM | >100 µM |
| (3-chloro-2-methylanilide isoxazole with 4-fluoro-3-hydroxyphenyl) | 12.14 ± 0.55 (at 1.56 µM) | 0.000890 ± 0.000141 µM | >100 µM |

TABLE 1-continued

Isoxazole and Benzamide Calcium Retention Capacity; Mitochondrial Swelling; and Rhodamine 123 (Rh123) uptake

| Structure | Calcium Retention Capacity (CRC/CRC$_0$ at 12.5 μM) | Mitochondrial swelling (EC50) | Rh123 uptake (EC50) |
|---|---|---|---|
| (5-chloro-2-methylpyridin-3-yl isoxazole-3-carboxamide with 3-hydroxyphenyl) | 10.09 ± 0.91 (6.62 ± 0.89 at 1.56 μM) | 0.024 ± 0.0022 | >100 μM |
| (3-chlorophenyl cinnamide with 3-hydroxy-4-methoxyphenyl) | 11.05 ± 1.35 | 0.125 ± 0.0071 μM | >100 μM |
| (5-chloro-2-methylphenyl isoxazole-3-carboxamide with 3-hydroxyphenyl) | 14.99 ± 1.20 (9.63 ± 0.29 at 1.56 μM) | 0.0035 ± 0.0007 μM | >100 μM |
| (5-chloro-2-methoxy-N-(4-(2-(piperazin-1-yl)ethyl)phenyl)benzamide) | 1.37 ± 0.02 | 5.849 ± 0.3435 μM | >100 μM |
| (5-chloro-2-methoxy-N-(4-(2-morpholinoethyl)phenyl)benzamide) | 1.23 ± 0.02 | 9.003 ± 0.4036 μM | >100 μM |
| (5-chloro-2-methoxy-N-(4-(2-(piperidin-1-yl)ethyl)phenyl)benzamide) | 1.51 ± 0.01 | 2.684 ± 0.1661 μM | >100 μM |

TABLE 1-continued

Isoxazole and Benzamide Calcium Retention Capacity; Mitochondrial Swelling; and Rhodamine 123 (Rh123) uptake

| Structure | Calcium Retention Capacity (CRC/CRC$_0$ at 12.5 µM) | Mitochondrial swelling (EC50) | Rh123 uptake (EC50) |
|---|---|---|---|
| *structure* | 1.37 ± 0.02 | 7.614 ± 0.8388 | >100 µM |
| *structure* | 1.33 ± 0.06 | 9.239 ± 0.8596 µM | >100 µM |
| *structure* | 1.20 ± 0.00 | 8.117 ± 0.3877 µM | >100 µM |
| *structure* | 1.24 ± 0.04 | 6.866 ± 0.4230 | >100 µM |
| *structure* | 1.80 ± 0.00 | 1.541 ± 0.1006 µM | >100 µM |
| *structure* | 1.65 ± 0.06 | 2.148 ± 0.10 µM | >100 µM |
| *structure* | 1.31 ± 0.03 | 7.252 ± 0.5262 µM | >100 µM |

TABLE 1-continued
Isoxazole and Benzamide Calcium Retention Capacity; Mitochondrial Swelling; and Rhodamine 123 (Rh123) uptake
| Structure | Calcium Retention Capacity (CRC/CRC$_0$ at 12.5 μM) | Mitochondrial swelling (EC50) | Rh123 uptake (EC50) |
|---|---|---|---|
| 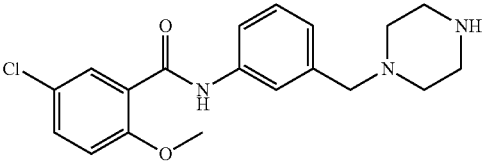 [SMILES: COc1ccc(Cl)cc1C(=O)Nc1cccc(CN2CCNCC2)c1] | 1.52 ± 0.06 | 3.273 ± 0.1498 μM | >100 μM |
| 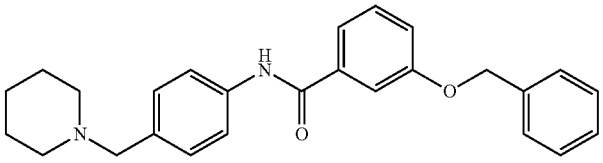 [SMILES: O=C(Nc1ccc(CN2CCCCC2)cc1)c1cccc(OCc2ccccc2)c1] | 3.54 ± 0.28 | 0.885 ± 0.1157 μM | 51.22 μM |
| 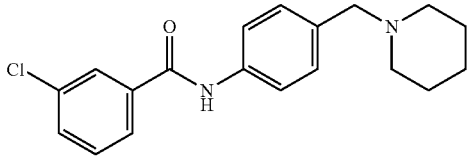 [SMILES: O=C(Nc1ccc(CN2CCCCC2)cc1)c1cccc(Cl)c1] | 1.16 ± 0.02 | 15.986 ± 1.5816 μM | >100 μM |
| 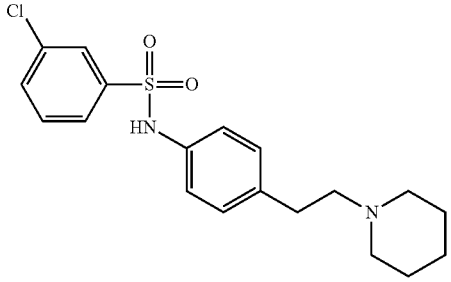 [SMILES: O=S(=O)(Nc1ccc(CCN2CCCCC2)cc1)c1cccc(Cl)c1] | 1.12 ± 0.02 | 38.723 ± 3.6723 μM | >100 μM |
| 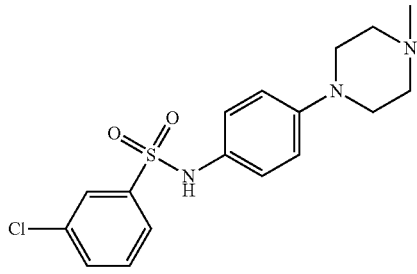 [SMILES: CN1CCN(c2ccc(NS(=O)(=O)c3cccc(Cl)c3)cc2)CC1] | 1.05 ± 0.03 | 37.473 ± 3.6327 μM | >100 μM |
| 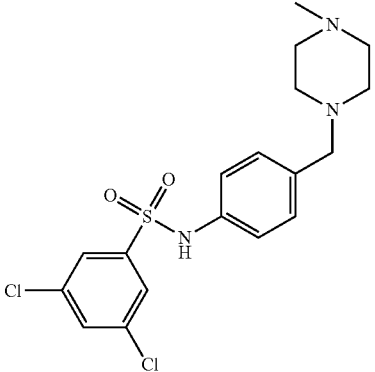 [SMILES: CN1CCN(Cc2ccc(NS(=O)(=O)c3cc(Cl)cc(Cl)c3)cc2)CC1] | 1.10 ± 0.02 | 29.207 ± 2.1016 μM | >100 μM |

TABLE 1-continued

Isoxazole and Benzamide Calcium Retention Capacity; Mitochondrial Swelling; and Rhodamine 123 (Rh123) uptake

| Structure | Calcium Retention Capacity (CRC/CRC$_0$ at 12.5 μM) | Mitochondrial swelling (EC50) | Rh123 uptake (EC50) |
| --- | --- | --- | --- |
| (3,5-dichlorophenyl sulfonamide - phenyl - ethyl - piperidine) | 1.17 ± 0.04 | 25.555 ± 1.8028 μM | >100 μM |
| (3,5-dichlorophenyl sulfonamide - phenyl - ethyl - piperazine) | 1.09 ± 0.05 | 21.387 ± 0.9832 μM | >100 μM |
| (3,5-dichlorophenyl sulfonamide - phenyl - N-methylpiperazine) | 1.11 ± 0.03 | 21.663 ± 1.0810 μM | >100 μM |
| (3-chloro-4-fluorophenyl sulfonamide - phenyl - ethyl - piperidine) | 1.07 ± 0.03 | 29.058 ± 2.9172 μM | >100 μM |
| (3-chloro-4-methoxyphenyl - isoxazole-3-carboxamide - 3-hydroxyphenyl) | 3.26 ± 0.32 | 0.189 ± 0.028 μM | >100 μM |

TABLE 1-continued

Isoxazole and Benzamide Calcium Retention Capacity; Mitochondrial Swelling; and Rhodamine 123 (Rh123) uptake

| Structure | Calcium Retention Capacity (CRC/CRC$_0$ at 12.5 μM) | Mitochondrial swelling (EC50) | Rh123 uptake (EC50) |
|---|---|---|---|
| 3-Cl-phenyl isoxazole 3-OH-phenyl benzamide | 5.47 ± 0.57 | 0.0788 ± 0.0058 μM | >100 μM |
| 4-Br-phenyl ketone propyl 4,4-dimethylpiperidine | 1.10 ± 0.05 | 18.023 ± 1.3275 μM | >100 μM |
| 4-Br-phenyl ketone propyl 4-isopropylpiperidine | 1.16 ± 0.05 | 9.999 ± 7.7771 μM | 64.75 ± 4.19 μM |
| 4-Br-phenyl ketone propyl 2,6-dimethylpiperidine | 1.01 ± 0.02 | 45.996 ± 1.3574 μM | >100 μM |
| 2,3-diCl-phenyl isoxazole 3-OH-phenyl benzamide | 4.00 ± 0.42 | 12.488 ± 0.6675 μM | >100 μM |
| 2,5-diCl-phenyl isoxazole 3-OH-phenyl benzamide | 4.67 ± 0.31 | 1.520 ± 0.0512 μM | 38.47 ± 3.98 μM |
| 3-Cl-2-OMe-phenyl isoxazole 3-OH-phenyl benzamide | 1.83 ± 0.17 | 42.728 ± 2.5933 μM | >100 μM |
| 3,5-diCl-phenyl isoxazole 3-OH-phenyl benzamide | 12.08 ± 1.92 (5.72 ± 0.25 at 1.56 μM) | 0.190 ± 0.017 μM | >100 μM |

TABLE 1-continued

Isoxazole and Benzamide Calcium Retention Capacity; Mitochondrial Swelling; and Rhodamine 123 (Rh123) uptake

| Structure | Calcium Retention Capacity (CRC/CRC$_0$ at 12.5 µM) | Mitochondrial swelling (EC50) | Rh123 uptake (EC50) |
|---|---|---|---|
| 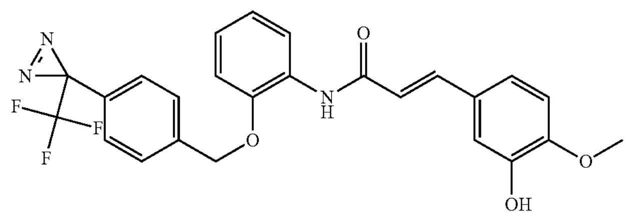 [SMILES: COc1ccc(/C=C/C(=O)Nc2ccccc2OCc2ccc(C3(C(F)(F)F)N=N3)cc2)cc1O] | 1.90 ± 0.11 | ND | ND |
| 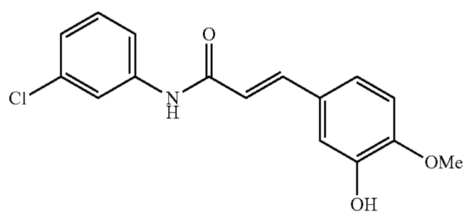 [SMILES: COc1ccc(/C=C/C(=O)Nc2cccc(Cl)c2)cc1O] | 14.02 ± 1.63 | ND | ND |
| 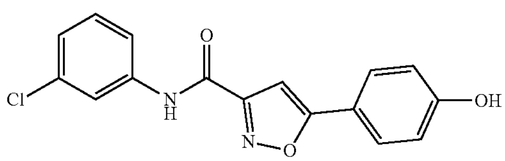 [SMILES: O=C(Nc1cccc(Cl)c1)c1cc(-c2ccc(O)cc2)on1] | 3.50 ± 0.57 | 2.210 ± 0.1738 µM | >100 µM |
| | 13.99 ± 1.50 (7.69 ± 0.61 at 1.56 µM) | 0.030 ± 0.0026 µM | >100 µM |
| 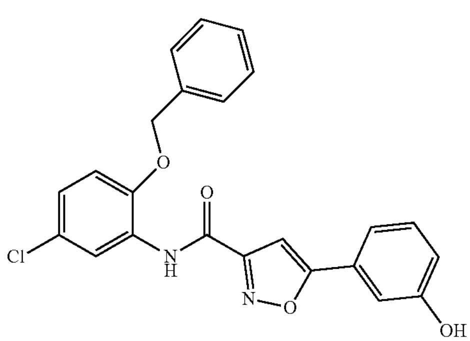 [SMILES: O=C(Nc1cc(Cl)ccc1OCc1ccccc1)c1cc(-c2cccc(O)c2)on1] | 1.59 ± 0.33 | 17.576 ± 2.2110 µM | >100 µM |
| 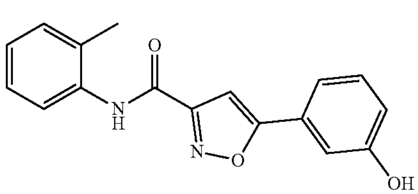 [SMILES: Cc1ccccc1NC(=O)c1cc(-c2cccc(O)c2)on1] | 8.16 ± 0.92 | 0.030 ± 0.0022 µM | >100 µM |

TABLE 1-continued

Isoxazole and Benzamide Calcium Retention Capacity; Mitochondrial Swelling; and Rhodamine 123 (Rh123) uptake

| Structure | Calcium Retention Capacity (CRC/CRC$_0$ at 12.5 μM) | Mitochondrial swelling (EC50) | Rh123 uptake (EC50) |
|---|---|---|---|
| (2-methylphenyl)-NH-C(O)-isoxazole-phenyl-OH | 2.94 ± 0.46 | 2.446 ± 0.1480 μM | >100 μM |
| (5-chloro-2-methylphenyl)-NH-C(O)-isoxazole-(3-hydroxy-4-methoxyphenyl) | 14.44 ± 0.58 (10.02 ± 0.34 at 1.56 μM) | 0.00000756 ± 0.00000122 μM | >100 μM |
| (3-chlorophenyl)-NH-C(O)-isoxazole-(3-hydroxyphenyl) | 4.13 ± 0.17 (at 1.56 μM) | 0.0788 ± 0.0058 μM | >100 μM |
| (5-chloro-2-fluorophenyl)-NH-C(O)-isoxazole-(3-hydroxyphenyl) | 3.77 ± 0.17 (at 1.56 μM) | 0.172 ± 0.014 μM | >100 μM |
| (3-chloro-2-methylphenyl)-NH-C(O)-isoxazole-(4-chloro-3-hydroxyphenyl) | 8.22 ± 0.58 (at 1.56 μM) | 0.000180 ± 0.000042 μM | >100 μM |
| (5-chloro-2-methylpyridin-3-yl)-NH-C(O)-isoxazole-(4-chloro-3-hydroxyphenyl) | 6.91 ± 0.47 (at 1.56 μM) | 0.00134 ± 0.00026 μM | >100 μM |
| (5-chloro-2-methylphenyl)-NH-C(O)-isoxazole-(4-chloro-3-hydroxyphenyl) | 6.21 ± 0.66 (at 1.56 μM) | 0.00216 ± 0.00045 μM | >100 μM |

TABLE 1-continued

Isoxazole and Benzamide Calcium Retention Capacity; Mitochondrial Swelling; and Rhodamine 123 (Rh123) uptake

| Structure | Calcium Retention Capacity (CRC/CRC$_0$ at 12.5 µM) | Mitochondrial swelling (EC50) | Rh123 uptake (EC50) |
|---|---|---|---|
| 5-(4-fluoro-3-hydroxyphenyl)-N-(5-chloro-2-methylphenyl)-1H-pyrazole-3-carboxamide | 10.92 ± 0.74 (at 1.56 µM) | 0.0014 ± 0.0002 µM | 30.4 ± 5.5 µM |
| 5-(3-hydroxy-4-methoxyphenyl)-N-(5-chloro-2-methylphenyl)-1H-pyrazole-3-carboxamide | 7.51 ± 0.47 (at 1.56 µM) | 0.0024 ± 0.0004 µM | >100 µM |
| N-(2,6-dimethylphenyl)-5-(3-hydroxyphenyl)isoxazole-3-carboxamide | 8.12 ± 0.59 (at 1.56 µM) | 0.0121 ± 0.0014 µM | >100 µM |
| N-(3-chlorophenyl)-5-(3-hydroxy-4-methoxyphenyl)isoxazole-3-carboxamide | 7.18 ± 0.87 | 0.035 ± 0.0042 µM | >100 µM |
| N-(3,5-dichlorophenyl)-5-(4-fluoro-3-hydroxyphenyl)isoxazole-3-carboxamide | 11.22 ± 1.22 | 0.076 ± 0.0092 µM | >100 µM |
| N-(3,5-dichlorophenyl)-5-(3-hydroxy-4-methoxyphenyl)isoxazole-3-carboxamide | 3.52 ± 0.44 | 0.277 ± 0.0010 µM | >100 µM |
| N-(2,3-dichlorophenyl)-5-(4-fluoro-3-hydroxyphenyl)isoxazole-3-carboxamide | 11.21 ± 1.38 | 0.071 ± 0.0011 µM | >100 µM |

TABLE 1-continued

Isoxazole and Benzamide Calcium Retention Capacity; Mitochondrial Swelling; and Rhodamine 123 (Rh123) uptake

| Structure | Calcium Retention Capacity (CRC/CRC$_0$) at 12.5 μM) | Mitochondrial swelling (EC50) | Rh123 uptake (EC50) |
|---|---|---|---|
| 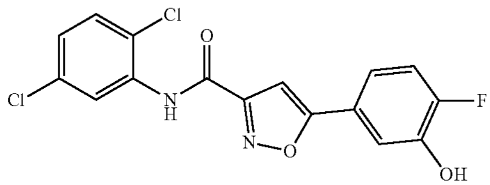 | 12.15 ± 1.36 (6.50 ± 0.77 at 1.56 μM) | 0.066 ± 0.0032 μM | >100 μM |
| 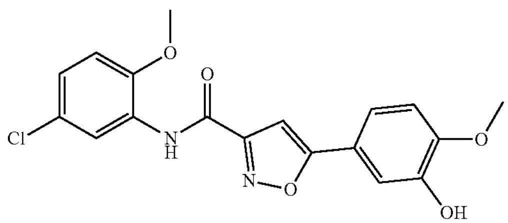 [SMILES: COc1ccc(-c2cc(C(=O)Nc3cc(Cl)ccc3OC)no2)cc1O] | 9.89 ± 1.31 (6.62 ± 0.84 at 1.56 μM) | 0.097 ± 0.0034 μM | >100 μM |
| 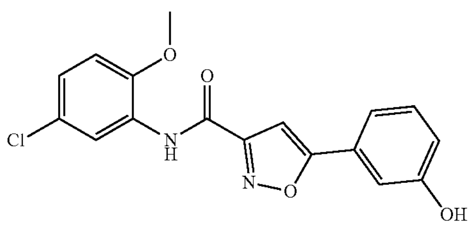 [SMILES: COc1ccc(Cl)cc1NC(=O)c1cc(-c2cccc(O)c2)on1] | 10.89 ± 1.34 (6.95 ± 1.15 at 1.56 μM) | 0.060 ± 0.0076 μM | >100 μM |
| 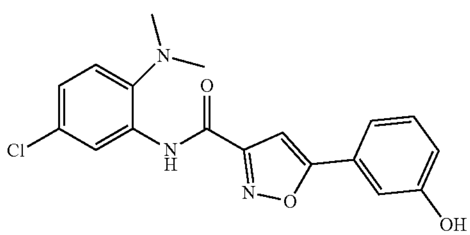 [SMILES: CN(C)c1ccc(Cl)cc1NC(=O)c1cc(-c2cccc(O)c2)on1] | 2.22 ± 0.38 | 1.612 ± 0.8658 μM | >100 μM |
| 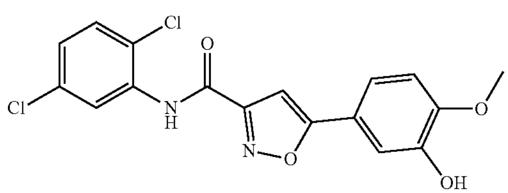 [SMILES: COc1ccc(-c2cc(C(=O)Nc3cc(Cl)ccc3F)no2)cc1O] | 9.59 ± 1.29 (4.34 ± 0.53 at 1.56 μM) | 0.146 ± 0.0115 μM | >100 μM |
| 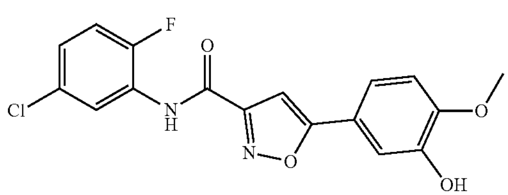 | 5.37 ± 0.58 | 0.217 ± 0.0518 μM | >100 μM |
| 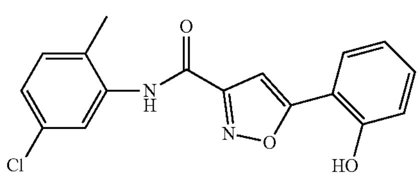 [SMILES: Cc1ccc(Cl)cc1NC(=O)c1cc(-c2ccccc2O)on1] | 2.10 ± 0.26 | 6.057 ± 0.7477 μM | >100 μM |

TABLE 1-continued

Isoxazole and Benzamide Calcium Retention Capacity; Mitochondrial Swelling; and Rhodamine 123 (Rh123) uptake

| Structure | Calcium Retention Capacity (CRC/CRC$_0$ at 12.5 µM) | Mitochondrial swelling (EC50) | Rh123 uptake (EC50) |
|---|---|---|---|
| (structure: 5-chloro-2-methylphenyl biphenyl-3-ol benzamide) | 2.59 ± 0.22 | 4.710 ± 0.3490 µM | >100 µM |
| (structure: chloro-methylpyridinyl isoxazole methoxyphenol carboxamide) | 4.27 ± 0.40 | 0.366 ± 0.0475 µM | >100 µM |
| Cyclosporin A | 5.13 ± 0.43 | 0.095 ± 0.0029 µM | >100 µM |

TABLE 2

Calcium Retention Capacity; Mitochondrial Swelling; & Rhodamine 123 (Rh123) uptake for Additional Examples

| Entry | Structure | Calcium Retention Capacity CRC/CRC$_0$ at 12.5 µM | Mitochondrial swelling EC$_{50}$ (µM) | Rh123 Assay EC$_{50}$ (µM) |
|---|---|---|---|---|
| 1 | (benzyloxy-fluoro-benzamide piperidinylmethyl aniline) | 10.8 ± 0.6 | 0.521 ± 0.046 | 58.6 ± 2.9 |
| 2 | (benzyloxy-fluoro-benzamide piperidinylmethyl aniline) | 13.3 ± 1.0 | 0.372 ± 0.028 | >100.00 |
| 3 | (benzyloxy-chloro-benzamide piperidinylmethyl aniline) | 2.26 ± 0.11 | 3.60 ± 0.17 | 75.7 ± 1.8 |

TABLE 2-continued

Calcium Retention Capacity; Mitochondrial Swelling; & Rhodamine 123 (Rh123) uptake for Additional Examples

| Entry | Structure | Calcium Retention Capacity $CRC/CRC_0$ at 12.5 µM | Mitochondrial swelling $EC_{50}$ (µM) | Rh123 Assay $EC_{50}$ (µM) |
|---|---|---|---|---|
| 4 | 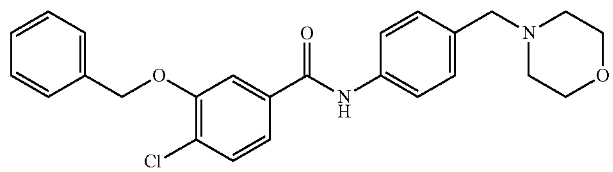 [SMILES: O=C(Nc1ccc(CN2CCOCC2)cc1)c1ccc(Cl)c(OCc2ccccc2)c1] | 8.81 ± 0.39 | 0.403 ± 0.031 | >100 |
| 5 | 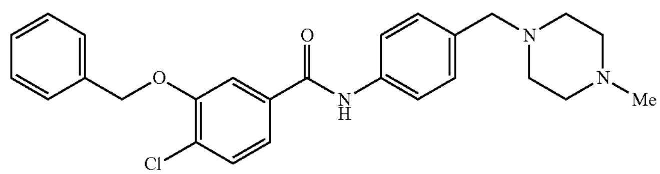 [SMILES: CN1CCN(Cc2ccc(NC(=O)c3ccc(Cl)c(OCc4ccccc4)c3)cc2)CC1] | 14.1 ± 1.1 | 0.423 ± 0.028 | 49.6 ± 4.3 |
| 6 | 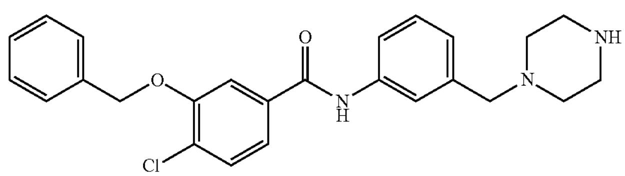 [SMILES: O=C(Nc1cccc(CN2CCNCC2)c1)c1ccc(Cl)c(OCc2ccccc2)c1] | 16.1 ± 1.5 | 0.286 ± 0.027 | 42.6 ± 3.1 |
| 7 | 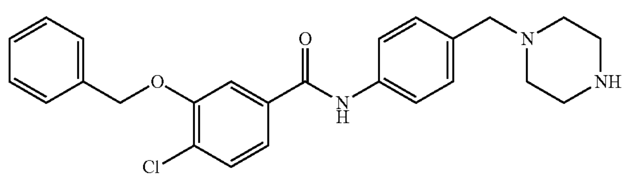 [SMILES: O=C(Nc1ccc(CN2CCNCC2)cc1)c1ccc(Cl)c(OCc2ccccc2)c1] | 18.3 ± 1.3 | 0.206 ± 0.021 | 46.4 ± 3.2 |
| 8 | 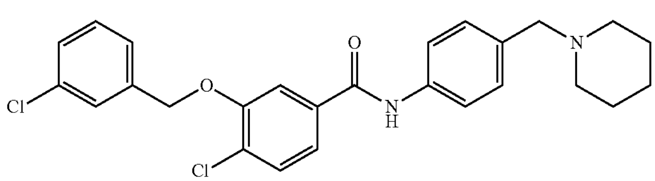 [SMILES: O=C(Nc1ccc(CN2CCCCC2)cc1)c1ccc(Cl)c(OCc2cccc(Cl)c2)c1] | 6.50 ± 1.20 | 1.19 ± 0.33 | 23.2 ± 1.3 |
| 9 | 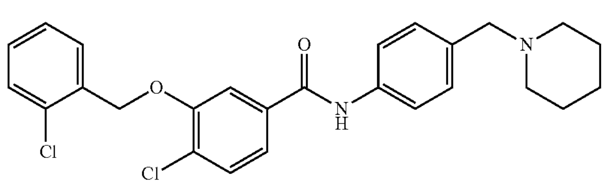 [SMILES: O=C(Nc1ccc(CN2CCCCC2)cc1)c1ccc(Cl)c(OCc2ccccc2Cl)c1] | 2.37 ± 0.41 | 4.00 ± 0.66 | >100 |
| 10 | 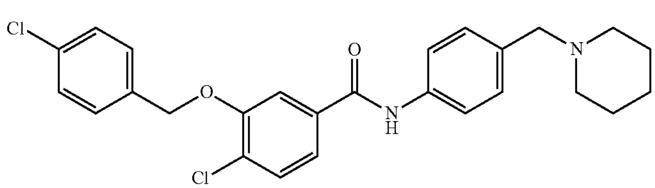 [SMILES: O=C(Nc1ccc(CN2CCCCC2)cc1)c1ccc(Cl)c(OCc2ccc(Cl)cc2)c1] | 5.91 ± 0.38 | 1.24 ± 0.39 | 24.7 ± 1.5 |
| 11 | 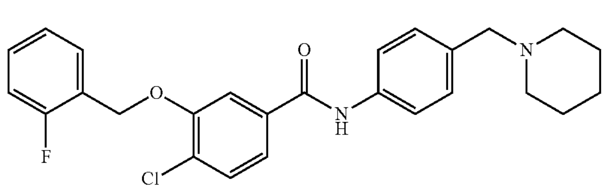 [SMILES: O=C(Nc1ccc(CN2CCCCC2)cc1)c1ccc(Cl)c(OCc2ccccc2F)c1] | 2.59 ± 0.54 | 1.39 ± 0.17 | >100 |

TABLE 2-continued

Calcium Retention Capacity; Mitochondrial Swelling; & Rhodamine 123 (Rh123) uptake for Additional Examples

| Entry | Structure | Calcium Retention Capacity CRC/CRC$_0$ at 12.5 μM | Mitochondrial swelling EC$_{50}$ (μM) | Rh123 Assay EC$_{50}$ (μM) |
|---|---|---|---|---|
| 12 | (structure) | 10.1 ± 0.8 | 0.49 ± 0.08 | 28.6 ± 1.1 |
| 13 | (GNX-865) | 7.67 ± 0.35 | 0.073 ± 0.007 | >100 |

Note:
Data are an average of >3 experiments ± SEM

Effects of Compounds of the Present Technology on Defects Present in Exon 9 col6a1 Morphant Zebrafish.

Zebrafish and embryo maintenance. Adult zebrafish were maintained in the facility of the University of Padova containing aerated, 28.5° C.-conditioned saline water according to standard protocols. Fish were kept under a 14 h light-10 h dark cycle. For mating, males and females were separated in the late afternoon, and were freed to start courtship the next morning, which ended with egg deposition and fecundation. Eggs were collected, washed with fish water (0.5 mM NaH$_2$PO$_4$, 0.5 mM NaHPO$_4$, 0.2 mg/L methylene blue, 3 mg/L instant ocean) and embryos were maintained at 28.5° C. All protocols and manipulations with zebrafish were performed as described in C. B. Kimmel, W. W. Ballard, S. R. Kimmel, B. Ullmann, T. F. Schilling, *Dev. Dyn.* 1995, 203, 253-310.

Morpholino injections. To reproduce the dominant negative UCMD or BM phenotype in zebrafish, we used an exon9 morpholino which targets exon 9 of the zebrafish col6a1 gene, as described in W. R. Telfer, A. S. Busta, C. G. Bonnemann, E. L. Feldman, J. J. Dowling, *Hum. Mol. Genet.* 2010, 19, 2433-2444 and A. Zulian, E. Rizzo, M. Schiavone, E. Palma, F. Tagliavini, B. Blaauw, L. Merlini, N. M. Maraldi, P. Sabatelli, P. Braghetta, P. Bonaldo, F. Argenton, P. Bernardi, *Hum. Mol. Genet.* 2014, 23, 5353-5363. Exon 9, col6a1: GAG AGC GGA AGA CGA ACC TTC ATTC (GeneTools, Inc.). A control morpholino, with no sequence homology in zebrafish genome was used. Embryos isolated after paired matings of wild-type zebrafish were injected at 1-2 cell stage using a WPI pneumatic PicoPump PV820 injector. Morpholino was injected at a concentration of 0.1 mM, corresponding to ~4 ng per embryo.

Compound treatment. Morphant embryos were dechorionated at 20 hpf and then treated with compound 60 (referred to as KSC-392-116 above) at 21 hpf, where compound 60 is illustrated below.

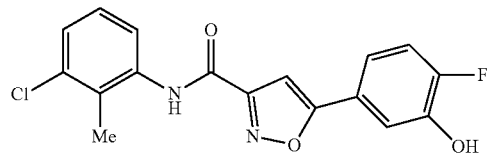

Untreated morphants and wild-type embryos were used as controls. Compound 60 was used at 5 and 10 μM and dissolved in fish water with 1% DMSO. Vehicle control treatment consisted of fish water with 1% DMSO. Analyses of compound effects on embryos were performed as described at 24 and 48 hpf.

Motor activity. Spontaneous coiling rates were recorded by observing the number of coiling events in 15 s for single embryos at 24 hpf using light microscopy. Touch-evoked escape response was measured at 48 hpf by observing the ability of larvae to escape after touching the body with a little tip. Embryos were subdivided into four groups according to their ability to escape: paralyzed with no ability to move, showing coiling events only, embryos with minor motor impairments, or normal embryos swimming in the fish water; these were assigned a score of 0, 1, 2, or 3, respectively. Statistical analysis was performed on mean scores at each experimental condition.

Birefringence assay. Muscle birefringence was measured at 48 hpf on tricaine-anesthetized embryos by taking advantage of muscle fiber anisotropy. It was measured using two polarizing filters on a Leica M165FC stereomicroscope. Briefly, anesthetized embryos were placed on a glass slide, and muscle light refraction was analyzed by using two polarizing filters. The first filter produces the polarized light to illuminate the sample, and the second polarizing filter, called the analyzer, calculates the angle of light refracted from muscle fibers. In particular, the top polarizing filter was twisted at a 90° angle until the light refracting through the muscle was visible through a stereomicroscope. Integrated area of birefringence was calculated by using ImageJ software, as disclosed in J. Berger, T. Sztal, P. D. Currie, *Biochem. Biophys. Res. Commun.* 2012, 423, 785-788. Birefringence values $\geq 2 \times 10^6$ (typical of wild-type individuals) were rated as normal, values between $1.9 \times 10^6$ and $0.6 \times 10^6$ were considered as an indication of mild disease, and values $\leq 0.6 \times 10^6$ were rated as an indication of severe myopathy. Statistical analysis was performed on the mean birefringence values at each experimental condition.

Statistical analysis. Differences between control and compound treated samples were determined by one-way ANOVA test with Bonferroni correction using GraphPad Prism (version 5.1 for Windows). Data represent the mean of at least five independent experiments (n=52 for each condition). SEM; $p<0.01$, *$p<0.001$ for FIG. 1. For FIG. 2, comparison between groups at different conditions was made using $\chi^2$ test and one-way ANOVA with Bonferroni correction; $p<0.01$, *$p<0.001$. For FIG. 3, the total number of embryos used is n=35 for each condition; *$p<0.05$, ***$p<0.001$, as determined by $\chi^2$ test and oneway ANOVA with Bonferroni correction.

Figure 2:
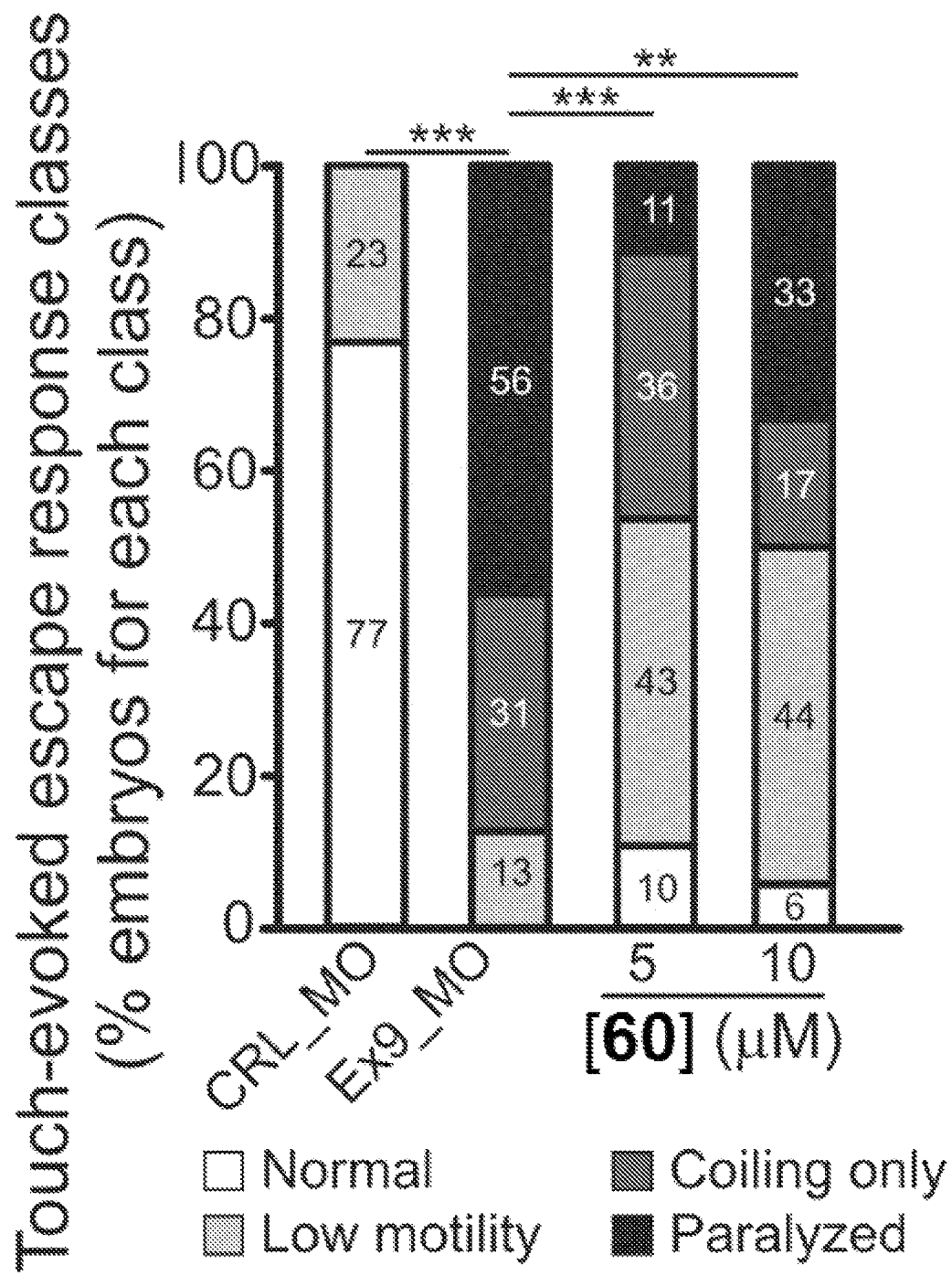
FIG. 2 provides the results of response evoked by touching control (CRL_MO) zebrafish embryos and exon 9 col6a1 morphant (Ex9_MO) zebrafish embryos with a pipette tip, where the exon 9 col6a1 morphant (Ex9_MO) zebrafish embryos were further tested with the indicated concentrations of a compound of the present technology.

As reflected in FIGS. 1 & 2, 87% of embryos injected with exon 9 morpholino showed severe motor impairments relative to control embryos. In contrast, exon9 morphants treated with compound 60, simply added to the fish water, showed a dramatic improvement in motor function as demonstrated with spontaneous coiling events (FIG. 1) or touch-evoked response (FIG. 2).

Figure 3:
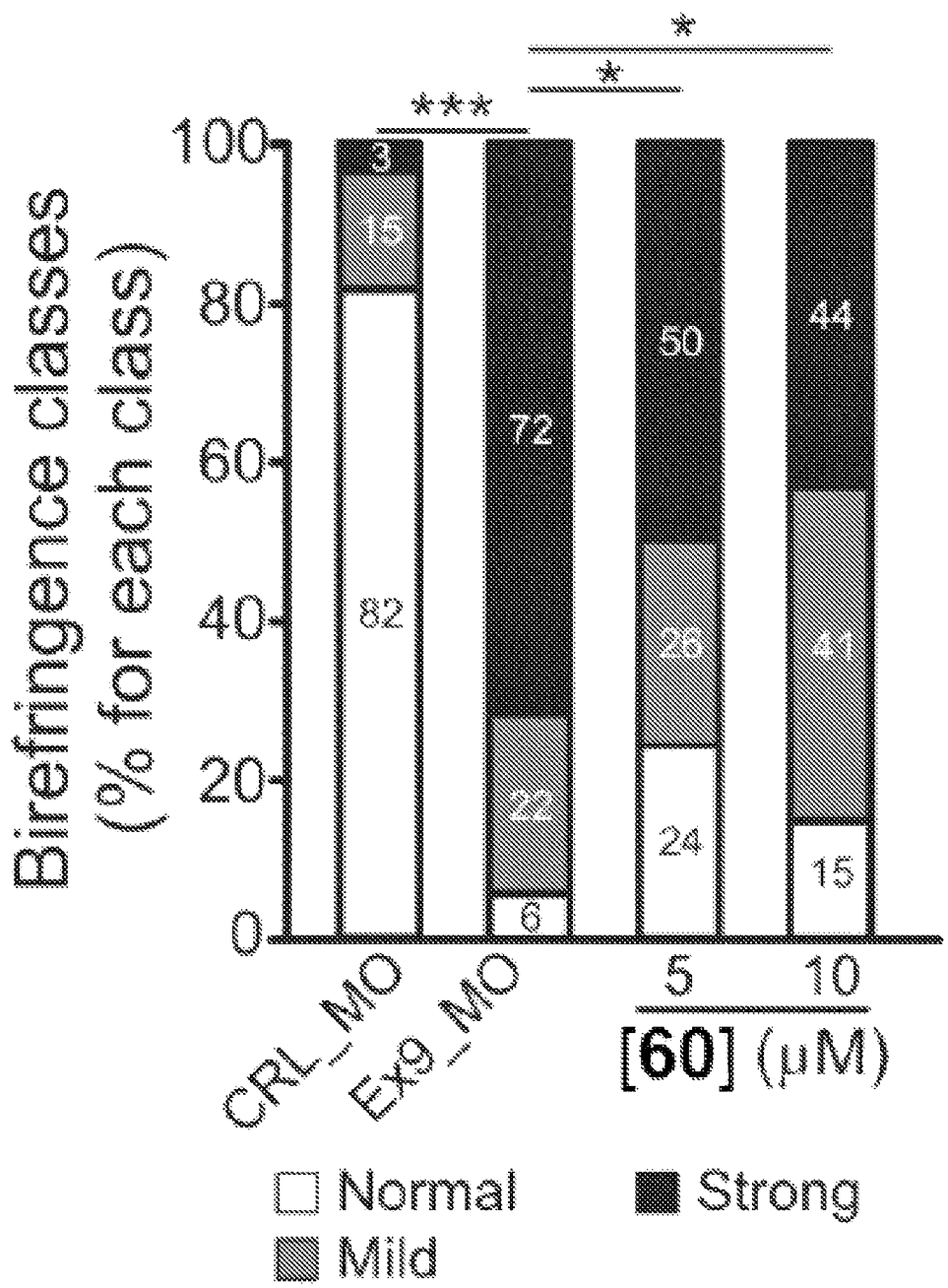
FIG. 3 discloses birefringence classes of control (CRL_MO) zebrafish embryos, exon 9 col6a1 morphant (Ex9_MO) zebrafish embryos, and exon 9 col6a1 morphant zebrafish embryos treated with the indicated concentrations of a compound of the present technology showing normal birefringence, mild myopathic phenotype, and strong myopathic phenotype, as indicated. All are shown at 48 hpf, where in the treated embryos treatment with the compound of the present technology occurred at 21 hpf.

To assess structural muscle organization, muscle birefringence was evaluated at 48 hpf. This technique evaluates muscle structural defects in zebrafish models of muscular dystrophy. Muscle birefringence was analyzed by taking advantage of muscle fiber anisotropy. As can be seen in FIG. 3, exon9 morphants exhibited severe muscle defects relative to controls, and these defects were largely ameliorated following treatment with compound 60. Indeed, total birefringence scores demonstrated that treatment with compound 60 generated significant recovery of muscle defects (ANOVA, $p<0.05$).

Mouse Model Assays of mtPTP-Dependent Muscular Dystrophy Illustrative of Therapeutic Effects of Compounds of the Present Technology.

A severe genetic human muscle disorder linked to collagen VI deficiency, resulting in persistent mtPTP opening, can be effectively mimicked in mice through genetic elimination of orthologous collagen VI genes. Importantly, in both humans and mice, defects could be reversed by treatment with Cyclosporin A (CsA) and with CsA derivatives that inhibit Cyclophilin D (CyPD), and hence the mtPTP. Here, following pharmacokinetic studies in mice, mouse models of these dystrophies will be used illustrate the therapeutic effects of compounds of the present technology.

Background: Anchoring and adhesion complexes at the surface of cells link the cytoskeleton to the surrounding extracellular matrix, thus maintaining cell integrity and cell signal transduction. These anchoring structures have a critical role in tissues undergoing extensive mechanical stress, like the skeletal muscle. Thus, it comes as no surprise that genetic defects in these anchoring complexes cause certain human muscular dystrophies. As one example, collagen VI (ColVI) is an essential component of the myofiber extracellular matrix, and mutations in ColVI result in two main human diseases, Ullrich congenital muscular dystrophy (UCMD) and Bethlem myopathy (BM)[1,2]. UCMD is a severe muscular dystrophy and segregates as a recessive disorder[1,3]. BM is a milder myopathy and, in contrast, is usually linked to a dominant mutation that generates pathology through dominant-negative mechanisms[4,5]. Mice generated by knock-out of the murine Col6a1 gene[6] are known models of UCMD[7]. Homozygous recessive animals display phenotypes that closely mimic defects observed in UCMD patients[7,8]. For example, in both humans and mice, muscle fibers have swollen/dilated mitochondria that lose their normal proton gradient following stimuli, something that does not affect mitochondria in normal fibers. These mitochondrial dysfunctions are indicative of defects originating from inappropriate mtPTP activation[7,9]. Consistent with this, inhibition of the mtPTP, either pharmacologically in humans and mice (CsA and non-immunosuppressive derivatives like Debio025 or NIM811)[10-13], or elimination of the mouse gene encoding CyPD[14], has been shown to improve mitochondrial changes and reduce myofiber cell death.

Test in mouse models of a mtPTP-dependent muscular dystrophy: Compounds of the present technology will be tested by IP injection of vehicle in addition to a variety of concentrations (e.g., 5 mg/kg, 1 mg/kg, etc.) of compounds of the present technology. In general, the techniques and analysis to be used will follow those outlined in earlier studies that showed that IP injections of CsA, and non-immunosuppressive derivatives of CsA (e.g., NIM811 and Debio025) are able to effectively counter the muscular defects present in these mutant animals[10,11]. In each case, mice will receive two daily doses of inhibitor or vehicle for up to 5 days. In each assay, differences between control WT, ColVI-null and ColVI-null mice treated with each derivative will be recorded. In all cases, data will be generated from at least 4 animals, expressed as mean±s.e.m, and analyzed with the unpaired Students t-test.

Rescue of muscle contractile strength by compounds of the present technology: Assessed will be tetanic (maximal), twitch tension, and relaxation time in muscle strips [specifically, the diaphragm and flexor digitorum brevis (FDB)] of the mice outlined above (N≥15). Typically, loss of ColVI results in dramatic loss of contractile strength (measured as $mN/mm^2$) compared to WT controls. Accordingly, it is expected that treatment with compounds of the present technology will restore contractile strength significantly when compared to ColVI-null mice, or restore muscle strength completely. Briefly, strips (width 1-2 mm) will be prepared, and mounted between a force transducer and a micromanipulator-controlled shaft in oxygenated Krebs solution at 25° C. The length of the strips will then be increased until force development during tetanus is maximal. The responses to a single stimulus (twitch) or to trains of stimuli at a variety of rates producing unfused or fused tetani will then be recorded. Cross-sectional area will be calculated from the weight.

Effects of compounds of the present technology on mitochondrial dysfunction in ColVI-null muscle fibers: Initial assessment of mtPTP function in treated ColVI-null animals will be by the CRC assay used to identify and characterize compounds of the present technology. Five hours after the last injection, mitochondria will be prepared from liver and muscle homogenates and the CRC of mitochondrial preparations assessed fluorometrically by application of trains of $Ca^{2+}$ pulses in the presence of Calcium Green 5N. The threshold for mtPTP activation will be determined based on the number of pulses required for mtPTP opening and compared statistically by assessment of the CRC/CRCmax. It is expected that, as with animals treated with Debio025, the threshold for mtPTP opening in ColVI-null liver and muscle mitochondria treated with compounds of the present technology will be increased relative to control, vehicle-injected, ColVI-null animals[11]. In order to assess the efficacy of compounds of the present technology in the treatment of ColVI-null animals, the mitochondrial transmembrane potential (ΔΨm) will be determined in situ based on the mitochondrial fluorescence of tetramethylrhodamine methyl ester (TMRM), a probe that accumulates in polarized mitochondria and is released when the transmembrane potential decreases. Addition of oligomycin, an inhibitor of F-ATP synthase, to FDB fibers from ColVI-null animals results in a dramatic decrease of TMRM mitochondrial fluorescence while, in contrast, fibers prepared from WT animals should show no immediate change in TMRM fluorescence. It has been shown that the mitochondrial dysfunction unmasked by oligomycin in ColVI-null muscle fibers has its basis in inappropriate activation of the mtPTP[7]. This anomalous depolarizing response in ColVI-null fibers has been shown to be due to F-ATP synthase operating in reverse and, as expected for a mtPTP-based phenotype, be corrected by treatment with CsA or CsA derivatives[7,8,10,11]. Consequently, rescue by compounds of the present technology of this muscle mitochondrial defect in ColVI-null fibers will be assessed. Briefly, FDB myofibers will be plated on glass coverslips, cultured as described in the art, mitochondria loaded by incubation with 20 nM TMRM and the response of control WT and ColVI-null fibers to application of oligomycin (6 µM) in the presence of vehicle or inhibitor recorded. The percentage of fibers (from at least 6 mice) depolarizing on the addition of oligomycin will be pooled and statistical significance determined. It is expected that treatment with compounds of the present technology will normalize the depolarization on application of oligomycin in the vast majority of ColVI-null fibers.

Effects of compounds of the present technology on mitochondrial ultrastructural defects and muscle cell apoptosis— Electron microscopic analysis has demonstrated that mitochondria in myofibers from ColVI-null animals display significant swelling, a typical feature of mtPTP opening, when compared to mitochondria in WT myofibers as well as an increase in the level of apoptosis (as assessed by the number of apoptotic nuclei). The effects of treatments with compounds of the present technology will be observed on both these mtPTP responses as described in the art[7,8,10,11]. FDB fibers from control WT, ColVI-null and treated ColVI-null mice will be fixed with glutaraldehyde and embedded in Epon E812 resin. Ultrathin sections will be prepared, stained with uranyl acetate and lead citrate, and observed by electron microscopy. It is expected that the percentage of fibers with altered mitochondrial structure (swollen mitochondria with disorganized cristae; average from at least three mice and 300 individual sections) will be significantly attenuated in ColVI-null animals treated with compounds of the present technology. Similarly, the number of apoptotic nuclei will be determined by TUNEL assay in 7 uM thick sections prepared from the diaphragm of vehicle-treated WT, ColVI-null and ColVI-null mice treated with compounds of the present technology. The total number of TUNEL-positive nuclei will be determined by commercially available kits (e.g., ApoTag) in randomly selected fibers and the number of total nuclei will be determined following staining with Hoechst staining by light-level microscopy.

REFERENCES

1. Pepe, G.; Bertini, E.; Bonaldo, P.; Bushby, K.; Giusti, B.; de Visser, M.; Guicheney, P.; Lattanzi, G.; Merlini, L.; Muntoni, F.; Nishino, I.; Nonaka, I.; Yaou, R. B.; Sabatelli, P.; Sewry, C.; Topaloglu, H.; van der Kooi, A., Bethlem myopathy (BETHLEM) and Ullrich scleroatonic muscular dystrophy: 100th ENMC international workshop, 23-24 Nov. 2001, Naarden, The Netherlands. Neuromuscul Disord 2002, 12, (10), 984-93.
2. Lampe, A. K.; Bushby, K. M., Collagen VI related muscle disorders. J Med Genet 2005, 42, (9), 673-85.
3. Camacho Vanegas, O.; Bertini, E.; Zhang, R. Z.; Petrini, S.; Minosse, C.; Sabatelli, P.; Giusti, B.; Chu, M. L.; Pepe, G., Ullrich scleroatonic muscular dystrophy is caused by recessive mutations in collagen type VI. Proc Natl Acad Sci USA 2001, 98, (13), 7516-21.
4. Jobsis, G. J.; Boers, J. M.; Barth, P. G.; de Visser, M., Bethlem myopathy: a slowly progressive congenital muscular dystrophy with contractures. Brain 1999, 122 (Pt 4), 649-55.
5. Pepe, G.; Lucarini, L.; Zhang, R. Z.; Pan, T. C.; Giusti, B.; Quijano-Roy, S.; Gartioux, C.; Bushby, K. M.; Guicheney, P.; Chu, M. L., COL6A1 genomic deletions in Bethlem myopathy and Ullrich muscular dystrophy. Ann Neurol 2006, 59, (1), 190-5.
6. Bonaldo, P.; Braghetta, P.; Zanetti, M.; Piccolo, S.; Volpin, D.; Bressan, G. M., Collagen VI deficiency induces early onset myopathy in the mouse: an animal model for Bethlem myopathy. Hum Mol Genet 1998, 7, (13), 2135-40.
7. Irwin, W. A.; Bergamin, N.; Sabatelli, P.; Reggiani, C.; Megighian, A.; Merlini, L.; Braghetta, P.; Columbaro, M.; Volpin, D.; Bressan, G. M.; Bernardi, P.; Bonaldo, P., Mitochondrial dysfunction and apoptosis in myopathic mice with collagen VI deficiency. Nat Genet 2003, 35, (4), 367-71.
8. Maraldi, N. M.; Sabatelli, P.; Columbaro, M.; Zamparelli, A.; Manzoli, F. A.; Bernardi, P.; Bonaldo, P.; Merlini, L., Collagen VI myopathies: from the animal model to the clinical trial. Adv Enzyme Regul 2009, 49, (1), 197-211.
9. Angelin, A.; Tiepolo, T.; Sabatelli, P.; Grumati, P.; Bergamin, N.; Golfieri, C.; Mattioli, E.; Gualandi, F.; Ferlini, A.; Merlini, L.; Maraldi, N. M.; Bonaldo, P.; Bernardi, P., Mitochondrial dysfunction in the pathogenesis of Ullrich congenital muscular dystrophy and prospective therapy with cyclosporins. Proc Natl Acad Sci USA 2007, 104, (3), 991-6.
10. Zulian, A.; Rizzo, E.; Schiavone, M.; Palma, E.; Tagliavini, F.; Blaauw, B.; Merlini, L.; Maraldi, N. M.; Sabatelli, P.; Braghetta, P.; Bonaldo, P.; Argenton, F.; Bernardi, P., NIM811, a cyclophilin inhibitor without immunosuppressive activity, is beneficial in collagen VI congenital muscular dystrophy models. Hum Mol Genet 2014, 23, (20), 5353-63.
11. Tiepolo, T.; Angelin, A.; Palma, E.; Sabatelli, P.; Merlini, L.; Nicolosi, L.; Finetti, F.; Braghetta, P.; Vuagniaux, G.; Dumont, J. M.; Baldari, C. T.; Bonaldo, P.; Bernardi, P., The cyclophilin inhibitor Debio 025 normalizes mitochondrial function, muscle apoptosis and ultrastructural defects in Col6a1-/- myopathic mice. Br J Pharmacol 2009, 157, (6), 1045-52.
12. Merlini, L.; Sabatelli, P.; Armaroli, A.; Gnudi, S.; Angelin, A.; Grumati, P.; Michelini, M. E.; Franchella, A.; Gualandi, F.; Bertini, E.; Maraldi, N. M.; Ferlini, A.; Bonaldo, P.; Bernardi, P., Cyclosporine A in Ullrich congenital muscular dystrophy: long-term results. Oxid Med Cell Longev 2011, 2011, 139194.
13. Merlini, L.; Angelin, A.; Tiepolo, T.; Braghetta, P.; Sabatelli, P.; Zamparelli, A.; Ferlini, A.; Maraldi, N. M.; Bonaldo, P.; Bernardi, P., Cyclosporin A corrects mitochondrial dysfunction and muscle apoptosis in patients with collagen VI myopathies. Proc Natl Acad Sci USA 2008, 105, (13), 5225-9.

14. Palma, E.; Tiepolo, T.; Angelin, A.; Sabatelli, P.; Maraldi, N. M.; Basso, E.; Forte, M. A.; Bernardi, P.; Bonaldo, P., Genetic ablation of cyclophilin D rescues mitochondrial defects and prevents muscle apoptosis in collagen VI myopathic mice. Hum Mol Genet 2009, 18, (11), 2024-31.
15. Shah, V. P.; Midha, K. K.; Dighe, S.; McGilveray, I. J.; Skelly, J. P.; Yacobi, A.; Layloff, T.; Viswanathan, C. T.; Cook, C. E.; McDowall, R. D.; et al., Analytical methods validation: bioavailability, bioequivalence and pharmacokinetic studies. Conference report. Eur J Drug Metab Pharmacokinet 1991, 16, (4), 249-55.
16. Xu, X.; Zhou, Q.; Korfmacher, W. A., Development of a low volume plasma sample precipitation procedure for liquid chromatography/tandem mass spectrometry assays used for drug discovery applications. Rapid Commun Mass Spectrom 2005, 19, (15), 2131-6.
17. International Patent Pub. "Acrylamino derivative useful as inhibitors of the mitochondrial permeability transition." WO 2010/049768 A1.
18. Di Lisa, F.; Carpi, A.; Giorgio, V.; Bernardi, P., The mitochondrial permeability transition pore and cyclophilin D in cardioprotection. Biochim Biophys Acta 2011, 1813, (7), 1316-22.
19. Di Lisa, F.; Menabo, R.; Canton, M.; Barile, M.; Bernardi, P., Opening of the mitochondrial permeability transition pore causes depletion of mitochondrial and cytosolic NAD+ and is a causative event in the death of myocytes in postischemic reperfusion of the heart. J Biol Chem 2001, 276, (4), 2571-5.
20. Di Lisa, F.; Bernardi, P., Mitochondria and ischemia-reperfusion injury of the heart: fixing a hole. Cardiovasc Res 2006, 70, (2), 191-9.
21. Su, K. G.; Savino, C.; Marracci, G.; Chaudhary, P.; Yu, X.; Morris, B.; Galipeau, D.; Giorgio, M.; Forte, M.; Bourdette, D., Genetic inactivation of the p66 isoform of ShcA is neuroprotective in a murine model of multiple sclerosis. Eur J Neurosci 2012, 35, (4), 562-71.
22. Forte, M.; Gold, B. G.; Marracci, G.; Chaudhary, P.; Basso, E.; Johnsen, D.; Yu, X.; Fowlkes, J.; Rander, M.; Stem, K.; Bernardi, P.; Bourdette, D., Cyclophilin D inactivation protects axons in experimental autoimmune encephalomyelitis, an animal model of multiple sclerosis. Proc Natl Acad Sci USA 2007, 104, (18), 7558-63.
23. Wang, X.; Carlsson, Y.; Basso, E.; Zhu, C.; Rousset, C. I.; Rasola, A.; Johansson, B. R.; Blomgren, K.; Mallard, C.; Bernardi, P.; Forte, M. A.; Hagberg, H., Developmental shift of cyclophilin D contribution to hypoxic-ischemic brain injury. J Neurosci 2009, 29, (8), 2588-96.

Effect of Compounds of the Present Technology on Myocardial Function and Response to Reperfusion Injury.

In this example, the ability of compounds of the present technology to prevent ischemia/reperfusion (IR) injury will be assessed.

Modified Langendorff Model

The Langendorff rodent heart model is widely employed in studies of myocardial function and responses to injury (e.g. ischaemia). For whole-heart studies, male Sprague-Dawley rats (7-9 weeks old) will be injected with pentobarbital (35 m/kg, ip injection) and hearts excised with midline thoracotomy. The aortas will be secured around a cannula of a modified Langendorff apparatus and retrogradely perfused (perfusion pressure of 75 mm Hg) with a modified Krebs-Henseleit buffer containing (in mM): 118 NaCl, 24 NaHCO$_3$, 4.75 KCl, 1.2 KH$_2$PO$_4$, 1.2 MgSO$_4$, 2.0 CaCl$_2$, and 10 glucose (gassed with 95/5% O$_2$/CO$_2$). Hearts will be bathed in a buffer-filled perfusion chamber maintained at 37° C. for the duration of the experiments. Following the initiation of perfusion, hearts will be instrumented for the simultaneous observation of mechanical and electrical function. A buffer-filled latex balloon (size 5, Harvard Apparatus, Holliston, Mass., USA), calibrated at the beginning of each day using a digital manometer, will be inserted into the left ventricle (via the mitral valve) for the measurement of left ventricular developed pressure (LVDP), with balloon volume adjusted to establish a diastolic pressure of 5-8 mm Hg. Three electrodes will be placed into the buffer filled perfusion chamber for the measurement of the volume-conducted electrocardiogram (ECG). Coronary flow rates will be monitored constantly with a flow probe (Transconic Systems, Ithaca, N.Y., USA) connected in series with the perfusion line, and normalized to heart wet weight (in grams) at the end of each experiment. All physiological parameters will be continuously monitored and stored on a personal computer using commercially available software (e.g., Chart, AD Instruments, Colorado Springs, Colo., USA). Heart rate will be calculated using the LVDP trace, and maximal rates of contraction and relaxation (±dP/dt) will be calculated using the derivative of the LVDP trace.

Ischemia/Reperfusion Protocol and Compound Treatments

Following a 10 minute baseline period, ischemia/reperfusion will be initiated. Hearts will be exposed to global no-flow ischemia by stopping perfusion for 20 min. At the end of the index ischemia, static buffer from the perfusion lines will be washed out (via an accessory port proximal to the aortic cannula), and reperfusion will be ensued for 2 h either with Krebs buffer alone (control) or Krebs buffer containing a predetermined concentration of the compound of the present technology. At the end of reperfusion, the left ventricle will be dissected, sliced into 5 mm-thick slices, incubated in 1% triphenyltetrazolium chloride (TTC) for 10 min (37° C.) and digitally photographed for subsequent infarct size analysis. Infarct size will be expressed as a percentage of the left ventricle (% area at risk (AAR)) (calculated using ImageJ software, NIH, Bethesda, Md., USA).

The results are expected to show that treatment with a compound of the present technology significantly decrease infarct size and LVDP, and/or increases the maximal rates of contraction and relaxation (±dP/dt). Thus, the results are expected to show that compounds of the present technology are useful to prevent or treat ischemia/reperfusion injury of the heart in a subject in need thereof.

While some embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A compound according to Formula I:

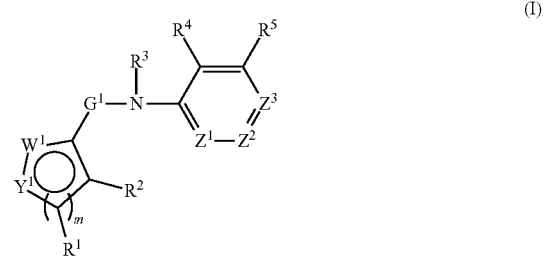

or a pharmaceutically acceptable salt thereof, wherein:

$Y^1$ is O;

$W^1$ is N;

$Z^1$, $Z^2$, and $Z^3$ are each independently CH, C—$R^9$, or N;

m is 1;

$G^1$ is C=O;

$R^1$ is

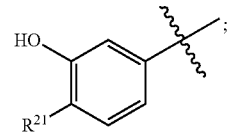

$R^2$, $R^4$, $R^5$, and $R^9$ are independently at each occurrence hydrogen, halogen, hydroxyl, alkyl, cycloalkyl, alkenyl, alkoxy, alkynyl, amino, aminosulfinyl, aminosulfonyl, sulfinyl, sulfonyl, sulfonyloxy, aminosulfonyloxy, aminosulfinyloxy, aminosulfonylamino, acylamino, aminocarbonyloxy, aminocarbonylamino, aminothiocarbonylamino, aminocarbonyl, acyloxy, aryl, heteroaryl, heterocyclyl, cyano, nitro, carboxyl, carboxyl ester, (carboxyl ester)amino, (carboxyl ester)oxy, acyl, or formyl; or two adjacent $R^4$, $R^5$, and $R^9$ together form an aryl, heteroaryl, or heterocyclyl ring;

$R^3$ is hydrogen, alkyl, cycloalkyl, alkenyl, or alkynyl; and $R^{21}$ is F or Cl.

2. The compound of claim 1, wherein $R^2$, $R^4$, $R^5$, and $R^9$ are independently at each occurrence hydrogen, $C_1$-$C_8$ alkyl, $C_3$-$C_8$ cycloalkyl, $C_1$-$C_8$ alkenyl, $C_2$-$C_8$ alkynyl, aryl, cyano, carboxyl, carboxyl ester, acyl, formyl, $C_3$-$C_7$ heteroaryl, or $C_3$-$C_7$ heterocyclyl, or two adjacent $R^4$, $R^5$, and $R^9$ together form an aryl, heteroaryl, or heterocyclyl ring.

3. The compound of claim 2, wherein $Z^1$ is CH.

4. The compound of claim 1, wherein $Z^1$ is CH.

5. The compound of claim 1, wherein the compound is a compound of Formula-IIa:

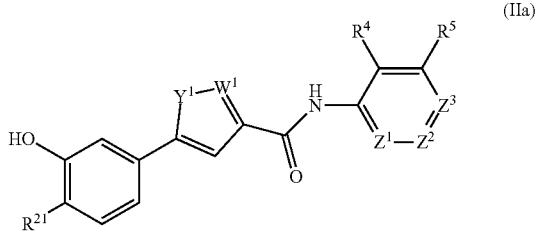

or a pharmaceutically acceptable salt thereof.

6. The compound of claim 1, wherein the compound is

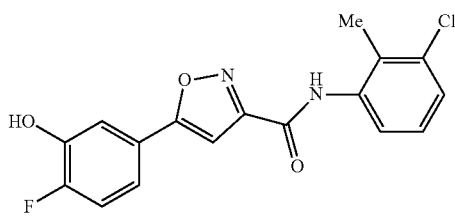 [SMILES: Cc1c(Cl)cccc1NC(=O)c1cc(-c2ccc(F)c(O)c2)on1]

or a pharmaceutically acceptable salt thereof.

7. A composition comprising a compound of claim 1 and a pharmaceutically acceptable excipient.

8. The composition of claim 7, wherein the compound is a compound of Formula-IIa:

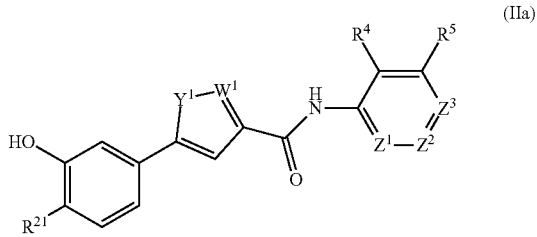

or a pharmaceutically acceptable salt thereof.

9. A composition comprising a compound of claim 6 and a pharmaceutically acceptable excipient.

10. A method for treating a disease in a subject having said disease, wherein the method comprises administering an effective amount of a compound of claim 1 to the subject, wherein the disease is multiple sclerosis, amyotropic lateral sclerosis, ischemic reperfusion injury, Alzheimer's disease, Huntington's disease, Parkinson's disease, insulin-induced hypoglycemia, cerebral ischemia, brain damage from epilepsy or experimental trauma, Bethlem myopathy, pancreatitis, hepatitis, type II diabetes, diabetic retinopathy, muscular dystrophy, traumatic brain injury, heart infarction, or stroke.

11. The method of claim 10, wherein the compound is a compound of Formula-IIa:

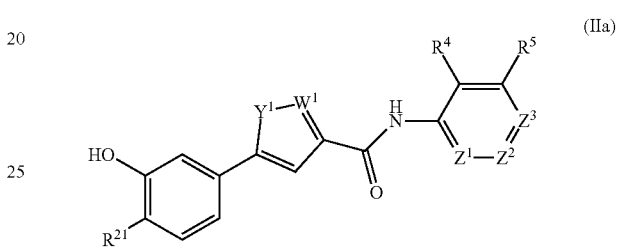

or a pharmaceutically acceptable salt thereof.

12. A method for inhibiting a mitochondrial permeability transition pore, wherein the method comprises contacting a cell with an effective amount of a compound of claim 1.

13. A method for treating a condition in a subject having said condition, wherein the method comprises administering to a patient an effective amount of a compound of claim 1; and the condition in the subject is mediated by $[Ca^{2+}]$ dysregulation or an accumulation of a reactive oxygen species.

* * * * *